(12) United States Patent
Hendrickson

(10) Patent No.: US 6,171,857 B1
(45) Date of Patent: Jan. 9, 2001

(54) LEUCINE ZIPPER PROTEIN, KARP-1 AND METHODS OF REGULATING DNA DEPENDENT PROTEIN KINASE ACTIVITY

(75) Inventor: Eric A. Hendrickson, Providence, RI (US)

(73) Assignee: Brown University Research Foundatiion, Providence, RI (US)

( * ) Notice: Under 35 U.S.C. 154(b), the term of this patent shall be extended for 0 days.

(21) Appl. No.: 09/173,914

(22) Filed: Oct. 16, 1998

Related U.S. Application Data
(60) Provisional application No. 60/064,557, filed on Oct. 17, 1997.

(51) Int. Cl.⁷ .......................... C12N 15/85; C12N 15/86; C12N 15/63; C07H 21/02; C07H 21/04
(52) U.S. Cl. ................... 435/325; 435/252.1; 435/320.1; 536/23.1; 536/23.5; 536/24.3; 536/24.31; 536/24.33
(58) Field of Search .................................. 536/23.5, 23.1, 536/24.31, 24.3, 24.33, 24.5; 435/320.1, 325, 252.1

(56) References Cited

PUBLICATIONS

Myung et al., KARP–1: a novel leucine zipper protein expressed from th eKu86 autoantigen locus is implicated in the control of DNA–dependent protein kinase activity. EMBO Journal, vol. 16, No. 11, pp. 3172–3184, 1997.*

\* cited by examiner

Primary Examiner—George C. Elliott
Assistant Examiner—Janet Epps
(74) Attorney, Agent, or Firm—Wolf, Greenfield & Sacks, P.C.

(57) ABSTRACT

The invention describes novel nucleic acids encoding the KARP-1 polypeptide, including fragments and biologically functional variants thereof. Also included are polypeptides and fragments thereof encoded by such nucleic acids, and antibodies relating thereto. Methods and products for using such nucleic acids and polypeptides also are provided.

16 Claims, 16 Drawing Sheets

| | | |
|---|---|---|
| 1 | tttaagtaaatctgtcgtactagCGTTTCAGGCGGCTCAAACACCACACGCCCCCGACTA | 60 |
| 61 | CGGCGGAATGGAGAGAATGTGCGCATGCTCGGCGGGAATCTGCGCATGCTCGGAGAGAAT | 120 |
| |           M  L  G  G  N  L  R  M  L  G  E  N | |
| |              *          *          * | |
| 121 | CTGCGCATGCTCGGCCGGAATCTGCGCGAGCTCGGCGGGAATCTGCGCAAGCTCGGCGGG | 180 |
| | L  R  M  L  G  R  N  L  R  E  L  G  G  N  L  R  K  L  G  G | |
| | *     *        *        *          *        * | |
| 181 | AATCTGCGCATGCTCAGAGTTCCGGGGCACGGTTTCCCCGCCCCTTTCAGGCCTAGCAGG | 240 |
| | N  L  R  M  L  R  V  P  G  H  G  F  P  A  P  F  R  P  S  R | |
| |     *        *                                +        + | |
| 241 | AAACGAAGCGGCTCTTTCCGCTATCTGCCGCTTGTCCACCGGAAGCGAGTTGCGACACGG | 300 |
| | K  R  S  G  S  F  R  Y  L  P  L  V  H  R  K  R  V  A  T  R | |
| | +  +          +                    +  +  +        + | |
| 301 | CAGGTTCCCGCCCGGAAGAAGCGACCAGAGCGCCTGAGGACCGGCAACATGGTGCGGTCG | 360 |
| | Q  V  P  A  R  K  K  R  P  E  R  L  R  T  G  N  M  V  R  S | |
| |           +  +  +  +        +      +            Ku86> | |

FIG. 1

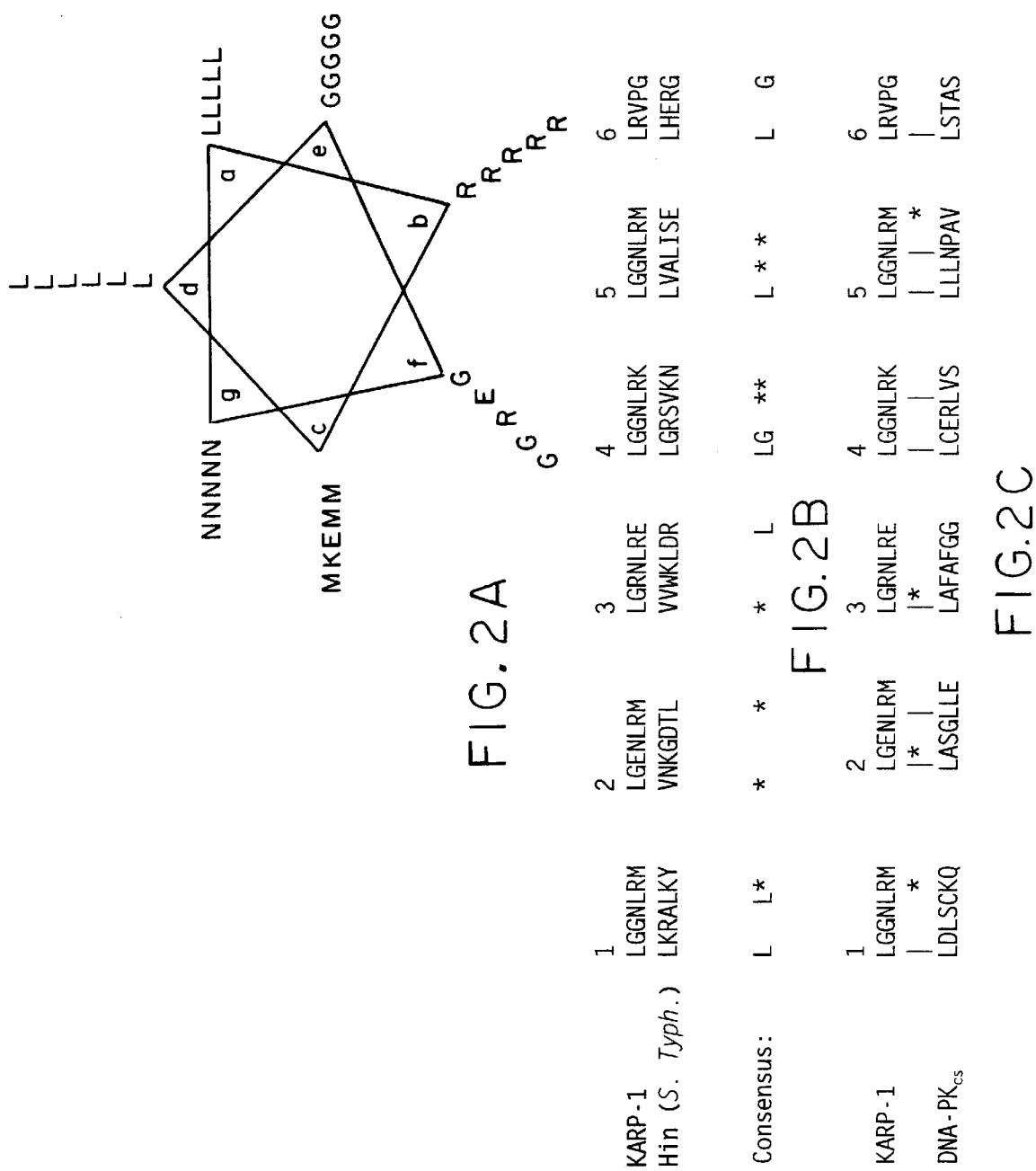

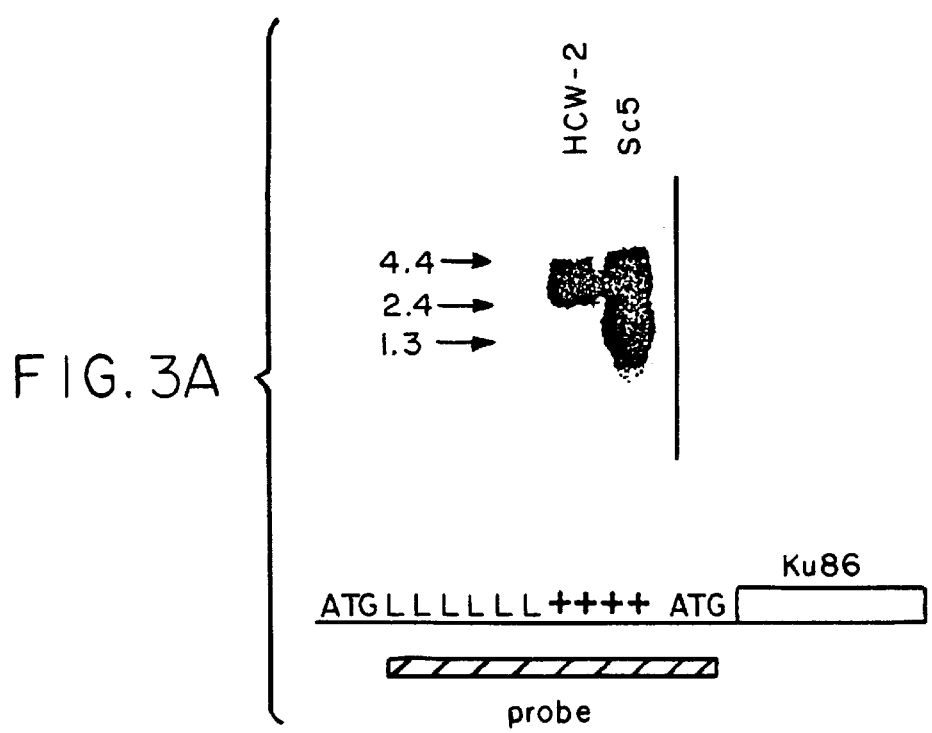

FIG. 3A

```
  1 MLGGNLRMLGENVRMLGRNLRELGGNLRKLGGNLRMLRVPGHGFPAPFRP
 51 SRKRSGSFRYLPLVHRKRVATRQVPARKKRPKRLRTGNMVRSGNKAAVVL
101 CVDVGFTMSNSIPGIESPFEQAKKVITMFVQRQVFAENKDEIALVLFGTD
151 GTDNPLSGGDQYQNITVHRHLMLPDFDLLEDIESKIQPGSQQADFLDALI
201 VSMDVIQHETIGKKFEKRHIEIFTDLSSRFSKSQLDIIIHSLEKCDISLQ
251 FFLPFSLGKEDGSGDRGDGPFRLGGHGPSFPLKGITEQQKEGLEIVKMVM
301 ISLEGEDGLDEIYSFSESLRKLCVFKKIERHSIHWPCRLTIGSNLSIRIA
351 AYKSILQERVKKTWTVVDAKTLKKEDIQKETVYCLNDDDETEVLKEDIIQ
401 GFRYGSDIVPFSKVDEEQMKYKSEGKCFSVLGFCKSSQVQRRFFMGNQVL
451 KVFAARDDEAAAVALSSLIHALDDLDMVAIVRYAYDKRANPQVGVAFPHI
501 KHNYECLVYVQLPFMEDLRQYMFSSLKNSKKYAPTEAQLNAVDALIDSMS
551 LAKKDEKTDTLEDLFPTTKIPNPRFQRLFQCLLHRALHPREPLPPIQQHI
601 WNMLNPPAEVTTKSQIPLSKIKTLFPLIEAKKKDQVTAQEIFQDNHEDGL
651 TAKKLKTEQGGAHFSVSSLAEGSVTSVGSVNPAENFRVLVKQKKASFEEA
701 SNQLINHIEQFLDTNETPYFMKSIGCIRAFREEAIKFSEEQRFNNLLKAL
751 QEKVEIKQLNHFWEIVVQDGITLITKEEASGSSVTAEEAKKFLAPKDKPS
801 GDTAAVFEEGGDVDDLLDMI*
```

FIG. 5

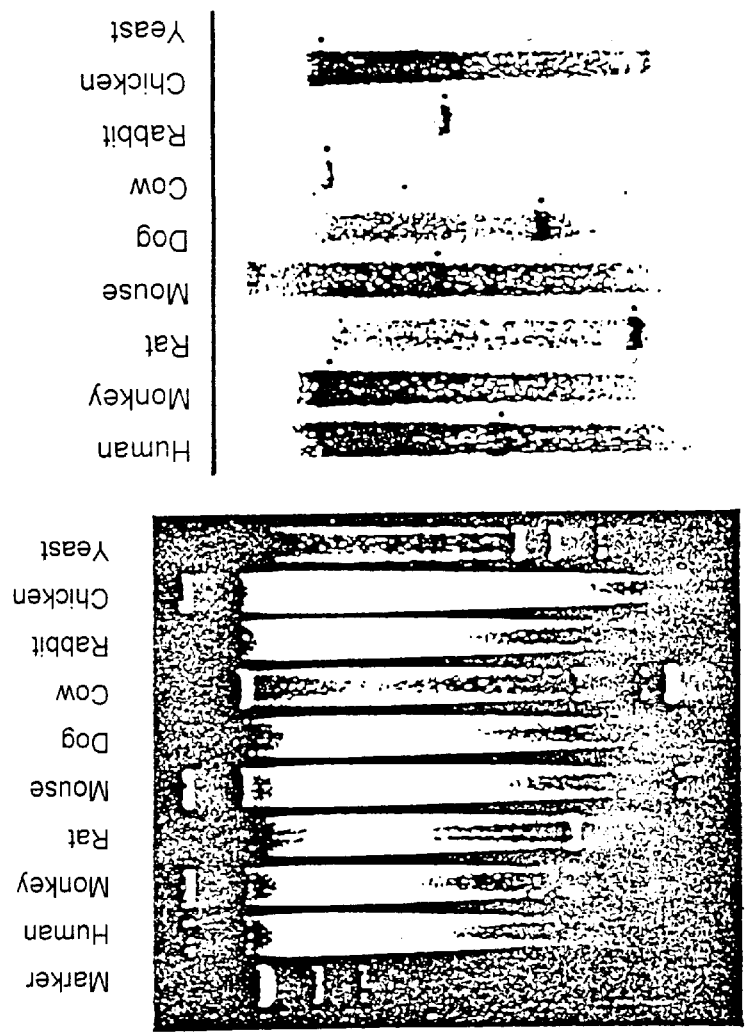
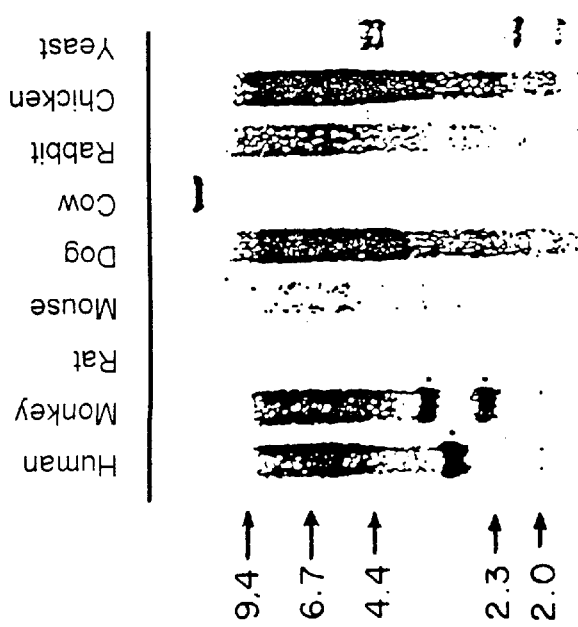
FIG. 10A
FIG. 10B
FIG. 10C

```
       K  V  K  K  R  K  E  I  *  L  Q  S  S  D  T  K  C
Hu   .AAAGTAAAAAAAAGAAAAGAAATCTAACTCCAGAGCTCTGACACAAAAT
       |  |  |  |  |||| || ||  |  |||  |       |||   |||
Ha    AGAGTAACCAGATAGAAGAGTAACCAGAGTTCTTAACCACTGAGCCATCT
       R  V  T  R  *  K  S  N  Q  S  S  *  P  L  S  H  L

L  R  C  Y  S  Q  *  E  K  R  D  V  N  L  *  V
Hu    GCCTTAGGTGTTATTCTCAATGAGAGAAAAGGGACGTGAATCTTTAAGTG
       |    |  ||| || |   ||         |      |  |   | ||
Ha    CTCCAGCTCCCTGTTTTTAACCATTAAATCTATTTATTTAATATCCATTT
       S  S  S  L  F  L  T  I  K  S  I  Y  L  I  S  I  Y

I  K  *  I  F  K  *  I  C  R  T  S  V  S  G  G  S
Hu    ATTAAGTGAATCTTTAAGTAAATCTGTCGTACTAGCGTTTCAGGCGGCTC
       ||| ||       |  ||| ||  |        |         |   | |
Ha    ATTTACTGTGATGTGTGGGACACGTGGAGGTTAGAGGACAACTTCTTGTT
       L  L  *  C  V  G  H  V  E  V  R  G  Q  L  L  V

N  T  T  R  P  R  L  R  R      N  G  E  N  V  R  M
Hu    AAACACCACACGCCCCCGACTACGGC...GGAATGGAGAGAATGTGCGCA
        ||  || |  |  ||  |  |||   ||   |  ||| |  |  ||| |
Ha    GCTTCTTTGTCTCCACCAAGTGAGTCCTTGAAGTCGACTAAGGGTCCTTA
       A  S  L  S  P  P  S  E  S  L  K  S  T  K  G  P  *

L  G  G  N  L  R  M  L  G  E  N  L  R  M  L  G
Hu    TGCTCGGCGGGAATCTGCGCATGCTCGGAGAGAATCTGCGCATGCTCGGC
       |    |   |  |  ||    |    ||||  ||||  |  |   |  |
Ha    AGACTTGATGACAAATGGCTTCACCGGTAAAGCCACTTCCCTGGTCCAGT
       D  L  M  T  N  G  F  T  G  K  A  T  S  L  V  Q  Y

R  N                L  R  E  L  G  G  N  L  R  K
Hu    CGGA...............ATCTGCGCGAGCTCGGCGGGAATCTGCGCAAG
       |              |   |  | || || |||           ||
Ha    ACTAGCGTTTTTTTGTTTTTTTTTAAGCAGTCTACGAGAACAAAGCCACA
       *  R  F  F  V  F  F  *  A  V  Y  E  N  K  A  T

L  G  G  N  L  R  M  L  R  V  P  G  H  G  F  P  A
Hu    CTCGGCGGGAATCTGCGCATGCTCAGAGTTCCGGGGCACGGTTTCCCCGC
       |  ||  |  |  |  ||||||||||  || |  |||||  ||||||||||
Ha    CCTGGGGAGGCTGTGCGCATGCTCACAGCCCAGGGGCCGGGTTTCCCCGC
       P  G  E  A  V  R  M  L  T  A  Q  G  P  G  F  P  A

FIG. IIA
```

```
     P  F  R  P  S  R  K  R  S  G  S  F  R  Y  L  P  L
Hu   CCCTTTCAGGCCTAGCAGGAAACGAAGCGGCTCTTTCCGCTATCTGCCGC
     ||||| |  ||  ||| ||||    ||                    ||
Ha   CCCTTGCCCGCAGAGCCGGAAGTCTAG................GTCTGT
     P  C  P  Q  S  R  K  S  R                    S  V

V  H  R  K  R  V  A  T  R  Q  V  P  A  R  K  K
Hu   TTGTCCACCGGAAGCGAGTTGCGACACGGCAGGTTCCCGCCCGGAAGAAG
     ||||   ||||||  ||||||  |||||   || || ||  || ||| |||
Ha   GTGTCGTCCGGAACTGAGTTGAGACACTATAGATTTCCATCC.GAAAAAG
     C  R  P  E  L  S  *  D  T  I  D  F  H  P  K  K

R  P  E  R  L  R  T  G  N  M
Hu   CGACCAGAGCGCCTGAGGACCGGCAACATG
     |||| |  |||| | ||||| |||||||||
Ha   TAACCAAACCGCCCGTGGACCAGCAACATG
     *  P  N  R  P  W  T  S  N  M
```

FIG. 11B

LEUCINE ZIPPER PROTEIN, KARP-1 AND METHODS OF REGULATING DNA DEPENDENT PROTEIN KINASE ACTIVITY

RELATED APPLICATIONS

This application claims priority under 35 USC § 119(e) from U.S. Provisional Patent Application Ser. No. 60/064, 557 filed on Oct. 17, 1997, entitled A NOVEL LEUCINE ZIPPER PROTEIN, KARP-1 AND METHODS OF REGULATING DNA DEPENDENT PROTEIN KINASE ACTIVITY. The content of the provisional application is hereby expressly incorporated by reference.

GOVERNMENT SUPPORT

The present invention was supported by a grant from the United States National Institutes of Health under grant/contract number R01 AI35763. The United States Government has certain rights in the invention.

FIELD OF THE INVENTION

The present invention pertains to nucleic acids encoding a novel leucine zipper protein, KARP-1, which is involved in DNA repair and polypeptides relating thereto. The present invention also includes fragments and biologically functional variants thereof. Also included are KARP-1 inhibitors which inhibit KARP-1 activity by inhibiting the expression or function of KARP-1. The invention further relates to methods of using such nucleic acids, polypeptides, and inhibitors in the treatment and/or diagnosis of disease, such as in a method for treating cancer in combination with a chemotherapeutic agent by administering a KARP-1 inhibitor to inhibit double strand DNA base repair.

BACKGROUND OF THE INVENTION

Although progress has been made in understanding the biological basis of and in treating cancer, it is believed that one-third of all people in the United States will ultimately develop cancer. The slow progress of understanding cancer and developing treatments for cancer is partly due to the broad variety of cancers as well as the heterogeneity of individual In spite of the diversity of cancers, many cancers share common features such as the abnormal expression or mutation of various genes, suggesting that a common mechanism may underlie many cancers. Mutations in the tumor suppressor gene p53 have been found in more than 50% of human cancers implying that loss of appropriate p53-dependent gene expression represents a fundamental step in oncogenic progression.

One tool commonly used for treating a wide variety of cancers is chemotherapy. More than 50 chemotherapeutic agents have been developed for the treatment of cancer. Included among chemotherapies for cancer is the use of combinational therapy, in which two or more chemotherapeutic agents having different mechanisms of action are given concurrently. The results typically can be additive. Not all tumors, however, respond to chemotherapeutic agents and others although initially responsive to chemotherapeutic agents may develop resistance to them. As a result, the search for effective anti-cancer drugs and drug combinations has intensified in an effort to find even more effective agents for treating the myriad of cancers.

Cancers are generally treated with either surgery, chemotherapy, including radiation, or a combination of these. Ionizing radiation therapy targets DNA by generating free radicals and reactive oxygen intermediates that damage local cellular substituents including DNA. Cells which undergo rapid proliferation are particularly sensitive to radiation therapy. Hypoxic tissues can be resistant to radiation therapy because the presence of oxygen is important to radiation.

DNA repair enzymes are critical to the normal function of a cell. DNA repair enzymes recognize the damage caused by genotoxic substances or by other causes (such as spontaneous damage or misreplication) and repair such damage. Defects in the ability of a cell to repair errors or breaks in DNA can be lethal to cells and can cause the development of serious diseases in the organism. DNA-dependent protein kinase (DNA-PK) is a serine-threonine protein kinase that requires the presence of double-stranded DNA with free ends for its activity and is composed of a Ku heterodimer consisting of 86 kDa (Ku86) and 70 kDa (Ku70) subunits (Reeves, 1985; Yaneva et al., 1985; Francoeur et al., 1986; Mimori et al., 1986) and a 465 kDa catalytic subunit (DNA-PK$_{CS}$) (Dvir et al., 1992; Gottlieb and Jackson, 1993; Suwa et al., 1994). Biochemical analyses of the Ku subunit of DNA-PK demonstrated that it bound in a sequence non-specific fashion to virtually all double-stranded DNA ends including 5'- or 3'-protruding ends, blunt ends (Mimori and Hardin, 1986), and duplex DNA ending in stem-loop structures (Falzon et al., 1993), apparently by recognizing transitions from double- to single-stranded DNA. Ku has also been reported to be capable of sequence-specific binding, particularly within the promoter elements of genes (Giffin et al., 1996). Recently, extensive genetic and molecular analyses have identified DNA-PK as an integral component of the DNA double-strand break (DSB) repair pathway (reviewed in Jeggo et al., 1995; Jackson, 1996).

In mammals, defects in DNA DSB repair manifest themselves in two easily recognizable phenotypes: ionizing radiation (IR$^S$) hypersensitivity and immunodeficiency. These two seemingly unrelated biological processes are in fact linked by the requirement of DNA DSBs as reaction intermediates. Thus, the exposure of mammalian cells to IR induces lesions in chromosomal DNA such as strand scissions, single-stranded breaks, DSBs and base cross-links (Price, 1993). In particular, DNA DSBs appear to be the predominant cytotoxic lesions as even a single unrepaired DNA DSB can be a lethal event (Klar et al., 1984; Frankenberg-Schwager and Frankenberg, 1990). Mammalian IR-sensitive (IRS) mutants have been isolated and in approximately half of these cell lines, IR sensitivity correlated with a greatly decreased ability to repair DNA DSBs (reviewed in Zdzienicka, 1995). Thus, the DSB repair capacity of a cell appears to be a critical, though not the sole, factor in determining cellular IR-sensitivity. Similarly, the development of the mammalian immune system is dependent upon a site-specific DNA recombination process, termed lymphoid V(D)J recombination, that assembles the non-contiguous genomic segments that encode the Variable (V), Diversity (D), and Joining (J) elements of immunoglobulin and T-cell receptor genes (reviewed in Lewis, 1994). Importantly, analyses of V(D)J recombination products in vivo and in vitro has proven that DNA DSBs are an essential intermediate in the V(D)J reaction mechanism (reviewed in Oettinger, 1996). Thus, the repair of DNA DSBs is an integral feature of IR sensitivity and V(D)J recombination.

Mutations in the subunits of DNA-PK have been shown to affect deleteriously both IR sensitivity and V(D)J recombination. DNA-PK$_{CS}$ is now known to be the product of the severe combined immune deficiency (scid) gene (Blunt et al., 1995; Hartley et al., 1995; Kirchgessner et al., 1995;

Lees-Miller et al., 1995; Danska et al., 1996) and it has long been recognized that animals homozygously defective at this locus were profoundly immune deficient (Bosma et al., 1983), IR$^S$ (Fulop and Phillips, 1990) and defective in DNA DSB repair (Biedermann et al., 1991; Hendrickson et al., 1991). Recently, it was shown that cell lines belonging to the fifth X-ray cross-complementation group (XRCC5) (Thompson and Jeggo, 1995; Zdzienicka, 1995), which were known to be IR$^S$ and V(D)J-defective, were deficient in Ku86 gene expression (Smider et al., 1994; Taccioli et al., 1994; Boubnov et al., 1995; Errami et al., 1996; He et al., 1996). Lastly, knock-out mice for Ku86 have been generated by homologous recombination (Nussenzweig et al., 1996; Zhu et al., 1996) and, as expected, these mice have a profound immune deficiency and are IR$^S$. Thus, DNA-PK is an important mammalian DNA repair complex and mutations in either DNA-PK$_{CS}$ or the 86 kDa subunit of Ku result in severe IR$^S$ and V(D)J recombination deficits due to impaired DNA DSB repair.

SUMMARY OF THE INVENTION

The invention provides isolated nucleic acid molecules, unique fragments of those molecules, expression vectors containing the foregoing, and host cells transfected with those molecules. The invention also provides isolated polypeptides and inhibitors of the foregoing nucleic acids and polypeptides which prevent double strand DNA base repair. The foregoing can be used in the diagnosis or treatment of conditions characterized by the loss of KARP-1 activity and can be used in methods in which it is therapeutically useful to inhibit KARP-1 activity such as a treatment for cancer. Here, we present the identification of KARP-1, which plays a role in double strand DNA base repair.

It was discovered according to the invention that the Ku86 locus encodes a second gene termed (Ku86 Autoantigen Related Protein-1) KARP-1. KARP-1 is a protein which extends at least an additional 88 amino acids beyond the Ku86 ATG site and includes at least two structurally important regions, a basic region and a leucine zipper domain. It is believed that the KARP-1 gene product is capable of modulating the activity of DNA-PK by interacting with one or more of the subunits of the DNA-PK complex. The leucine zipper of KARP-1 is similar to that of DNA-PK$_{cs}$ and potentially could modulate the activity of the DNA-PK by binding to DNA-PK$_{cs}$.

The invention encompasses in one aspect a KARP-1 nucleic acid molecule which hybridizes under stringent conditions to a molecule consisting of the nucleic acid sequence of SEQ. ID. NO: 1 and/or SEQ. ID. NO: 35, and which codes for a polypeptide which has KARP-1 activity. The KARP-1 nucleic acid molecule in one embodiment is the nucleic acid sequence of SEQ. ID. NO: 1 and/or SEQ. ID. NO: 35. In another embodiment the KARP-1 nucleic acid is a homolog or allele of the nucleic acid sequence of SEQ. ID. NO: 1 and/or SEQ. ID. NO: 35.

According to another aspect of the invention a KARP-1 nucleic acid molecule which is a unique fragment of SEQ. ID. NO: 1 and/or SEQ. ID. NO: 35 is provided. In one embodiment the unique fragment excludes sequences consisting of only SEQ ID NO:3. In another embodiment the unique fragment includes at least one sequence encoding a leucine zipper domain of SEQ ID NO:4. In yet another embodiment the unique fragment includes at least 10 bases of a p53 binding sequence of SEQ ID NO:30. In a preferred embodiment the nucleic acid molecule consists of at least 14, 15, 16, 17, 18, 19, 20, 21, or 22 contiguous nucleotides.

In another embodiment the nucleic acid molecule consists of between 12 and 32 contiguous nucleotides.

In another aspect the invention is an expression vector comprising the KARP-1 nucleic acid molecule operably linked to a promoter. Also included within the invention is a host cell transformed or transfected with the expression vector.

According to another aspect, the invention is a KARP-1 polypeptide encoded by the KARP-1 nucleic acid molecule. In one embodiment the polypeptide is the amino acid sequence of SEQ ID NO:2. In another embodiment the KARP-1 polypeptide is a functional fragment or variant thereof of SEQ ID NO:2. Preferably the polypeptide has the amino acid sequence of SEQ ID NO:4. Polypeptides which bind selectively to the KARP-1 polypeptide are also encompassed by the invention.

According to another aspect of the invention a composition is provided. The composition includes a KARP-1 polypeptide having the following leucine zipper amino acid sequence

LGX$_1$NLRX$_2$ wherein X$_1$ is selected from the group of amino acids consisting of G, R, and E and wherein X$_2$ is selected from the group of amino acids consisting of M, E, and K. Preferably the KARP-1 polypeptide has at least two leucine zipper amino acid sequences in tandem. In another preferred embodiment the KARP-1 polypeptide has at least five leucine zipper amino acid sequences in tandem.

Surprisingly, it was found that inhibitors of KARP-1 are useful for promoting cell death of rapidly dividing cells by interfering with the repair of double stranded DNA. Rapidly dividing cells, such as cancer cells, undergoing DNA replication are more likely to undergo DNA damage which requires repair than cells which are dividing slowly or not at all. Ordinarily the damaged DNA is repaired by DNA-PK. When a KARP-1 inhibitor is added to the cell the activity of DNA-PK is inhibited and the damaged double strand DNA is not repaired, ultimately, leading to cell death. The KARP-1 inhibitors can be administered in conjunction with chemotherapeutic agents as an adjunct therapy so that the amount of chemotherapeutic agent used can be reduced. In particular, KARP-1 inhibitors are useful in conjunction with compounds which induce double strand DNA base damage such as ionizing radiation.

According to one aspect of the invention a KARP-1 inhibitor is provided. The KARP-1 inhibitor is an agent that inhibits KARP-1 activity. In one embodiment the agent is an antisense KARP-1 nucleic acid. In another embodiment the agent is a KARP-1 binding peptide. In a preferred embodiment the KARP-1 binding peptide is selected from the group consisting of an antibody and an antibody fragment selected from the group consisting of a Fab fragment, a F(ab)$_2$ fragment and a fragment including a CDR3 region. In another embodiment the agent is a dominant negative KARP-1 polypeptide.

The invention also encompasses a composition including the KARP-1 inhibitor and a pharmaceutically acceptable carrier.

In another aspect of the invention a method for inhibiting KARP-1 activity in a mammalian cell is provided. The method involves the step of contacting the mammalian cell with an amount of the KARP-1 inhibitor effective to inhibit double stranded DNA base repair by DNA-PK in the mammalian cell.

In another aspect the invention is a method for modulating the proliferation of a cancer cell. The method includes the steps of contacting the cancer cell with an amount of the KARP-1 inhibitor effective to inhibit double stranded DNA base repair in the cancer cell and contacting the cancer cell with an amount of chemotherapeutic agent effective to inhibit the proliferation of the cancer cell when double strand DNA base repair is inhibited.

In another aspect of the invention a method for treating a subject having a cancer sensitive to treatment with a combination of a chemotherapeutic agent and a KARP-1 inhibitor is provided. The method involves the step of administering to a subject in need of such treatment the chemotherapeutic agent and the KARP-1 inhibitor in a combined amount effective to inhibit growth of the cancer, said combined amount being an amount of chemotherapeutic agent and an amount of KARP-1 inhibitor, wherein the amount of KARP-1 inhibitor is effective to prevent double strand DNA base repair and the amount of chemotherapeutic agent is effective to prevent the proliferation of the cancer cell when the double strand DNA base repair is inhibited. In one embodiment the chemotherapeutic agent is a DNA-damaging agent. Preferably the DNA-damaging agent is ionizing radiation.

According to another aspect the invention is a method for treating a subject having a cancer that is resistant to DNA-damaging chemotherapy. The method includes the steps of administering to the subject an amount of a chemotherapeutic agent, and administering substantially simultaneously therewith an amount of a KARP-1 inhibitor, wherein said amounts when administered are effective for inhibiting growth of the cancer.

In one embodiment of the above methods the KARP-1 inhibitor is an antisense KARP-1 nucleic acid. In another embodiment the KARP-1 inhibitor is a dominant negative KARP-1 polypeptide. In yet another embodiment the agent is a KARP-1 binding peptide.

In one aspect of the invention KARP-1 nucleic acids and polypeptides of the invention are useful for increasing KARP-1 in a cell. Increasing KARP-1 in a cell which has a defect in endogenous Ku86 or KARP-1 results in improved double strand DNA base repair. For instance defects in Ku86 have been demonstrated to cause immune deficiency, which is believed to be due to the inability of the DNA-PK to properly repair double strand DNA defects which occur during the V(D)J joining process. Cells deficient in Ku86 gene expression such as XRCC5 are known to be both IR$^S$ and V(D)J defective. Additionally mice which have the Ku86 gene knocked out are also both IR$^S$ and V(D)J defective.

In one aspect of the invention a method for increasing KARP-1 expression in a subject is provided. The method involves the step of administering to a subject in need of such treatment a molecule selected from the group consisting of a KARP-1 nucleic acid and a KARP-1 polypeptide in an amount effective to increase KARP-1 expression in the cell. In one embodiment the molecule is a KARP-1 nucleic acid operably linked to a promoter. In another embodiment the molecule is a KARP-1 polypeptide.

According to another aspect of the invention a method for treating a subject having an immune deficient disorder is provided. The method involves the step of administering to the subject an amount of a molecule selected from the group consisting of a KARP-1 nucleic acid and a KARP-1 polypeptide.

Each of the limitations of the invention can encompass various embodiments of the invention. It is, therefore, anticipated that each of the limitations of the invention involving any one element or combinations of elements can be included in each aspect of the invention. These and other aspects of the invention are described in greater detail below.

BRIEF DESCRIPTION OF THE DRAWINGS

FIG. 1 shows the KARP-1 open reading frame (ORF) as it exists in the genomic DNA upstream of the human Ku86 gene, with lower-case letters corresponding to intronic DNA, upper-case letters corresponding to KARP-1 exon DNA and the bold, upper-case letters corresponding to the Ku86 gene. The leucine residues in the hexaheptad repeat are shown by a bold asterisk (*) while the leucine residues in the penta-heptad repeat are shown by a normal asterisk (*). Basic amino acids in the flanking domain are marked with a plus (+). A putative nuclear localization signal is shown by the horizontal line.

FIG. 2A is a helical wheel diagram of the leucine repeat within the N-terminus of KARP-1, in which the lower-case letters correspond to the seven positions within the α-helix.

FIG. 2B shows a sequence comparing and demonstrating that KARP-1 has homology to the Hin lintegrase. A consensus sequence is shown below with identical residues in upper-case and conserved residues demarcated by an asterisk (*).

FIG. 2C shows a sequence comparing the hexaheptad repeat of leucines from KARP-1 and DNA-PK$_{CS}$, in which the identical residues are shown with a vertical line and conserved residues are demarcated by an asterisk (*)

FIGS. 3A and 3B show Northern and Southern blot data indicating that the KARP-1 ORF is expressed. FIG. 3A is a Northern blot of poly(A)$^+$ mRNA (10 μg) from HCW2 and Sc5 probed with 328 bp fragment corresponding to the leucine (L) repeat and basic (+) region of KARP-1 which demonstrates that the KARP-1 ORF is expressed. FIG. 3B is an ethidium bromide stained gel of PCR products from a tissue-specific library and the corresponding Southern blot probed with a 835 bp β-actin probe and the 328 bp KARP-1 specific probe which demonstrates that KARP-1 is ubiquitously expressed at low levels.

FIG. 5 shows the predicted amino acid sequence of KARP-1 based upon 5'-RACE and 3'-RACE products in which the two bold methionines (M) correspond to the putative initiator methionines for KARP-1 and Ku86, respectively and the amino acids in lower-case at residues 102, 243, 650, 725 and 746 represent amino acid differences from the published human Ku86 sequence.

FIGS. 8A and 8C show DNA-PK activity in whole-cell extracts prepared from HCW-2 and Sc5 (A) or HeLa and Sc2 (C) subclones, which indicate that DNA-PK activity is reduced in dominant-negative subclones. FIGS. 8B and D show that X-ray survival in the same cellular extracts is reduced in dominant-negative subclones.

FIGS. 10A–10C show a southern blot analysis of a commercial Zoo blot probed under low-stringency conditions using first a probe specific for the leucine repeat of KARP-1 (10A) and then Ku86 (10C) which suggests that the leucine repeat region of KARP-1 is primate-specific. The position of fragments which appear to represent specific hybridization to the probes are indicated by asterisks (*). In addition, an ethidium bromide (EtBr) staining profile provided by the manufacturer is shown (10B). The names on the top of pictures represent the species from which the genomic DNA used for the zoo blot was derived.

FIGS. 11A and 11B shows a comparison of the KARP-1 sequence in humans (Hu) and hamsters (Ha) and demonstrates that the sequence is not conserved in hamsters. Horizontal lines indicate identities and the dots represent gaps introduced into the sequences to obtain an optimal alignment. The bold sequences indicate the initiator ATGs for Ku86 and KARP-1. The predicted amino acid sequence is shown either above (human) or below (hamster) the DNA sequence and asterisks (*) indicate stop codons.

FIG. 13A shows RT-PCR reactions on HCT1 16 cells which were X-irradiated (10 Gy). FIG. 13B shows the fold-induction of KARP-1 mRNA which was quantitated using β-actin levels as a reference. The average of two independent experiments is shown and the error bars represent the standard deviation. FIG. (13C) shows RT-PCR reactions on HCT116 cells which were X-irradiated at the indicated doses and at 90 min post-irradiated RT-PCR reactions followed by Southern hybridizations. For the β-actin sample only the EtBr-stained gel is shown. The fold-induction of KARP-1 mRNA was quantitated using β-actin levels as a reference (1 3D).

In FIG. 14A HCW-2 (p53$^{-/-}$) and 14B HeLa (p53-defective) cell lines were X-irradiated at the indicated doses and at 90 min post-irradiation RT-PCR reactions (β-actin) followed by Southern hybridizations (KARP-1). In FIG. 14C GM08436A (ATM$^{-/-}$), 14D GM01526E (ATM$^{-/-}$) and 14E GM00130C (ATM$^{+/+}$) cells (ATM$^{-/-}$cell lines, GM08436A and GM01526E, and the ATM$^{+/+}$ cell line, GM00130C, were purchased from NIGMS Human Genetic Mutant Cell Repository at the Coriell Institute for Medical Research) were X-irradiated at 10 Gy and at the indicated times post-irradiation RT-PCR reactions (β-actin) followed by Southern hybridizations (KARP-1).

BRIEF DESCRIPTION OF THE SEQUENCES

Figure 3B:
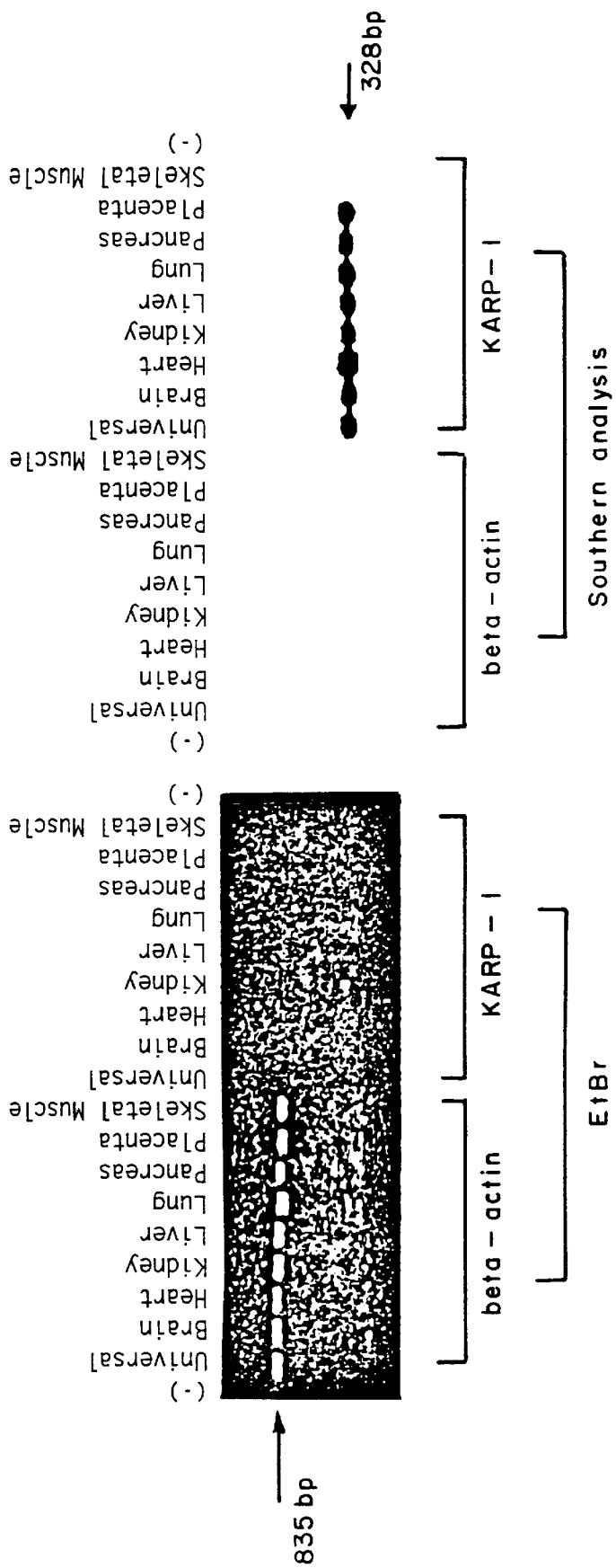

SEQ ID NO:1 is the nucleotide sequence of the human KARP-1 genomic DNA.

SEQ ID NO:2 is the amino acid sequence of the human KARP-1 polypeptide.

SEQ ID NO:3 is the nucleotide sequence of the coding region of Ku86 (Prior art).

SEQ ID NO:4 is the amino acid sequence of the leucine repeat domain of the human KARP-1 polypetide.

SEQ ID NO:5 is the nucleotide sequence of the coding region of Hin (Prior art).

SEQ ID NO:6 is the nucleotide sequence of the coding region of DNA-PKcs (Prior art).

SEQ ID NO:7 is the nucleotide sequence of a primer for Ming5.

SEQ ID NO:8 is the nucleotide sequence of a p rimer for AP-1 (Prior art).

SEQ ID NO:9 is the nucleotide sequence of a primer for Ming4.

SEQ ID NO:10 is the nucleotide sequence of a primer for AP-2 (Prior art).

SEQ ID NO:11 is the nucleotide sequence of a primer for Ming14.

SEQ ID NO:12 is the nucleotide sequence of a primer for Ming15.

SEQ ID NO:13 is the nucleotide sequence of a primer for KJ10.

SEQ ID NO:14 is the nucleotide sequence of a primer for Ming1.

SEQ ID NO:15 is the nucleotide sequence of a primer for AP-1 (Prior art).

SEQ ID NO:16 is the nucleotide sequence of a primer for AP-2 (Prior art).

SEQ ID NO:17 is the nucleotide sequence of a primer for KJ1011.

SEQ ID NO:18 is the nucleotide sequence of a primer for KJ15.

SEQ ID NO:19 is the nucleotide sequence of a primer for KJ13.

SEQ ID NO:20 is the nucleotide sequence of a primer for LZ5E.

SEQ ID NO:21 is the nucleotide sequence of a primer for KJ007.

SEQ ID NO:22 is the nucleotide sequence of a primer for KJ008.

SEQ ID NO:23 is the nucleotide sequence of a primer for KJ003.

SEQ ID NO:24 is the nucleotide sequence of a primer for 86-7 (Prior art).

SEQ ID NO:25 is the amino acid sequence of a KARP-1 specific peptide used for generating anti-KARP-1 antibodies.

SEQ ID NO:26 is the nucleotide sequence of a primer for FP (Prior art).

SEQ ID NO:27 is the nucleotide sequence of a primer for SEL86-2 (Prior art).

SEQ ID NO:28 is the nucleotide sequence of a primer for SEL86-1 (Prior art).

SEQ ID NO:29 is the consensus nucleotide sequence of a p53 binding site (Prior art).

SEQ ID NO:30 is the nucleotide sequence of the KARP-1 p53 binding site.

SEQ ID NO:31 is the nucleotide sequence of a primer for β-actin (Prior art).

SEQ ID NO:32 is the nucleotide sequence of a primer for β-actin (Prior art).

SEQ ID NO:33 is the nucleotide sequence of a primer for Ku86 (Prior art).

SEQ ID NO:34 is the nucleotide sequence of a primer for Ku86 (Prior art).

SEQ ID NO:35 is the nucleotide sequence of the human KARP-1 cDNA.

DETAILED DESCRIPTION

The present invention in one aspect involves the cloning of a cDNA encoding KARP-1. The sequence of the human gene is presented as SEQ ID NO:1, and the predicted amino acid sequence of this gene's protein product is presented as SEQ ID NO:2. KARP-1 was identified, very unexpectedly, as an open reading frame (ORF) upstream of Ku86 that was unusual for four reasons. First, the ORF was in-frame and contiguous with Ku86 and extended at least an additional 88 amino acids beyond the Ku86 ATG (FIG. 1), whereas stop codons are usually found upstream of the initiator ATG for most mammalian genes (Kozak, 1987). Secondly, in the few cases where long ORFs in the 5'-untranslated region (UTR) of genes have been described they usually do not encode additional potential initiator methionine residues (Kozak, 1991; Xiong et al., 1991). The Ku86 5'-UTR ORF, however, encoded several in-frame methionines (FIG. 1). Thirdly, the Ku86 5'-UTR ORF contained an extremely basic region in which 15 of 37 residues were either lysines or arginines, including a potential nuclear localization signal (Kalderon et al., 1984). Lastly, the Ku86 5'-UTR ORF also had the capacity to encode a novel leucine repeat which consisted of a perfect hexaheptad repeat of leucine residues interdigitated with a perfect penta-heptad repeat of leucines (FIGS. 1 and 2A). Heptad repeats of leucines are characteristic of a subset of coiled-coil proteins known as leucine zippers. These proteins have a characteristic seven-residue repeat, $(a \cdot b \cdot c \cdot d \cdot e \cdot f \cdot g)_n$, in which a leucine residue is found at all or most of the 'd' positions and hydrophobic residues are found at the 'a' positions. (Landschulz et al., 1988; reviewed in Hurst, 1994). The leucine repeats observed in the Ku86 5'-UTR ORF conformed to this pattern (FIG. 2A).

Analysis of the ORF sequence by comparison to nucleic acid and protein databases determined that the KARP-1 leucine repeat sequence had weak homology (20% identity and 40% similarity) to the Hin integrase (FIG. 2B). Recently, it has been shown that the RAG-1 gene (Schatz et al., 1989), which is absolutely required for V(D)J recombination (Mombaerts et al., 1992) also has functional homology to the Hin integrase and that the recombination signal sequences which mediate V(D)J recombination resemble the Hin recombination site (Spanopoulou et al., 1996; reviewed by Lewis and Wu, 1997). Secondly, heptad repeats of A leucines are a motif found in protein interaction domains and over 80 such domains have been identified (Hurst, 1994). Most heptad repeats of leucines, however, are only four, or occasionally five, leucines long and a perfect hexa-heptad repeat appears, to our knowledge, to have been reported only once previously in the literature. Intriguingly, the protein with a perfect hexa-heptad repeat of leucines is DNA-PK$_{CS}$ (FIG. 2C; Hartley et al., 1995), the protein with which Ku86 is known to interact (Dvir et al., 1992; Gottlieb and Jackson, 1993; Suwa et al., 1994).

The invention thus involves in one aspect KARP-1 nucleic acids and KARP-1 polypeptides, as well as therapeutics relating thereto. The invention also embraces isolated functionally equivalent variants, useful analogs and fragments of the foregoing nucleic acids; polypeptides and peptides coded for by any of the foregoing nucleic acids; and complements of the foregoing nucleic acids.

The KARP-1 nucleic acids and polypeptides of the invention are isolated. The term "isolated", as used herein in reference to a nucleic acid molecule, means a nucleic acid sequence: (i) amplified in vitro by, for example, polymerase chain reaction (PCR); (ii) synthesized by, for example, chemical synthesis; (iii) recombinatly produced by cloning; or (iv) purified, as by cleavage and gel separation. The term "isolated", as used herein in reference to a polypetide, means a polypeptide encoded by an isolated nucleic acid sequence, as well as polypeptides synthesized by, for example, chemical synthetic methods, and polypeptides separated from biological materials, and then purified using conventional protein analytical procedures.

As used herein a KARP-1 nucleic acid refers to an isolated nucleic acid molecule which: (1) hybridizes under stringent conditions to a nucleic acid having the sequence of SEQ. ID. NO: 1 and/or SEQ. ID. NO: 35 and (2) which codes for a polypeptide which has KARP-1 activity. The preferred KARP-1 nucleic acid has the nucleic acid sequence of SEQ. ID NO. 1. The KARP-1 nucleic acids of the invention also include homologs and alleles of a nucleic acid having the sequence of SEQ. ID. NO:1, as well as functionally equivalent variants, analogs and fragments of the foregoing nucleic acids. "Functionally equivalent", in reference to a KARP-1 nucleic acid variant, analog or fragment, refers to a nucleic acid that codes for a KARP-1 polypeptide that has KARP-1 activity. KARP-1 nucleic acids further embrace nucleic acid molecules which code for the KARP-1 polypeptide having the sequence of SEQ. ID NO:2 but which differ from the sequence of SEQ. ID. NO:

1 in codon sequence due to the degeneracy of the genetic code. The invention further embraces unique fragments (which may, or may not be "functional" with respect to encoding a KARP-1 polypetide) and complements of the foregoing nucleic acids. Such unique fragments can be used, for example, as probes in hybridization assays and as primers in a polymerase chain reaction (PCR).

As used herein "KARP-1 activity" refers to an ability of a molecule to modulate double strand DNA base repair. A molecule which inhibits KARP-1 activity is one which inhibits double strand DNA base repair and a molecule which increases KARP-1 activity is one which increases double strand DNA base repair. Changes in double strand DNA base repair can be measured by changes in DNA-PK activity by in vitro assays such as the one disclosed herein.

Homologs and alleles of the KARP-1 nucleic acids of the invention can be identified by conventional techniques. For example, homologs of human KARP-1 can be isolated by hybridizing a probe derived from SEQ. ID. NO: 1 and/or SEQ. ID. NO: 35 under stringent conditions with a cDNA library of another species and selecting positive clones. Thus, an aspect of the invention is those nucleic acid sequences which code for KARP-1 polypeptides and which hybridize to a nucleic acid molecule consisting of SEQ. ID. NO: 1 and/or SEQ. ID. NO: 35 under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5× SSC, 0.02% Ficoll, 0.02% polyvinyl pyrrolidone, 0.02% Bovine Serum Albumin, 2.5 mM NaH$_2$PO$_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2× SSC at room temperature and then at 0.1× SSC/0.1× SDS at temperatures up to 65° C.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of KARP-1 nucleic acids of the invention. The skilled artisan also is familiar with the methodology for screening cells and libraries for expression of such molecules which then are routinely isolated, followed by isolation of the pertinent nucleic acid molecule and sequencing.

In general, homologs and alleles typically will share at least 40% nucleotide identity to SEQ. ID. NO: 1 and/or SEQ. ID. NO: 35, in some instances will share at least 50% nucleotide identity and in still other instances will share at least 60% nucleotide identity. Watson-Crick complements of the foregoing nucleic acids also are embraced by the invention.

In screening for KARP-1 nucleic acids, a Southern blot may be performed using the foregoing stringent conditions, together with a radioactive probe. After washing the membrane to which the DNA is finally transferred, the membrane can be placed against X-ray film to detect the radioactive signal.

The KARP-1 nucelic acids of the invention also include degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating KARP-1 polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ. ID. NO: 1 and/or SEQ. ID. NO: 35. A unique fragment is one that is a 'signature' for the larger nucleic acid. It, for example, is long enough to assure that its precise sequence is not found in molecules outside of the KARP-1 nucleic acids defined above. Unique fragments can be used as probes in Southern blot assays to identify such nucleic acids, or can be used in amplification assays such as those employing PCR. As known to those skilled in the art, large probes such as 200 nucleotides or more are preferred for certain uses such as Southern blots, while smaller fragments will be preferred for uses such as PCR. Unique fragments also can be used to produce fusion proteins for generating antibodies or determining binding of the polypeptide fragments. Likewise, unique fragments can be employed to produce non-fused fragments of the KARP-1 polypeptides, useful, for example, in the preparation of antibodies, in immunoassays, and as a competitive binding partner of subunits of the DNA-PK complex and/or other polypeptides which bind to the KARP-1 polypeptides, for example, in therapeutic applications. Unique fragments further can be used as antisense molecules to inhibit the expression of KARP-1 nucleic acids and polypeptides, particularly for therapeutic purposes as described in greater detail below.

As will be recognized by those skilled in the art, the size of the unique fragment will depend upon its conservancy in the genetic code. Thus, some regions of SEQ. ID. NO: 1 and/or SEQ. ID. NO: 35 will require longer segments to be unique while others will require only short segments, typically between 12 and 32 nucleotides (e.g. 12, 13, 14, 15, 16, 17, 18, 19, 20, 21, 22, 23, 24, 25, 26, 27, 28, 29, 30, 31 and 32 bases long). Virtually any segment of SEQ. ID. NO: 1 and/or SEQ. ID. NO: 35 that is 18 or more nucleotides in length will be unique. Unique fragments, however, exclude fragments completely composed of the nucleotide sequence of SEQ ID NO:3 (encoding the Ku86 polypeptide) which overlaps SEQ. ID. NO: 1 and/or SEQ. ID. NO: 35. A fragment which is completely composed of the sequence of SEQ ID NO:3 is one which does not include any of the nucleotides unique to KARP-1. Alternatively, unique fragments include at least one sequence encoding a leucine zipper repeat of SEQ ID NO:4 (leucine zipper domain of KARP-1). Particularly preferred are those unique fragments drawn from a portion of SEQ ID NO:4. Also preferred are those nucleic acid segments which are involved in binding to p53 and shown in SEQ ID NO:30 and FIG. 6B. Those skilled in the art are well versed in methods for selecting such sequences, typically on the basis of the ability of the unique fragment to selectively distinguish the sequence of interest from non-KARP-1 nucleic acids. A comparison of the sequence of the fragment to those on known databases typically is all that is necessary, although in vitro confirmatory hybridization and sequencing analysis may be performed.

The KARP-1 nucleic acid, in one embodiment, is operably linked to a gene expression sequence which directs the expression of the KARP-1 nucleic acid within a eukaryotic cell. The "gene expression sequence" is any regulatory nucleotide sequence, such as a promoter sequence or promoter-enhancer combination, which facilitates the efficient transcription and translation of the KARP-1 nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined KARP-1 nucleic acid. The gene expression sequences optionally includes enhancer sequences or upstream activator sequences as desired.

The KARP-1 nucleic acid sequence and the gene expression sequence are said to be "operably linked" when they are covalently linked in such a way as to place the transcription and/or translation of the KARP-1 coding sequence under the influence or control of the gene expression sequence. If it is desired that the KARP-1 sequence be translated into a functional protein, two DNA sequences are said to be operably linked if induction of a promoter in the 5' gene expression sequence results in the transcription of the KARP-1 sequence and if the nature of the linkage between the two DNA sequences does not (1) result in the introduction of a frame-shift mutation, (2) interfere with the ability of the promoter region to direct the transcription of the KARP-1 sequence, or (3) interfere with the ability of the corresponding RNA transcript to be translated into a protein. Thus, a gene expression sequence would be operably linked to a KARP-1 nucleic acid sequence if the gene expression sequence were capable of effecting transcription of that KARP-1 nucleic acid sequence such that the resulting transcript might be translated into the desired protein or polypeptide.

The KARP-1 nucleic acid and the KARP-1 polypeptide (including the KARP-1 inhibitors described below) of the invention can be delivered to the eukaryotic cell alone or in association with a vector. In its broadest sense, a "vector" is any vehicle capable of facilitating: (1) delivery of a KARP-1 nucleic acid or polypeptide to a target cell or (2) uptake of a KARP-1 nucleic acid or polypeptide by a target cell. Preferably, the vectors transport the KARP-1 nucleic acid or polypeptide into the target cell with reduced degradation relative to the extent of degradation that would result in the absence of the vector. Optionally, a "targeting ligand" can be attached to the vector to selectively deliver the vector to a cell which expresses on its surface the cognate receptor for the targeting ligand. In this manner, the vector (containing a KARP-1 nucleic acid or a KARP-1 polypeptide) can be selectively delivered to a specific. In general, the vectors useful in the invention are divided into two classes: biological vectors and chemical/physical vectors. Biological vectors are useful for delivery/uptake of KARP-1 nucleic acids to/by a target cell. Chemical/physical vectors are useful for delivery/uptake of KARP-1 nucleic acids or KARP-1 proteins to/by a target cell.

Biological vectors include, but are not limited to, plasmids, phagemids, viruses, other vehicles derived from viral or bacterial sources that have been manipulated by the insertion or incorporation of the nucleic acid sequences of the invention, and free nucleic acid fragments which can be attached to the nucleic acid sequences of the invention. Viral vectors are a preferred type of biological vector and include, but are not limited to, nucleic acid sequences from the following viruses: retrovirus, such as moloney murine leukemia virus; harvey murine sarcoma virus; murine mammary tumor virus; rouse sarcoma virus; adenovirus; adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M, "*Gene Transfer and Expression, A Laboratory Manual*," W. H. Freeman C.O., New York (1990) and Murry, E.J. Ed. "*Methods in Molecular Biology*," vol. 7, Humana Press, Inc., Cliffton, N.J. (1991). Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a KARP-1 polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.PIA recombinant is disclosed by Wamier et al., in intradermal injection in mice for immunization against P1A (*Int. J Cancer,* 67:303–310, 1996).

Another preferred virus for certain applications is the adeno-associated virus, a double-stranded DNA virus. The adeno-associated virus can be engineered to be replication-deficient and is capable of infecting a wide range of cell types and species. It further has advantages, such as heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In addition to the biological vectors, chemical/physical vectors may be used to deliver a KARP-1 nucleic acid or polypeptide to a target cell and facilitate uptake thereby. As used herein, a "chemical/physical vector" refers to a natural or synthetic molecule, other than those derived from bacteriological or viral sources, capable of delivering the isolated KARP-1 nucleic acid or polypeptide to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2–4.0μ can encapsulate large macromolecules. RNA, DNA, and intact virions can be encapsulated within the aqueous interior and be delivered to cells in a biologically active form (Fraley, et al., *Trends Biochem. Sci,* v. 6, p. 77 (1981)). In order for a liposome to be an efficient nucleic acid transfer vector, one or more of the following characteristics should be present: (1) encapsulation of the nucleic acid of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue by coupling the liposome to a specific ligand such as a monoclonal antibody, sugar, glycolipid, or protein. Ligands which may be useful for targeting a liposome to a particular cell will depend on the particular cell or tissue type. Additionally when the vector encapsulates a nucleic acid, the vector may be coupled to a nuclear targeting peptide, which will direct the KARP-1 nucleic acid to the nucleus of the host cell.

Liposomes are commercially available from Gibco BRL, for example, as LIPOFECTIN™ and LIPOFECTACE™, which are formed of cationic lipids such as N-[1-(2, 3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology,* V. 3, p. 235–241 (1985).

In one particular embodiment, the preferred vehicle is a biocompatible micro particle or implant that is suitable for implantation into the mammalian recipient. Exemplary bioerodible implants that are useful in accordance with this method have been described extensively for the release of polypeptides. Implants for release of nucleic acids have also been described, e.g., in PCT International application no. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing an exogenous gene under the control of an appropriate promotor. The polymeric matrix is used to achieve sustained release of the exogenous gene in the patient. In accordance with the instant invention, the KARP-1 nucleic acids described herein are encapsulated or dispersed within a biocompatible, preferably biodegradable polymeric matrix such as the one disclosed in PCT/US/03307. The polymeric matrix preferably is in the form of a microparticle such as a microsphere (wherein the KARP-1 nucleic acid is dispersed throughout a solid polymeric matrix) or a microcapsule (wherein the KARP-1 nucleic acid is stored in the core of a polymeric shell). Other forms of the polymeric matrix for containing the KARP-1 nucleic acid or polypeptide include films, coatings, gels, implants, and stents.

The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer. The matrix composition also can be selected not to degrade, but rather, to release by diffusion over an extended period of time.

Both non-biodegradable and biodegradable polymeric matrices can be used to deliver the KARP-1 nucleic acids or polypeptides of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the KARP-1 nucleic acids or polypeptides of the invention are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly (ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly (butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in macromolecules, 1993, 26, 581–587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly (isobutyl methacrylate), poly(hexylmethacrylate), poly (isodecyl methacrylate), poly(lauryl methacrylate), poly (phenyl methacrylate), poly(methyl acrylate), poly (isopropyl acrylate), poly(isobutyl acrylate), and poly (octadecyl acrylate).

Compaction agents also can be used alone, or in combination with, a biological or chemical/physical vector of the invention to deliver the KARP-1 nucleic acid. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver the isolated KARP-1 nucleic acid in a form that is more efficiently taken up by the cell or, more preferably, in combination with one or more of the above-described vectors.

Other exemplary compositions that can be used to facilitate uptake by a target cell of the KARP-1 nucleic acids include calcium phosphate and other chemical mediators of intracellular transport, microinjection compositions, electroporation and homologous recombination compositions (e.g., for integrating a KARP-1 nucleic acid into a preselected location within the target cell chromosome).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the KARP-1 cDNA sequences in expression vectors, as well as to transfect host cells and cell lines, be these prokaryotic (e.g., E. coli), or eukaryotic (e.g., COS cells, yeast expression systems and recombinant baculovirus expression in insect cells). Especially useful are mammalian cells such as human, pig, goat, primate, etc. They may be of a wide variety of tissue types, and include primary cells and cell lines. Specific examples include keratinocytes, peripheral blood leukocytes, bone marrow stem cells and embryonic stem cells. The expression vectors require that the pertinent sequence, i.e., those nucleic acids described supra, be operably linked to a promoter.

The invention also provides isolated KARP-1 polypeptides encoded by the KARP-1 nucleic acids of the invention. The preferred KARP-1 polypeptide has an amino acid sequence of SEQ. ID NO. 2. KARP-1 polypeptides also embrace homologs, functionally equivalent variants, analogs, and unique fragments of SEQ. ID NO. 2, endoded by the KARP-1 nucleic acids. Such polypeptides are useful, for example, alone or as fusion proteins for a variety of purposes such as to generate antibodies, or as a component of an immunoassay.

In general, homologs and alleles typically will share at least 50% amino acid identity to SEQ ID NO:2, in some instances will share at least 65% amino acid identity and in still other instances will share at least 75% amino acid identity.

A unique fragment of a KARP-1 polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of SEQ ID NO:2 will require longer segments to be unique while others will require only short segments, typically between 5 and 12 amino acids (e.g. 5, 6, 7, 8, 9, 10, 11 and 12 amino acids long). Virtually any segment of SEQ ID NO:2 and that is 10 or more amino acids in length will be unique. Unique fragments, however exclude amino acid sequences encompassed completely by the sequence encoded by SEQ ID NO:3. Alternatively, unique fragments include at least one sequence of a leucine zipper domain of SEQ ID NO:4.

Unique fragments of a polypeptide preferably are those fragments which retain a distinct functional capability of the polypeptide. Functional capabilities which can be retained in a unique fragment of a polypeptide include interaction with antibodies, interaction with other polypeptides (such as the subunits of the DNA-PK complex) or fragments thereof (such as the leucine zipper domain), selective binding of nucleic acids or polypeptides, and enzymatic activity. Those skilled in the art are well versed in methods for selecting unique amino acid sequences, typically on the basis of the ability of the unique fragment to selectively distinguish the sequence of interest from other known polypeptides. A comparison of the sequence of the fragment to those on known databases typically is all that is necessary.

The invention embraces variants of the KARP-1 polypeptides described above. As used herein, a "variant" of a KARP-1 polypeptide is a polypeptide which contains one or more modifications to the primary amino acid sequence of a KARP-1 polypeptide. Modifications which create a KARP-1 variant can be made to a KARP-1 polypeptide 1) to reduce or eliminate an activity of a KARP-1 polypeptide, such as double strand DNA base repair; 2) to enhance a property of a KARP-1 polypeptide, such as protein stability in an expression system or the stability of protein-protein binding; or 3) to provide a novel activity or property to a KARP-1 polypeptide, such as addition of an antigenic epitope or addition of a detectable moiety. Modifications to a KARP-1 polypeptide are typically made to the nucleic acid which encodes the KARP-1 polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the KARP-1 amino acid sequence.

In general, variants include KARP-1 polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a KARP-1 polypeptide by eliminating proteolysis by proteases in an expression system (e.g., dibasic amino acid residues in yeast expression systems in which KEX2 protease activity is present).

Mutations of a nucleic acid which encode a KARP-1 polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant KARP-1 polypeptides) which are silent as to the amino acid sequence of the polypeptide, but which provide preferred codons for translation in a particular host. The preferred codons for translation of a nucleic acid in, e.g., E. coli, are well known to those of ordinary skill in the art. Still other mutations can be made to the noncoding sequences of a KARP-1 gene or cDNA clone to enhance expression of the polypeptide. The activity of variants of KARP-1 polypeptides can be tested by cloning the gene encoding the variant KARP-1 polypeptide into a bacterial or mammalian expression vector, introducing the vector into an appropriate host cell, expressing the variant KARP-1 polypeptide, and testing for a functional capability of the KARP-1 polypeptides as disclosed herein. For example, the variant KARP-1 polypeptide can be tested for ability to inhibit DNA-PK activity, as set forth below in the DNA-PK assay and in the examples. Preparation of other variant polypeptides may favor testing of other activities, as will be known to one of ordinary skill in the art.

The skilled artisan will also realize that conservative amino acid substitutions may be made in KARP-1 polypeptides to provide functionally equivalent variants of the foregoing polypeptides, i.e, variants which retain the functional capabilities of the KARP-1 polypeptides. As used herein, a "conservative amino acid substitution" refers to an amino acid substitution which does not alter the relative charge or size characteristics of the polypeptide in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the KARP-1 polypeptides include conservative amino acid substitutions of SEQ ID NO:2. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of KARP-1 polypeptide to produce functionally equivalent variants of KARP-1 polypeptides typically are made by alteration of the nucleic acid encoding KARP-1 polypeptides (SEQ. ID. NO: 1 and/or SEQ. ID. NO: 35). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a KARP-1 polypeptide. Where amino acid substitutions are made to a small unique fragment of a KARP-1 polypeptide, such as a leucine zipper domain, the substitutions can be made by directly synthesizing the peptide. The activity of functionally equivalent fragments of KARP-1 polypeptides can be tested by cloning the gene encoding the altered KARP-1 polypeptide into a bacterial or mammalian expression vector, introducing the vector into an appropriate host cell, expressing the altered KARP-1 polypeptide, and testing for the ability of the KARP-1 polypeptide to interact with the leucine zipper domain of DNA-PKcs. Peptides which are chemically synthesized can be tested directly for function.

A variety of methodologies well-known to the skilled practitioner can be utilized to obtain isolated KARP-1 molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating KARP-1 polypeptides. These include, but are not limited to, immunochromatography, HPLC, size-exclusion chromatography, ion-exchange chromatography and immune-affinity chromatography.

A preferred peptide of the invention is a KARP-1 polypeptide having a leucine zipper region having the following amino acid sequence: $LGX_1NLRX_2$. $X_1$ is selected from the group of amino acids consisting of G, R, and E and $X_2$ is selected from the group of amino acids consisting of M, E, and K. Preferably the KARP-1 polypeptide has at least two leucine zipper amino acid sequences in tandem and more preferably at least five leucine zipper amino acid sequences in tandem.

The invention as described herein has a number of uses, some of which are described elsewhere herein. First, the invention permits isolation of the KARP-1 polypeptide molecules (SEQ ID NO:2). For instance, the isolation of the KARP-1 gene makes it possible for the artisan to diagnose a disorder characterized by loss of expression of KARP-1. These methods involve determining expression of the KARP-1 gene, and/or KARP-1 polypeptides derived therefrom. In the former situation, such determinations can be carried out via any standard nucleic acid determination assay, including the polymerase chain reaction, or assaying with labeled hybridization probes.

The invention also makes it possible isolate polypeptides which bind to KARP-1. Some of these binding polypeptides are useful for inhibiting the activity of KARP-1 such as the ability to repair double stranded DNA. Additional uses are described further herein.

The invention further provides methods for reducing or increasing KARP-1 activity in a cell. Such methods are useful in vitro for altering the ability of a cell to undergo double strand DNA base repair for the purpose of, for example, elucidating the mechanisms involved in double strand DNA base repair (when KARP-1 is reduced) and for restoring the ability of a cell to undergo double strand DNA base repair in a cell having defective Ku86 of KARP-1 (when KARP-1 is increased). In vivo, such methods are useful, for example, for modulating cellular growth, e.g., to treat cancer and fibrosis by inhibiting KARP-1 activity in a rapidly dividing cell by, e.g., introducing a KARP-1 inhibitor into the cell, can be used to inhibit cell growth by inhibiting the repair of mutations which occur in the DNA of the rapidly dividing cells, often leading to cellular death. The ability of inhibitors of KARP-1 to cause cellular death in rapidly dividing cells such as cancer cells is enhanced when these cells are also exposed to an agent which enhances DNA mutation or breakage such as ionizing radiation. In vivo methods for increasing KARP-1 can be performed to treat immunodefficiency caused by defects in Ku86 on KARP-1.

Various modulators of KARP-1 activity can be screened for effects on double strand DNA base repair activity using the methods disclosed herein. The skilled artisan can first determine the modulation of a KARP-1 activity, such as double strand DNA base repair activity, and then apply such a modulator to a target cell or subject and assess the effect on the target cell or subject. For example, in screening for modulators of KARP-1 useful in the treatment of cancer, cells in culture can be contacted with KARP-1 modulators and the increase or decrease of growth or focus formation of the cells can be determined according to standard procedures. KARP-1 activity modulators can be assessed for their effects on other double strand DNA base repair downstream effects by similar methods in many cell types.

The invention also embraces KARP-1 inhibitors. A KARP-1 inhibitor is an agent that inhibits KARP-1 mediated double stranded DNA base repair. KARP-1 inhibitors include for example antisense nucleic acids, peptides that selectively bind to KARP-1, and dominant negative peptides.

DNA-PK activity assays can be performed to screen and or determine whether a KARP-1 inhibitor has the ability to inhibit KARP-1 activity. As used herein, "inhibit" refers to inhibiting by at least 50% double strand DNA base repair, as measured by a DNA-PK activity, as well as to inhibiting a decrease in the amount of double strand DNA base repair. An exemplary DNA-PK activity assay is described in Anderson and Lees-Miller, *Critical Reviews in Eukaryotic Gene Expression*, 2(4):283–314 (1992), which is hereby incorporated in its entirety by reference. A description of this assay is also set forth in Example 6.

In one embodiment the KARP-1 inhibitor is an antisense oligonucleotide that selectively binds to a KARP-1 nucleic acid molecule, to reduce the expression of KARP-1 in a cell and thereby cause the death of the cell as a result of the inability of the cell to repair double stranded DNA. This is desirable in virtually any medical condition wherein a reduction of KARP-1 is desirable, e.g., proliferative disorders such as in a cancer cell. Antisense oligonucleotides also are useful, for example, for preparing an animal model of a condition that is characterized by inability to repair double stranded DNA, e.g., ionizing radiation sensitivity ($IR^S$) and immune deficiency. Such animal models can be used in screening assays for identifying therapeutic drugs which inhibit or reduce $IR^S$ (if appropriate) and immune deficiency.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that MRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ. ID. NO: 1 and/or SEQ. ID. NO: 35, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which polypeptides are not expected to bind. Thus, the present invention also provides for antisense oligonucleotides which are complementary to allelic or homologous cDNAs and genomic DNAs corresponding to SEQ. ID. NO: 1 and/or SEQ. ID. NO: 35.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding KARP-1 polypeptides, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

KARP-1 inhibitors also include binding peptides which bind to KARP-1 and complexes of KARP-1 and its binding partners and inhibit the activity of KARP-1. To determine whether a KARP-1 binding peptide binds to KARP-1 any known binding assay may be employed. For example, the peptide may be immobilized on a surface and then contacted with a labeled KARP-1. The amount of KARP-1 which interacts with the KARP-1 binding peptide or the amount which does not bind to the KARP-1 binding peptide may then be quantitated to determine whether the KARP-1 binding peptide binds to KARP-1.

The KARP-1 binding peptides include peptides of numerous size and type that bind specifically to KARP-1 polypeptides, and complexes of both KARP-1 polypeptides and their binding partners. These peptides may be derived from a variety of sources. For example, such KARP-1 binding peptide can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the KARP-1 polypeptide. This process can be repeated through several cycles of reselection of phage that bind to the KARP-1 polypeptide. Repeated rounds lead to enrichment of phage bearing particular sequences. DNA sequence analysis can be conducted to identify the sequences of the expressed polypeptides. The minimal linear portion of the sequence that binds to the KARP-1 polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the KARP-1 polypeptides. Thus, the KARP-1 polypeptides of the invention, or a fragment thereof, can be used to screen peptide libraries, including phage display libraries, to identify and select peptide binding partners of the KARP-1 polypeptides of the invention. Such molecules can be used, as described, for screening assays, for purification protocols, for interfering directly with the functioning of KARP-1 and for other purposes that will be apparent to those of ordinary skill in the art.

Peptides may easily be synthesized or produced by recombinant means by those of skill in the art. Using routine procedures known to those of ordinary skill in the art, one can determine whether a peptide which binds to KARP-1 is useful according to the invention by determining whether the peptide is one which inhibits the activity of KARP-1 in a DNA-PK activity assay, as discussed above.

The KARP-1 binding peptide may also be an antibody or a functionally active antibody fragment. Antibodies are well known to those of ordinary skill in the science of immunology. As used herein, the term "antibody" means not only intact antibody molecules but also fragments of antibody molecules retaining KARP-1 binding ability. Such fragments are also well known in the art and are regularly employed both in vitro and in vivo. In particular, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl et al., *J. Nucl. Med.* 24:316–325 (1983)).

In one set of embodiments, the antibody useful according to the methods of the present invention is an intact, fully human anti-KARP-1 monoclonal antibody in an isolated form or in a pharmaceutical preparation. The following is a description of a method for developing a monoclonal antibody that interacts with and inhibits the activity of KARP-1. The description is exemplary and is provided for illustrative purposes only.

Murine monoclonal antibodies may be made by any of the methods known in the art utilizing KARP-1 as an immunogen. An example of a method for producing murine monoclonals useful according to the invention is the following: Balb/c mice are immunized intraperitoneally with approximately 75 μg of purified KARP-1 in a complete Freund's adjuvant. Booster injections of approximately 25 μg KARP-1 in incomplete Freund's are administered two and five weeks after the initial injection. After nine weeks, the mice receive booster injections of approximately 25 μg KARP-1 in the absence of adjuvant. Several days later, the mice are killed and the isolated spleen cells fused to murine myeloma cells using polyethylene glycol by a procedure such as that described by Oi (Oi VT: Immunoglobulin-producing hybrid cell lines, in *Hezenberg LA* (Ed): *Selected Methods in Cellular Biology*, San Francisco, Calif., Freeman, (1980)).

Hybridoma cells are selected using hypoxanthine, aminopterin, and thymidine and grown in culture. Two weeks after fusion, hybridoma cells producing anti-KARP-1 monoclonal antibodies are identified using a solid-phase radioimmunoassay by capturing anti-KARP-1 antibodies from conditioned media with immobilized goat antimouse IgG followed by quantitation of specifically bound $^{125}$I-labeled KARP-1. Hybridomas testing positive for antibodies against KARP-1 are subcloned by limiting dilution and retested. Ascites for the hybridomas is then prepared in pristane-primed BALB/c mice by injecting approximately 1×10$^6$ cells/mouse. Concentrates enriched in the selected monoclonal antibodies are produced from ascites fluid by gel filtration on S-200 and concentrated with (NH$_4$)SO$_4$. The pellets are dissolved in an appropriate storage solution such as 50% glycerol/H$_2$O and are stored at 4° C.

Human monoclonal antibodies may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51–63 (Marcel Dekker, Inc, new York, 1987), and Boerner el al., *J. Immunol.*, 147: 86–95 (1991). In addition to the conventional methods for preparing human monoclonal antibodies, such antibodies may also be prepared by immunizing transgenic animals that are capable of producing human antibodies (e.g., Jakobovits et al., *PNAS USA*, 90: 2551 (1993), Jakobovits et al., *Nature*, 362: 255–258 (1993), Bruggermann et al., Year in Immuno., 7:33 (1993) and U.S. Pat. No. 5,569,825 issued to Lonberg).

An example of one method for producing human monoclonals useful according to the invention is the following: Peripheral Blood Lymphocytes (PBL) are isolated from healthy human donors using density centrifugation, and further separated into B, T and accessory (A) cells, by previously described methods such as (Danielsson, L., Moller, S. A. & Borrebaeck, C. A. K. Immunology 61, 51–55 (1987)). PBL are fractionated into T and non-T cells by rosetting with 2-amino ethyl (isothiouronium bromide)— treated sheep red corpuscles, and the latter cell population is incubated on Petri dishes coated with fibronectin or autologous plasma. Non-adherent cells (B-cells) are decanted, and adherent cells (accessory cells) are removed by 10 mM EDTA. The B cells are stimulated with 50 μg Staphylococcus aureus Cowan I/ml and irradiated (2000R) T cells with 10 μg PWM/ml overnight. The accessory cells are stimulated with 5 IU gamma interferon/ml and 10 μm indomethacin. The cell populations are cultured in supplemented RPMI 1640 which contains 10% human AB serum at a cell ratio of 2:1:0.4 (Ti:B:A) for a total of 6 days. The antigenic dose of KARP-1 is 1 μg/ml. The culture is supplemented with recombinant IL-2 (5 U/ml) and sPWM-T (25% by vol.), produced by described methods such as (Danielsson, L., Moller, S. A. & Borrebaeck C. A. K. Immunology 61, 51–55 (1987)). T cells (10 cells/ml) suspended in serum-free RPMI 1640 are incubated with 2.5 mM freshly prepared Leu-OMe for 40 min at room temperature. The cells are then washed 3 times in RPMI 1640 containing 2% human AB serum.

To produce in vitro immunized PBL. The in vitro immunized PBL (1 μg KARP-1/ml) and malign fusion partner are mixed at a ratio of 2:1 and fused using 30% (HF2) or 45% (NS-1/Sp2/0) polyethylene glycol (molecular weight 1540) with 7% dimethylsulphoxide (Borrebaeck, C. A. K. Stand. J. Immunol. 18, 9–12 (1983)). The human x human hybrids are resuspended in supplemented RPMI 1640 containing 10% fetal calf serum, 1 mM sodium pyruvate, 132 μg oxaloacetic acid/ml, 100 μM hypoxanthine, 0.4 μM aminopterin, 16 μM thymidine and 15% by vol. HF2-conditioned medium. Mouse myeloma cells are fused and cloned, except that feeder cells are omitted. Both human x human and human x mouse hybrids are plated out in 24 well plates (0.7–1.0× 10<6>cells/well). The hybridomas are screened for production of specific antibodies, using an enzyme immunoassay. To sum up, 96 microtiter wells are each coated with 0.3 μg KARP-1 by allowing the KARP-1 solution to dry in the well. Gelatin (0.1%) is then used in order to block the wells for 30 min. at 37° C. The hybridoma supernatant (100μ l/well) is added to the washed wells and allowed to react for 30 min. At 37° C. Peroxidase-conjugated anti-human Ig antibodies diluted in phosphate buffered saline solution containing 10% fetal calf serum (100μ l/well) are finally incubated for 60 min., and enzyme substrate (ABTS) are added to develop the immunoassay.

Alternatively the antibody may be a polyclonal antibody specific for KARP-1 which inhibits KARP-1 activity. The preparation and use of an anti-KARP-1 polyclonal antibody is described more fully in the attached Examples.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fe regions, for example, are effectors of the complement cascade but are not involved .in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fe region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

In general, intact antibodies are said to contain "Fc"' and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinant of antibody specificity (a single Fd fragment may be associated with up to ten different light chains without altering antibody specificity). Isolated Fd fragments retain the ability to specifically bind to antigen epitopes.

Within the antigen-binding region of an antibody are complementarity determining regions (CDRs) which directly interact with the epitope of the antigen, and framework regions (FRs), which maintain the tertiary structure of the paratope (see, A. G. Clark, 1986 supra; Roitt, 1991 supra). In both the heavy chain Fd fragment and the light chain of the IgG immunoglobulins, there are four framework regions (FR1–FR4) separated respectively by three complementarity determining regions (CDR1–CDR3). The CDRs, and in particular the CDR3 region, and more particularly the heavy chain CDR3, are primarily responsible for antibody specificity.

The sequences of the antigen-binding Fab' portion of the anti-KARP-1 monoclonal antibodies identified as being useful according to the invention in the assays provided above, as well as the relevant FR and CDR regions, can be determined using amino acid sequencing methods that are routine in the art. It is well established that non-CDR regions of a mammalian antibody may be replaced with corresponding regions of non-specific or hetero-specific antibodies while retaining the epitope specificity of the original antibody. This technique is useful for the development and use of "humanized" antibodies in which non-human CDRs are covalently joined to human FR and/or Fc/pFc' regions to produce a functional antibody. Techniques to humanize antibodies are particularly useful when non-human animal (e.g., murine) antibodies which inhibit KARP-1 activity are identified. These non-human animal antibodies can be humanized for use in the treatment of a human subject in the methods according to the invention. An example of a method for humanizing a murine antibody is provided in PCT International Publication No. WO 92/04381 which teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, and Fab fragments of an anti-KARP-1 monoclonal antibody; chimeric antibodies in which the Fc and/or FR and/or CDR1 and/or CDR2 and/or light chain CDR3 regions of an anti-KARP-1 antibody have been replaced by homologous human or non-human sequences; chimeric F(ab')$_2$ fragment antibodies in which the FR and/or CDR1 and/or CDR2 and/or light chain CDR3 regions of an anti-KARP-1 antibody have been replaced by homologous human or non-human sequences; and chimeric Fab fragment antibodies in which the FR and/or CDR1 and/or CDR2 and/or light chain CDR3 regions have been replaced by homologous human or non-human sequences. Thus, those skilled in the art may alter an anti-KARP-1 antibody by the construction of CDR grafted or chimeric antibodies or antibody fragments containing, all or part thereof, of the disclosed heavy and light chain V-region CDR AA sequences (Jones et al., *Nature* 321:522, 1986; Verhoeyen et al., Science 39:1534, 1988 and Tempest et al., Bio/Technology 9:266, 1991), without destroying the specificity of the antibodies for KARP-1. Such CDR grafted or chimeric antibodies or antibody fragments can be effective in inhibiting KARP-1 activity in animals (e.g. primates) and humans.

In preferred embodiments, the chimeric antibodies of the invention are fully human monoclonal antibodies. As noted above, such chimeric antibodies may be produced in which some or all of the FR regions of KARP-1 have been replaced by other homologous human FR regions. In addition, the Fc portions may be replaced so as to produce IgA or IgM as well as IgG antibodies bearing some or all of the CDRs of the Anti-KARP-1 antibody. Of particular importance is the inclusion of the anti-KARP-1 heavy chain CDR3 region and, to a lesser extent, the other CDRs of anti-KARP-1. Such fully human chimeric antibodies will have particular utility in that they will not evoke an immune response against the antibody itself.

It is also possible, in accordance with the present invention, to produce chimeric antibodies including non-human sequences. Thus, one may use, for example, murine, ovine, equine, bovine or other mammalian Fc or FR sequences to replace some or all of the Fc or FR regions of the anti-KARP-1 antibody. Some of the CDRs may be replaced as well. Again, however, it is preferred that at least the heavy chain CDR3 region of the anti-KARP-1 antibody be included in such chimeric antibodies and, to a lesser extent, it is also preferred that some or all of the other CDRs of anti-KARP-1 be included. Such chimeric antibodies bearing non-human immunoglobulin sequences admixed with the CDRs of the human anti-KARP-1 monoclonal antibody are not preferred for use in humans and are particularly not preferred for extended use because they may evoke an immune response against the non-human sequences. They may, of course, be used for brief periods or in immunosuppressed individuals but, again, fully human antibodies are preferred. Because, however, such antibodies may be used for brief periods or in immunosuppressed subjects, chimeric antibodies bearing non-human mammalian Fc and FR sequences but including at least the anti-KARP-1 heavy chain CDR3 are contemplated as alternative embodiments of the present invention.

For inoculation or prophylactic uses, the antibodies of the present invention are preferably intact antibody molecules including the Fc region. Such intact antibodies will have longer half-lives than smaller fragment antibodies (e.g. Fab) and are more suitable for intravenous, intraperitoneal, intramuscular, intracavity, subcutaneous, or transdermal administration.

Fab fragments, including chimeric Fab fragments, are preferred in methods in which the antibodies of the invention are administered directly to a local tissue environment. For example, the Fab fragments are preferred when the antibody of the invention is administered directly to the site of a tumor clot. Fabs offer several advantages over F(ab')$_2$ and whole immunoglobulin molecules for this therapeutic modality. First, because Fabs have only one binding site for their cognate antigen, the formation of immune complexes is precluded whereas such complexes can be generated when bivalent F(ab')$_2$ s and whole immunoglobulin molecules encounter their target antigen. This is of some importance because immune complex deposition in tissues can produce adverse inflammatory reactions. Second, because Fabs lack an Fc region they cannot trigger adverse inflammatory reactions that are activated by Fc, such as activation of the complement cascade. Third, the tissue penetration of the small Fab molecule is likely to be much better than that of the larger whole antibody. Fourth, Fabs can be produced easily and inexpensively in bacteria, such as E. coli, whereas whole immunoglobulin antibody molecules require mammalian cells for their production in useful amounts. Production of Fabs in E. coli makes it possible to produce these antibody fragments in large fermenters which are less expensive than cell culture-derived products.

Smaller antibody fragments and small binding peptides having binding specificity for the KARP-1 which can be used to inhibit KARP-1 activity also are embraced within the present invention. For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated VH single domain, also have been reported (see, for example, Ward et al., *Nature* 341:644–646 (1989)).

According to the invention KARP-1 inhibitors also include "dominant negative" polypeptides derived from SEQ ID NO:2. A dominant negative polypeptide is an inactive variant of a polypeptide, which, by interacting with the cellular machinery, displaces an active polypeptide from its interaction with the cellular machinery or competes with the active polypeptide, thereby reducing the effect of the active polypeptide. For example, a dominant negative receptor which binds a ligand but does not transmit a signal in response to binding of the ligand can reduce the biological effect of expression of the ligand. Likewise, a dominant negative subunit of an active complex (e.g. DNA-PK) which interacts normally with the complex but prevents the activity of the complex (e.g. double strand DNA base repair). Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative KARP-1 polypeptide of the invention in a cell is a reduction in double strand DNA base repair. One of ordinary skill in the art can assess the potential for a dominant negative variant of a KARP-1 polypeptide, and using standard mutagenesis techniques to create one or more dominant negative variant polypeptides. For example, given the teachings contained herein of a KARP-1 polypeptide, one of ordinary skill in the art can modify the sequence of the KARP-1 polypeptide by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in KARP-1 activity (e.g., KARP-1 dependent reduction of DNA-PK activity or IRS) and/or for retention of such an activity. Other similar methods for creating and testing dominant negative variants of a KARP-1 polypetide will be apparent to one of ordinary skill in the art.

Dominant negative KARP-1 polypeptides include variants in which a portion of the DNA-PK binding site (leucine zipper domain) has been mutated or deleted to reduce or eliminate KARP-1 dependent DNA-PK activity. Other examples include dominant negative KARP-1 polypeptides in which the ability activate DNA-PK activity is reduced. One of ordinary skill in the art can readily prepare and test KARP-1 variants bearing mutations or deletions in the highly basic region or in the leucine zipper domain.

Each of the compositions of the invention is useful for a variety of therapeutic and non-therapeutic purposes. For example, the KARP-1 nucleic acids of the invention are useful as oligonucleotide probes. Such oligonucleotide probes can be used herein to identify genomic or cDNA library clones possessing an identical or substantially similar nucleic acid sequence. A suitable oligonucleotide or set of oligonucleotides, which is capable of hybridizing under stringent hybridization conditions to the desired sequence, a variant or fragment thereof, or an anti-sense complement of such an oligonucleotide or set of oligonucleotides, can be synthesized by means well known in the art (see, for example, *Synthesis and Application of DNA and RNA*, S. A. Narang, ed., 1987, Academic Press, San Diego, Calif.) and employed as a probe to identify and isolate the desired sequence, variant or fragment thereof by techniques known in the art. Techniques of nucleic acid hybridization and clone identification are disclosed by Sambrook, et al., *Molecular Cloning, A Laboratory Manual,* 2d ed., Cold Spring Harbor Laboratory Press, Plainview, N.Y. (1989), and by Hames, B. D., et al., in *Nucleic Acid Hybridization, A Practical Approach*, IRL Press, Washington, DC (1985). To facilitate the detection of a desired nucleic acid sequence, or variant or fragment thereof, whether for cloning purposes or for the mere detection of the presence of the sequence, the above-described probes may be labeled with a detectable group. Such a detectable group may be any material having a detectable physical or chemical property. Such materials have been well-developed in the field of nucleic acid hybridization and, in general, most any label useful in such methods can be applied to the present invention. Particularly useful are radioactive labels. Any radioactive label may be employed which provides for an adequate signal and has a sufficient half-life. If single stranded, the oligonucleotide may be radioactively labeled using kinase reactions. Alternatively, oligonucleotides are also useful as nucleic acid hybridization probes when labeled with a non-radioactive marker such as biotin, an enzyme or a fluorescent group. See, for example, Leary, J. J., et al., *Proc. Natl. Acad. Sci. (USA)* 80:4045 (1983); Renz, M. et al., *Nucl. Acids Res.* 12:3435 (1984); and Renz, M., *EMBO J.* 6:817 (1983).

Unique KARP-1 nucleic acid fragments may be used to screen polypeptides which bind to the promoter region of KARP-1. For instance, p53 is demonstrated herein to interact with the KARP-1 promoter. The unique fragments of the invention can be used to identify fragments of p53 that bind to KARP-1 promoter as well as to identify other polypeptides which bind to the KARP-1 promoter such as p73. Likewise expression vectors including at least unique nucleic acid fragments and a reporter gene may be used to determine which polypeptides that bind to the promoter region of KARP-1 are capable of inducing transcription of the KARP-1 gene. Polypeptides which induce expression of the KARP-1 gene can be used to induce KARP-1 levels, particularly in cells which have mutations in or deletion of p53.

Additionally, complements of the KARP-1 nucleic acids can be useful as anti-sense oligonucleotides, e.g., by delivering the anti-sense oligonucleotide to an animal to induce a KARP-1 "knockout" phenotype. The administration of anti-sense RNA probes to block gene expression is discussed in Lichtenstein, C., *Nature* 333:801–802 (1988).

Alternatively, the KARP-1 nucleic acid of the invention can be used to prepare a non-human transgenic animal. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Transgenic animals having a particular property associated with a particular disease can be used to study the affects of a variety of drugs and treatment methods on the disease, and thus serve as genetic models for the study of a number of human diseases. The invention, therefore, contemplates the use of KARP-1 knockout and transgenic animals as models for the study of disorders involving double strand DNA base repair, such as immune deficiency and radiation sensitivity as well as for the study of the effect of supplying a KARP-1 gene to an animal having immune deficiency or radiation sensitivity such as the Ku86 knock out mouse (Zhu et al., 1996).

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division. See e.g., Brinster et al., *Proc. Nat. Acad. Sci. USA*, 82: 4438 (1985); Brinster et al., cell 27: 223 (1981); Costantini et al., *Nature* 294: 982 (1981); Harpers et al., *Nature* 293: 540 (1981); Wagner et al., *Proc. Nat. Acad. Sci. USA* 78:5016 (1981); Gordon et al., *Proc. Nat. Acad. Sci. USA* 73: 1260 (1976). The fertilized egg is then implanted into the uterus of the recipient female and allowed to develop into an animal.

An alternative method for producing transgenic animals involves the incorporation of the desired gene sequence into a virus which is capable of affecting the cells of a host animal. See e.g., Elbrecht et al., *Molec. Cell. Biol.* 7: 1276 (1987); Lacey et al., *Nature* 322: 609 (1986); Leopol et al., Cell 51: 885 (1987). Embryos can be infected with viruses, especially retroviruses, modified to carry the nucleotide sequences of the invention which encode KARP-1 proteins or sequences which disrupt the native KARP-1 gene to produce a knockout animal.

Another method for producing transgenic animals involves the injection of pluripotent embryonic stem cells into a blastocyst of a developing embryo. Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. See e.g., Robertson et al., Cold Spring Harbor Conference Cell Proliferation 10: 647 (1983); Bradley et al., Nature 309: 255 (1984); Wagner et al., Cold Spring Harbor Symposium Quantitative Biology 50: 691 (1985).

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia,* 47: 897–905 (1991). Other procedures for introduction of DNA into tissues of animals are described in U.S. Pat. No. , 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer etal., *Cell,* 63:1099–1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells, A Practical Approach*, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, *Science,* 244: 1288–1292 (1989). Methods for positive selection of the recombination event (e.g., neo resistance) and dual positive-negative selection (e.g., neo resistance and gangcyclovir resistance) and the subsequent identification of the desired clones by PCR have been described by Capecchi, supra and Joyner et al., *Nature,* 338: 153–156 (1989). The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene.

Procedures for the production of non-rodent mammals and other animals have been discussed by others. See Houdebine and Chourrout, supra; Pursel et al., *Science* 244: 1281–1288 (1989); and Simms et al., *Bio/Technology,* 6: 179–183 (1988).

Inactivation or replacement of the endogenous KARP-1 gene can be achieved by a homologous recombination system using embryonic stem cells. The resultant transgenic non-human mammals (preferably primates) having a knock-out KARP-1 characteristic may be used as a model for immunodeficiency and $IR^5$. A variety of therapeutic drugs can be administered to the phenotypically immundeficient animals to determine the affect of the therapeutic drugs on improving the immune system. In this manner, such therapeutic drugs can be identified.

Additionally, a normal or mutant version of KARP-1 can be inserted into the mouse (or the animal) germ line to produce transgenic animals which constitutively or inducibly express the normal or mutant form of KARP-1. These animals are useful in studies to define the role and function of KARP-1 in cells. These studies are particularly useful in animals, which do not normally express KARP-1, such as non-primates.

A KARP-1 polypeptide, or a fragment thereof, also can be used to isolate KARP-1 native binding partners, including, e.g., the DNA-PK complex. Isolation of such binding partners may be performed according to well-known methods. For example, isolated KARP-1 polypeptides can be attached to a substrate (e.g., chromatographic media, such as polystyrene beads, or a filter), and then a solution suspected of containing the DNA-PK complex may be applied to the substrate. If a DNA-PK complex which can interact with KARP-1 polypeptides is present in the solution, then it will bind to the substrate-bound KARP-1 polypeptide. The DNA-PK complex then may be isolated. Other polypeptides which are binding partners for KARP-1 may be isolated by similar methods without undue experimentation.

Additionally, a KARP-1 polypeptide, or a fragment thereof, also can be used to identify putative DNA having a KARP-1 binding site. Identification of such binding partners may be performed according to well-known methods, such as gel-shift assays.

The compositions of the invention are also useful for therapeutic purposes. Accordingly the invention encompasses a method for inhibiting KARP-1 activity in a mammalian cell. The method involves the step of contacting the mammalian cell with an amount of a KARP-1 inhibitor of the invention effective to inhibit double stranded DNA base repair in the mammalian cell.

An amount of a KARP-1 inhibitor which is effective to inhibit double stranded DNA base repair in the mammalian cell is an amount which is sufficient to reduce DNA-PK activity by 50%. A reduction in DNA-PK activity can be measured by the assays described herein.

In a preferred aspect of the invention the method may be used to modulate the proliferation of a cancer cell. When the KARP-1 inhibitor of the invention is administered to a cancer cell, it is administered in conjunction with a conventional chemotherapeutic agent. The KARP-1 inhibitor inhibits double strand DNA base repair and thus causes cellular death in rapidly proliferating cells which are prone to DNA damage. In this manner, less of the chemotherapeutic agent can be used to achieve a medically desirable when administered with the KARP-1 inhibitor than when administered without the KARP-1 inhibitor. Unfavorable side effects resulting from the chemotherapeutic agent, therefore, can be lessened or perhaps even eliminated. Likewise, chemotherapeutic agents with a limited range of uses due to high toxicity can find a broader range of uses when the effective dose is reduced by using the chemotherapeutic agent in conjunction with a KARP-1 inhibitor as described herein.

Chemotherapeutic agents function by a variety of mechanisms and include those agents disclosed in Chapter 52, Antineoplastic Agents (Paul Calabresi and Bruce A. Chabner), and the introduction thereto, 1202–1263, of Goodman and Gilman's "The Pharmacological Basis of Therapeutics", Eighth Edition, 1990, McGraw-Hill, Inc. (Health Professions Division), incorporated herein by reference and hereinafter referred to as "Calabresi and Chabmer in G & G". Suitable chemotherapeutic agents may have various mechanisms of action. The classes of suitable chemotherapeutic agents include (a) Alkylating Agents such as nitrogen mustard (e.g. mechlorethamine, cylophosphamide, ifosfamide, melphalan, chlorambucil), ethylenimines and methylmelamines (e.g. hexamethylmelamine, thiotepa), alkyl sulfonates (e.g. busulfan), nitrosoureas (e.g. carmustine which is also known as BCNU, lomustine which is also known as CCNU semustine which is also known as methyl-CCNU, chlorozoticin, streptozocin), and triazines (e.g. dicarbazine which is also known as DTIC); (b) Antimetabolites such as folic acid analogs (e.g. methotrexate), pyrimidine analogs (e.g. 5-fluorouracil floxuridine, cytarabine, and azauridine and its prodrug form azaribine), and purine analogs and related materials (e.g. 6-mercaptopurine, 6-thioguanine, pentostatin); (c) Natural Products such as the vinca alkaloids (e.g. vinblastine, Vincristine), epipodophylotoxins (e.g. etoposide, teniposide), antibiotics (e.g dactinomycin which is also known as actinomycin-D, daunorubicin, doxorubicin, bleomycin, plicamycin, mitomycin, epirubicin, which is 4-epidoxorubicin, idarubicin which is 4-dimethoxydaunorubicin, and mitoxanthrone), enzymes (.e.g L-asparaginase), and biological response modifiers (e.g. Interferon alfa); (d) Miscellaneous Agents such as the platinum coordination complexes (e.g. cisplatin, carboplatin), substituted ureas (e.g. hydroxyurea), methyl-hydiazine derivatives (e.g. procarbazine), adreocortical suppressants (e.g. mitotane, aminoglutethimide) taxol; (e) Hormones and Antagonists such as adrenocorticosteroids (e.g. prednisone or the like), progestins (e.g. hydroxyprogesterone caproate, medroxyprogesterone acetate, megestrol acetate), estrogens (e.g. diethyestilbestrol, ethinyl estradiol, and the like), antiestrogens (e.g. tamoxifen), androgens (e.g. testosterone propionate, fluoxymesterone, and the like), anti-androgens (e.g. flutamide), and gonadotropin-releasing hormone analogs (e.g. leuprolide) and (F) DNA damaging compounds such as radiation. Although DNA damaging compounds are not always classified as chemotherapeutic agents, the term "chemotherapeutic agent" as used herein encompassed DNA damaging agents.

Among the preferred anti-cancer chemotherapeutic agents for use in the present invention are DNA-damaging agents. DNA-damaging agents are preferred because they induce damage in the DNA of rapidly proliferating cells. Ordinarily that damage is repaired by DNA-PK. In the presence of a KARP-1 inhibitor, however, the activity of DNA-PK is impaired and double strand DNA base repair is inhibited.

The invention is used in connection with treating cancers. Cancers include, but are not limited to, biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; multiple myeloma; AIDS associates leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basal cell Ecancer and squamous cell cancer; testicular cancer, including germinal tumors (seminoma, non-seminoma (teratomas, choriocarcinomas)), stromal tumors and germ cell tumors; thyroid cancer, including thyroid adenocarcinoma and medullar carcinoma; and renal cancer including adenocarcinoma and Wilms tumor.

In general the cancer cell is sensitive to chemotherapy in the absence of the KARP-1 inhibitor. When a cancer cell is sensitive to a chemotherapeutic agent, then the chemotherapeutic agent and the KARP-1 inhibitor are administered in a combined amount effective to inhibit growth of the cancer. The combined amount is an amount of chemotherapeutic agent and an amount of KARP-1 inhibitor such that the amount of chemotherapeutic agent is effective to inhibit the proliferation of the cancer cell when the double strand DNA base repair is inhibited and that the amount of KARP-1 inhibitor is effective to prevent double strand DNA base repair. The combined amounts are effective for inhibiting growth of the cancer.

A "cancer cell which is resistant to DNA-damaging chemotherapy" as used herein is one which is not responsive to chemotherapy which damages DNA, such as ionizing radiation. When such cancer cells are treated with the DNA-damaging chemotherapeutic agent in combination with a KARP-1 inhibitor. The KARP-1 inhibitor can increase the sensitivity of the cell to the agent. It is believed that the KARP-1 inhibitor accomplishes this by inhibiting the function of an efficient DNA-PK which was preventing the effects of the agent by repairing DNA.

In one aspect of the invention, the KARP-1 inhibitor is administered substantially simultaneously with the chemotherapeutic agent. By substantially simultaneously, it is meant that the KARP-1 inhibitor is administered to the subject close enough in time with the administration of the chemotherapeutic agent, whereby the KARP-1 inhibitor may exert a its effect on the tumor cells at the same time as the chemotherapeutic agent.

The invention also encompasses a method for increasing KARP-1 expression in a subject. It is desirable to increase KARP-1 in a subject that has immune deficiency disorder caused by a deficiency in KARP-1 or Ku86. KARP-1 can be increased in such subjects by administering a KARP-1 nucleic acid or a KARP-1 polypeptide of the invention to the subject in an amount effective to increase KARP-1 expression in the cells of the subject. The invention also contemplates a method for treating a subject having an immune deficient disorder by administering KARP-1 nucleic acid or a KARP-1 polypeptide of the invention to the subject in an amount effective to increase KARP-1 activity. An increase in KARP-1 activity can be measured by the assays described herein, eg., DNA-PK activity assay.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. Ex vivo gene therapy is particularly important for the treatment of imunodeficient subjects. Recent methods have been developed to enhance isolation of stem cells of the immune system in imunodeficient subjects. These isolated stem cells can be transfected with a functional KARP-1 gene or fragment thereof to improve DNA-PK activity in the cells once the cells are returned to the body. In vivo gene therapy using vectors such as adenovirus, retroviruses, herpes virus, and targeted liposomes also is contemplated according to the invention.

The preparations of the invention are administered in effective amounts. An effective amount is that amount of a pharmaceutical preparation that alone, or together with further doses, produces the desired response. In the case of treating cancer, the desired response is inhibiting the progression of the cancer. This may involve only slowing the progression of the disease temporarily, although more preferably, it involves halting the progression of the disease permanently. This can be monitored by routine methods.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. It is preferred generally that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Generally, doses of active compounds would be from about 0.01 mg/kg per day to 1000 mg/kg per day. It is expected that doses ranging from 50–500 mg/kg will be suitable and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

When administered, the pharmaceutical preparations of the invention are applied in pharmaceutically-acceptable amounts and in pharmaceutically-acceptably compositions. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The KARP-1 inhibitors or KARP-1 nucleic acids and polypeptides useful according to the invention may be combined, optionally, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. When the KARP-1 inhibitor is administered to a subject to treat cancer local administration is preferred.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous preparation of the KARP-1 inhibitor or KARP-1 nucleic acids and polypeptides, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

Other delivery systems can include time-release, delayed release or sustained release delivery systems such as the biological/chemical vectors is discussed above. Such systems can avoid repeated administrations of the active compound, increasing convenience to the subject and the physician. Many types of release delivery systems are available and known to those of ordinary skill in the art. Use of a long-term sustained release implant may be desirable. iLong-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The invention also encompasses pharmaceutical compositions of the above-described active agents and formulations.

The invention will be more fully understood by reference to the following examples. These examples, however, are merely intended to illustrate the embodiments of the invention and are not to be construed to limit the scope of the invention.

EXAMPLES

Example 1

Identification of a novel open reading frame in the human Ku86 promoter region and isolation of KARP-1 genomic clones.

1. Methods

Isolation of KARP-1 genomic clones: The genomic DNA 5'-upstream of the Ku86 initiator ATG was obtained by Polymerase Chain Reaction (PCR) using a GenomeWalker Kit (Clontech). Primary PCR utilized the Ming5 (5'-CTCATGGTAAAGCCCACGTCCATACACAGC-3') (SEQ ID NO:7) and AP-1 primers (5'-GTAATACGACTCACTATAGGGC-3') (SEQ ID NO:8) and secondary PCR utilized Ming4 (5'-AACAGCTGCCTTATTCCCCGACCGCACCAT-3') (SEQ ID NO: 9)and AP-2 (5'-ACTATAGGGCACGCGTGGT-3') (SEQ ID NO:10) primers. The ~1.2 kb resulting PCR fragment was subcloned using a TA cloning vector (Invitrogen) and sequenced. This information was utilized to generate additional PCR primers, Ming 14 (5'-TCTTGTCAGTGGTCCTTGTCTCCCTTCTTG-3') (SEQ ID NO:11) and Ming 15 (5'-TACGATCCAGAGCTAGGGAGAGAGAGAAAA-3') (SEQ ID NO:12), homologous to 5'-distal sequences and the process was repeated until ~4.0 kb of genomic DNA was subcloned.

Sequence analyses were performed either with DNASIS (Hitachi) or the GCG computer program (University of Wisconsin).

2. Results

The presumptive promoter region of the human Ku86 gene was obtained by PCR using primers derived from the 5'-end of the human Ku86 sequence (Mimori et al., 1990) and a commercially available genomic DNA isolation kit (GenomeWalker, Clontech). Initially, a 1.2 kb DNA fragment was isolated and sequenced. This information was utilized to isolate by PCR an additional fragment. Together, these fragments comprised ~4 kb of genomic DNA sequence upstream of the initiator ATG for the Ku86 gene. Subsequently, much of this sequence was verified by sequencing the corresponding regions from clones, isolated by conventional colony hybridization screening, of an independent human genomic library. As shown in FIG. 1, an open reading frame (ORF) upstream of Ku86 is in-frame and contiguous with Ku86 and extends at least an additional 88 amino acids beyond the Ku86 ATG. Usually stop codons are found upstream of the initiator ATG in mammalian genes (Kozak, 1987). Lower-case letters correspond to intronic DNA, whereas upper-case letters correspond to KARP-1 exon DNA and the bold, upper-case letters correspond to the Ku86 gene. The predicted KARP-1 polypeptide sequence is shown using the single letter amino acid code. The Ku86 5'-UTR ORF also encodes several in-frame methionines (FIG. 1). In the few cases where long ORFs in the 5'-untranslated region (UTR) of genes have been described in the prior art they usually do not encode additional potential initiator methionine residues (Kozak, 1991; Xiong et al., 1991). Thirdly, the Ku86 5'-UTR ORF contains an extremely basic region in which 15 of 37 residues were either lysines or arginines, including a potential nuclear localization signal (Kalderon et al., 1984). Basic amino acids in the flanking domain are marked with a plus (+). A putative nuclear localization signal is shown by the horizontal line.

Lastly, the Ku86 5'-UTR ORF also has the capacity to encode a novel leucine repeat which consists of a perfect hexaheptad repeat of leucine residues interdigitated with a perfect penta-heptad repeat of leucines (FIGS. 1 and 2A). The leucine residues in the hexaheptad repeat are shown by a bold asterisk (*) while the leucine residues in the penta-heptad repeat are shown by a normal asterisk (*). Heptad repeats of leucines are characteristic of a subset of coiled-coil proteins known as leucine zippers. These proteins have a characteristic seven-residue repeat, $(a \cdot b \cdot c \cdot d \cdot e \cdot f \cdot g)_n$ in which a leucine residue is found at all or most of the 'd' positions and hydrophobic residues are found at the 'a' positions. (Landschulz et al., 1988; reviewed in Hurst, 1994). The leucine repeats observed in the Ku86 5'-UTR ORF conform to this pattern (FIG. 2A). A helical wheel diagram of the leucine repeated within the N-terminus of KARP-1 is shown in FIG. 2A. The lower-case letters correspond to the seven positions within the α-helix. The KARP-1 amino acids are shown using the single letter amino acid code starting with the first leucine at amino acid 2.

Analysis of the ORF sequence revealed two additional features. First, a computer search suggested that the leucine repeat sequence had weak homology (20% identity and 40% similarity) to the Hin integrase (FIG. 2B). The amino acid sequence of both KARP-1 and Hin are aligned throughout the leucine repeated region. A consensus sequence is shown below with identical residues in upper-case and conserved residues demarcated by an asterisk (*) The following amino acids were considered similar: D, E, N and Q; F, W and Y; K and R; A and G; I, V, L and M; S and T; C; H; P. Recently, it has been shown that the RAG-1 gene (Schatz et al., 1989), which is absolutely required for V(D)J recombination (Mombaerts et al., 1992) also has functional homology to the Hin integrase and that the recombination signal sequences which mediate V(D)J recombination resemble the Hin recombination site (Spanopoulou et al., 1996; reviewed by Lewis and Wu, 1997). Secondly, heptad repeats of leucines are a motif found in protein interaction domains and over 80 such domains have been identified (Hurst, 1994). Most heptad repeats of leucines, however, are only four, or occasionally five, leucines long and a perfect hexa-heptad repeat appears, to our knowledge, to have been reported only once previously in the literature. Intriguingly, the protein with a perfect hexa-heptad repeat of leucines is DNA-PK$_{CS}$ (FIG. 2C; Hartley et al., 1995), the protein with which Ku86 is known to interact (Dvir et al., 1992; Gottlieb and Jackson, 1993; Suwa et al., 1994). The amino acid sequence of both KARP-1 and DNA-PK$_{CS}$ are aligned throughout the leucine repeat region (FIG. 2C). Identical residues are shown with a vertical line and conserved residues demarcated by an asterisk (*)

Example 2

The KARP-1 sequence is transcribed into poly(A)+ mRNA

1. Methods

Northern blot analysis: Poly(A)+RNA was isolated from HCW2 and Sc5 cells using a FastTrack MRNA isolation kit (Invitrogen) and 10 μg was electrophoresed on a 1.2% agarose gel. The gel was subsequently incubated in 0.5 M NaOH for 15 min and neutralized in 20× SSC for 40 min. mRNA was transferred onto nitrocellulose by capillary transfer and hybridized in 50% formamide, 5× Denhardt's solution, 5× SSPE, 0.1% sodium dodecyl sulfate (SDS), 100 μg/ml herring sperm DNA, and 2% polyethylene glycol (PEG) 8000 with a 328 bp KARP-1-specific probe generated by PCR using the primers KJ10 (5'-GCTCAAACACCACACGCCCC-3') (SEQ ID NO:13) and Ming1 (5'-TTATTCCCCGACCGCACCAT-3') (SEQ ID NO:14) and radiolabeled by random priming (Stratagene).

Tissue-specific library PCR: Library PCR was carried out using human tissue-specific cDNA libraries (Clontech) as templates. KJ10 and Ming1 primers were used for the PCR reactions. As a control, β-actin PCR primers, provided by the supplier, were also used. PCR =products were separated by electrophoresis on a 1.0% agarose gel and transferred onto nitrocellulose. Southern hybridization of this filter was performed in 50% formamide, 5× Denhardt's solution, 5× SSPE, 0.1% SDS, and 100 μg/ml herring sperm DNA with the 328 bp KARP-1-specific probe described above.

2. Results

Two experimental schemes were utilized to demonstrate that KARP-1 sequences were transcribed into mRNA. First, a radiolabeled probe corresponding to the KARP-1 sequences was prepared and Northern blot analysis was performed utilizing poly(A)+ mRNA isolated from human HCW2 cells (a subline of the human promyelocytic leukemia cell line, HL60; Han et al., 1996) and Sc5 cells (described in FIG. 8 below) (FIG. 3A). (Top) Poly(A)$^+$ mRNA (10 μg) from HCW2 and Sc5 cells was prepared for Northern blot analysis as described in the Materials and methods. (Bottom) The probe consisted of a 328 bp fragment corresponding to the leucine (L) repeat and basic (+) region of KARP-1. A single ~3.2 kb signal was observed in HCW2 cells' mRNA. Importantly, this pattern is different from that observed using a probe to Ku86, which results in two equally intense signals of ~2.6 and ~3.4 kb (Mimori et al., 1990). The two different-sized Ku86 transcripts are apparently the result of alternative polyadenylation as the ~3.4 kb transcript contains ~0.8 kb more 3'-UTR than the ~2.6 kb transcript (Mimori et al., 1990). From this experiment we concluded that the KARP-1 region was transcribed and that the transcript was different from the normal Ku86 mRNA(s).

To confirm the above result PCR was performed with two KARP-1-specific primers and a variety of human tissue-specific cDNA libraries (Clontech, see Material and methods). As a positive control, PCR was also performed using β-actin-specific primers and all PCR products were subjected to agarose gel electrophoresis. The tissue-specific library PCR demonstrated that KARP-1 is ubiquitously expressed at low levels. Ethidium bromide staining of the resulting gel shows only a signal corresponding to the 835 base pair P-actin (FIG. 3B). After the gel was transferred to nitrocellulose it was analyzed by Southern blot hybridization using a 328 bp KARP-1 specific probe. Autoradiography revealed the expected 328 bp KARP-1 PCR product was observed in all human tissues except, perhaps, in skeletal muscle (FIG. 3B). FIG. 3B indicated that KARP-1 is predominately ubiquitously expressed and that its expression level is significantly below that of the abundant β-actin message.

Figures 4A, 4B:
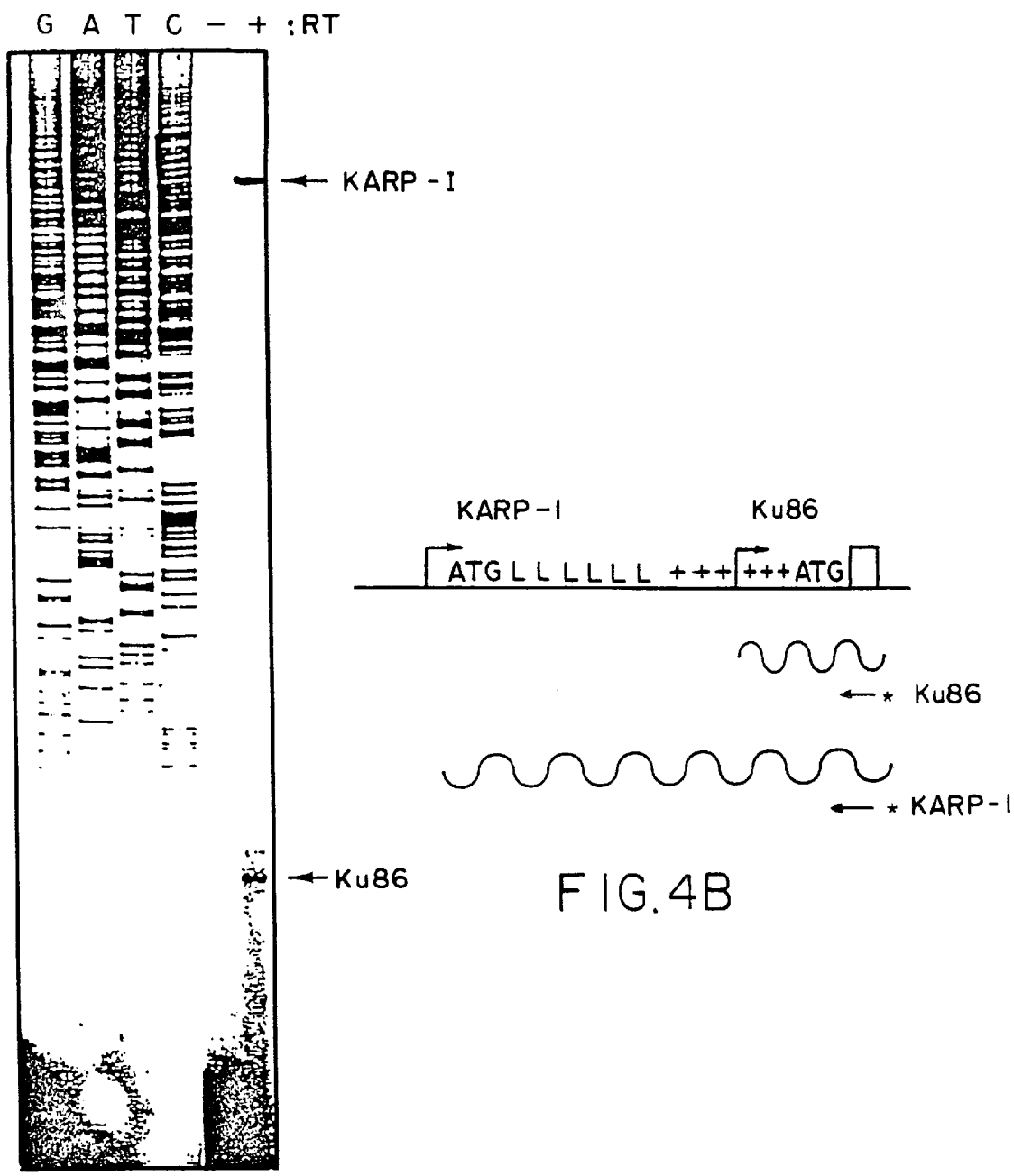
FIG. 4A shows the results of a primer extension analysis performed in either the presence (+) or absence (−) of reverse transcriptase (RT) which reveals two predominant start sites for the Ku86 locus.
FIG. 4B shows a schematic of the experimental procedure used in primer extension analysis.

Example 3
Mapping the 5'-end of KARP-1 by primer extension analysis reveals two predominant start sites for the Ku86 locus.
1. Methods
Primer extension: Primer extension was performed with 1 μg of poly(A)+RNA, RNA and an end-labeled primer (Ming4) (SEQ ID NO:9) were incubated at 65 ° C. for 2 min. and slowly cooled to 37° C. Then, 100 units of MuLV reverse transcriptase, buffer (50 mM Tris-HCl, pH 8.3, 8 mM MgCl$_2$, 10 mM dithiothreitol), and 50 nmol dNTP mix were added and reaction mixtures were incubated for 1 h at 37° C. The reaction products were then separated by electrophoresis on a 6% acrylamide gel with 8 M urea and subjected to autoradiography.
2. Results
The 5'-end of the KARP-1 message was determined by primer extension. For these experiments a radiolabeled primer complementary to the 5'-end of Ku86 was utilized. Panel A shows a sequencing reaction which was used to size the primer extended products. Two reproducible, strong bands were observed only in the presence of reverse transcriptase (FIG. 4A). These two bands were mapped to 42 bp and ~400 bp in front of the Ku86 ATG. We inferred that the smaller band corresponds to the mRNA start site of Ku86 whereas the larger band corresponds to the mRNA start site for KARP-1. Panel B shows a schematic of the experimental procedure. This interpretation was consistent with the cloning of the cDNAs for Ku86 (Mimori et al., 1990) and KARP-1 (see below, Example 4). In addition, from this experiment we concluded that KARP-1 and Ku86 were likely to be expressed using different promoters. This hypothesis was confirmed by mapping the genomic structure of the promoter region of the human Ku86 locus (see below, Example 4, FIG. 6) and by an analysis of the KARP-1 cDNA (see below, Example 4, FIG. 5).

Figures 6A, 6B:
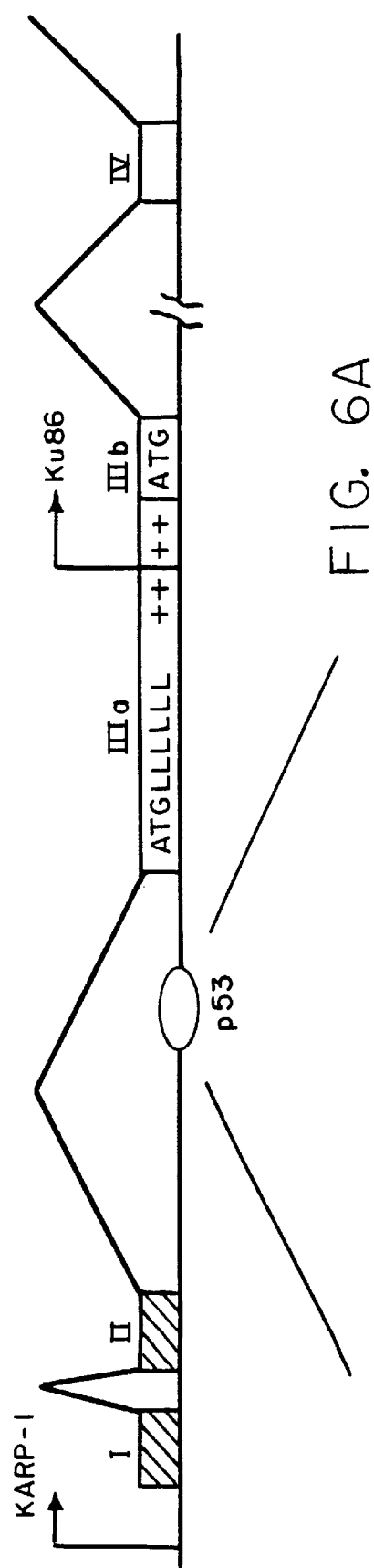
FIG. 6A is a schematic showing the genomic structure of the human Ku86 locus in which the large arrows correspond to the transcriptional start sites for KARP-1 and Ku86, respectively that were mapped by primer extension, the shaded and open rectangles correspond to untranslated and translated exons, respectively, the initiator methionine (ATG) for either KARP-1 or Ku86, and the leucine (L) and the basic (+) residues of KARP-1 are marked and the bent lines correspond to RNA splicing events deduced from cDNA cloning. The oval shows the location of the p53 (and potentially p73) binding site within the second intron of the KARP-1 transcription unit.
FIG. 6B shows the putative p53 response element. The perfect (10 of 10) and the imperfect (8 of 10 and 7 of 10, respectively) p53-binding sites are underlined and the non-consensus nucleotides are shown in lower case.

Example 4
The KARP-1 cDNA and analysis of KARP-1 predicted amino acid sequence reveal the presence of a basic domain and a leucine repeat region.
1. Methods
Isolation of KARP-1 CDNA clones: Partial KARP-1 cDNA clones were obtained using 3'-and 5'-RACE reactions. ALL RACE reactions utilized a Marathon cDNA Amplification Kit (Clontech) and vector primers AP-1 (5'-CCATCCTAATACGACTCACTATAGGGC-3') (SEQ ID NO: 15) and AP-2 (5'-ACTCACTATAGGGCTCGAGCGGC-3') (SEQ ID NO: 16). These primers were utilized in conjunction with four gene-specific primers. 3'-RACE reactions utilized KJI101 (5'-ACGGCGGAATGGAGAGAATGTGCGCATGC-3') (SEQ ID NO:17) and KJI5 (5'-CCTTTCAGGCCTAGCAGGAAACGAAGCGGC-3') (SEQ ID NO:18) while 5'-RACE reactions utilized KJ13 (5'-CGTTTCCTGCTAGGCCTGAAAGGGGC-3') (SEQ ID NO:19) and LZ5E (5'-GCCCGAGCATGCGCACATTCTCTCCA-3') (SEQ ID NO:20) primers. A full-length cDNA was obtained from the same library using KJ007 (5'-GCTGGACCTGGTGGCACACACCTGTGGTCC-3') (SEQ ID NO:21) and KJ008 (5'-GAACTCCCAGCATCACAGCCGATGGCAGCTC-3') (SEQ ID NO:22) for primary PCR and KJ003 (5'-GGGAGACAAGGACCACTGACAAGATA-3') (SEQ ID NO:23) and 86-7 (5'-ATACAGCTGCTGTGTCTCCACTTGG-3') (SEQ ID NO:24) for secondary PCR. PCR products were subdloned into a TA cloning vector (Invitrogen). DNA sequencing was carried out using an automated sequencer and data was obtained for both strands.
2. Results
The KARP-1 cDNA was obtained using 5'- and 3'-RACE reactions and a commercially available (Clontech) human placental cDNA library constructed for PCR cloning. In each case, nested KARP-1-specific PCR primers were utilized in conjunction with nested vector primers. The 3'-RACE product was identical to the published human Ku86 ORF with the exception of five nucleotide changes which resulted in five amino acid changes. The predicted amino acid sequence of KARP-1 is shown in FIG. 5. The two bold methionines (M) correspond to the putative initiator methionines for KARP-1 and Ku86, respectively. The amino acids in lower-case at residues 102, 243, 650, 725 and 746 represent amino acid differences from the published human Ku86 sequence (Mimori et al., 1990). These changes most likely represent simple allelic differences. Sequence analysis of multiple 5'-RACE products revealed that two additional exons are spliced onto the leucine repeat exon, although these did not appear to be expressed as they contained in-frame stop codons and no initiator ATGs. The genomic structure of the human Ku86 locus is shown in FIG. 6A. The large arrows correspond to the transcriptional start sites for KARP-1 and Ku86, respectively that were mapped by primer extension. The shaded and open rectangles correspond to untranslated and translated exons, respectively. The initiator methionine (ATG) for either KARP-1 or Ku86, and the leucine (L) and the basic (+) residues of KARP-1 are shown. The bent lines correspond to RNA splicing events deduced from cDNA cloning. The distance between exon III and exon IV and the total number of Ku86/KARP-l exons is not known. (FIG. 6A).

Ku86 transcription begins 42 bp upstream of the Ku86 ATG, which resides in the exon we have designated as IIIb.

There are no apparent TATA or CAAT box elements upstream of this region, but the region is very GC-rich and contains five consensus binding sites for the transcription factor Sp1 (Dynan and Tijan, 1983). The GC-rich region, which is the presumed promoter for Ku86, is, however, coincident with the KARP-1-specific ORF. The KARP-1 ORF begins at an upstream initiator ATG, located within exon IIIa. Two additional untranslated exons (I and II) are located ~1.4 and 1.2 kb, respectively, upstream from exon III. KARP-1 transcription begins just upstream of exon I.

To confirm the above findings, nested PCR primers corresponding to the 5'-most exon and to the 3'-UTR of Ku86 were constructed. The use of these sets of primers for PCR with a cDNA library as template yielded the expected full-length cDNA, which confirmed that the aforementioned 5'- and 3'-RACE products were indeed physically connected to one another. Therefore, KARP-1 is composed of the leucine repeat region and the basic domain, which together comprise an additional 9 kDa of protein, appended on to the N-terminus of the Ku86 polypeptide (FIG. 5).

Example 5

KARP-1 polypeptide is expressed in human cells and is present at a level significantly lower than Ku86.

1. Methods

Antibody generation and Western blot analysis: A rabbit KARP-1 polyclonal antibody was generated using a KARP-1-specific peptide (N'-GRNLRELGGNLRKLGG-C') (SEQ ID NO:25) conjugated with KLH (Keyhole Limpet hemocyanin) protein (Bio-Synthesis, Inc.). After three boosts, serum was obtained from the rabbit and α-KARP-1-specific antibody was affinity-purified by elution through a CNBr-Sepharose column (Pharmacia) conjugated with the same KARP-1-specific peptide. α-KARP-1 antibody was eluted with glycine-HCl, pH 4.5, neutralized by adding one-hundredth volume of 1 M Tris-HCl, pH 7.0, and then used for further study. For Western blot analyses, the purified antibody was diluted 1 to 100-fold. Western blotting was performed with the ECL system (Amersham) with 20 μg of whole-cell extract in each lane.

Generation of a KARP-1 fusion protein: A KARP-1 fusion protein was generated by using the hexa-histidine; DHFR (dihydrofolate reductase) tag expression system (Qiagen). An ~300 bp PCR fragment containing the KARP-1-specific region was generated using Ming1 (SEQ ID NO:14) and FP (5'-AGATCTAGAGAATGTGCGCATGC-3') (SEQ ID NO:26) primers and then subcloned into the TA vector. The fragment was subsequently removed by digestion with BglII and PvuII and recloned into the pQE41 vector. The induction of the fuision protein was performed according to the manufacturer's protocol.

2. Results

Figures 7A, 7B:
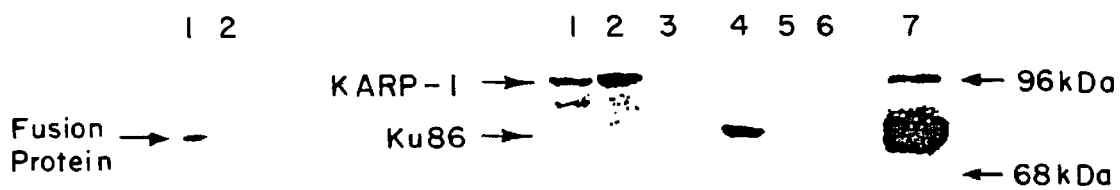
FIG. 7A depicts a Western blot with a α-KARP-1-specific antibody of *E. coli* strains expressing either a hexa-histidine tagged KARP-1-DHFR fusion protein (lane 1) or just the hexa-histidine tagged DHFR protein (lane 2).
FIG. 7B depicts mammalian cell lines prepared from human (lanes 1, 4 and 7) monkey (lanes 2 and 5), and hamster (lanes 3 and 6) cell lines and probed with the α-KARP-1-specific antibody (lanes 1–3) and the human Ku86 monoclonal antibody 111 (lanes 4–6). Lane 7 was probed with the human Ku86 polyclonal antibody 24-4.

A peptide derived from the leucine repeat region of KARP-1 was synthesized and used to generate a rabbit polyclonal α-KARP-1 antibody, which was subsequently affinity purified and used to detect KARP-1 in cellular extracts. The results are presented in FIG. 7. As a control, the antibody preparation was used to perform a Western blot analysis of extracts obtained from an *Escherichia coli* strain producing a 35 kDa fusion protein which consisted of the KARP-1 leucine repeat domain and basic region inserted into a hexa-histidine: DHFR vector. The α-KARP-1 antibody recognized a protein of 35 kDa (FIG. 7A, lane 1) which appeared to be the fusion protein since this protein was not detected in extracts prepared from bacterial cells harboring just the hexa-histidine: DHFR vector (FIG. 7A, lane 2). The antibody preparation was then used to perform an immunoblot analysis of whole-cell extracts prepared from human (lanes 1, 4, and 7), monkey (lanes 2 and 5) and hamster (lanes 3 and 6) cell lines. The α-KARP-1 antibody (lanes 1–3) detected a ~96 kDa protein in both primate extracts (FIG. 7B, lanes 1 and 2), which was in very good agreement with the size (95 kDa) predicted from the KARP-1 cDNA. No signal for KARP-1 could be detected from hamster cell extracts (FIG. 7B, lane 3). As a control, the same blot was re-probed with a monoclonal antibody (mAb111) directed against human Ku86 (shown as lanes 4–6). A strong signal, which was clearly different from the size observed using the α-KARP-1 antibody, at 86 kDa was observed with human cell extracts (FIG. 7B, lane 4). A very weak signal was detected with monkey extracts (FIG. 7B, lane 5), and no signal was observed with hamster extracts (FIG. 7B, lane 6) which suggested that the epitope recognized by antibody mAb111 is not well conserved. The mAb111 antibody did not cross-react with KARP-1 as was predicted from our cDNA sequence. This lack of cross-reactivity was also observed with two additional monoclonal antibodies Ku86. Thus, to confirm these results we obtained a rabbit polyclonal Ku86 sera (Ab24-4) and utilized it in immunoblot analysis of human extracts. This antibody detected not only a protein at 86 kDa, but also one at 96 kDa (FIG. 7B, lane 7), though the level of expression of the latter was several orders of magnitude lower than that of the former. Therefore, the results indicate that: (I) the KARP-1 ORF was indeed translated; (ii) the protein is conserved in primates; and (iii) the level of expression of KARP-1 is significantly lower than that of the abundant Ku86 protein.

Example 6

KARP-1 dominant-negative cell lines have reduced DNA-PK activity and are X-ray-sensitive 1. Methods Cell culture: The HCW-2 cell line was derived from the human promyelocytic leukemia cell line, HL60 (Han et al., 1996). HCW2 cells were cultured in RPMI media (Gibco) and 10% fetal calf serum (Gibco). HeLa (human) and CV-1 (monkey) and cells were grown in DMEM media (Gibco) with 10% fetal calf serum. V79-4 (hamster) cells were grown in α-MEM media (Gibco) with 10% fetal calf serum. Transfection of HCW-2 and HeLa cell lines was achieved by electroporation and included the eukaryotic expression vector SRα containing the N-terminus of KARP-1 and a drug resistance maker, hygromycin (He et al., 1996). Independent hygromycin-resistant colonies were either isolated by limiting dilution (HCW-2) or by toothpicking (HeLa). Individual colonies were expanded and subsequently tested for DNA-PK activity and X-ray survival.

X-ray survival: Cell lines were irradiated with a cesium source (11 Gy/min) at a variety of doses. After irradiation, cells were either replated in 96-well plates (HCW-2 cells and subclones) or onto 100 mm tissue culture plates (HeLa cells and subclones) at defined cell densities. Cells were cultured for 2 weeks and cells surviving to form colonies were counted (Hendrickson et al., 1991).

DNA-PK assays: DNA-PK assays were performed as described (Anderson and Lees-Miller, 1992; Lee et al., 1997). Twenty μg of whole-cell extract was used per DNA-PK assay. Phosphorylation reactions of protein kinase substrates were performed for 8–10 minutes at 30° C. and under the following conditions: pH 7.5, salt 100 mM, 10.0 mM $MgCl_2$, 0.5 mM γ-$^{32}$ATP, 300 μCi/μmol spec. act., 200 mM peptide substrate, 1 mg/ml partially purified DNA-PK (through elution from dsDNA cellulose) and 10 μg/ml dsDNA. The reactions were stopped with SDS-sample buffer and analyzed by SDS-polyacrylamide gel electrophoresis. The specific activity of DNA-PK was calculated as the DNA-PK activity generated with DNA minus the DNA-PK activity generated without DNA.

2. Results

To ascertain the biological role of KARP-1, we attempted to interfere with KARP-1 function in vivo by overexpressing just the 88 amino acids specific to KARP-1. There was significant precedent for this approach as it was known that a number of leucine zipper proteins are negatively regulated by naturally occurring truncated variants which retain the zipper domain, but lack other functional domains (reviewed in Foulkes and Sassone-Corsi, 1992). Thus, this region was subdloned into a mammalian expression vector and stable HCW-2 cell lines expressing this potential dominant-negative version of KARP-1 were isolated. The expression of the transfected DNA, which should result in a ~1.4 kb transcript, was confirmed by Northern hybridization in one of these subclones, Sc5 (FIG. 3A).

Figure 8A:
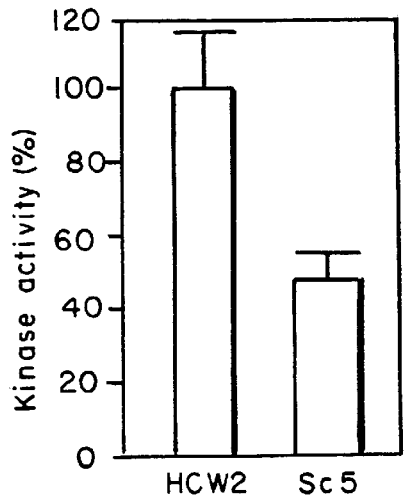
FIGS. 8A–8D show graphs depicting phenotypic information concerning dominant-negative subclones expressing the N-terminus of KARP-1.
Figure 8B:
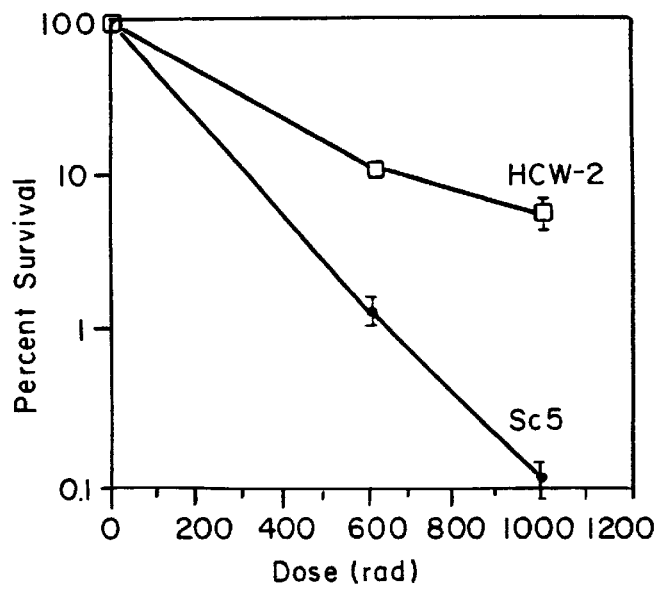
Figure 8C:
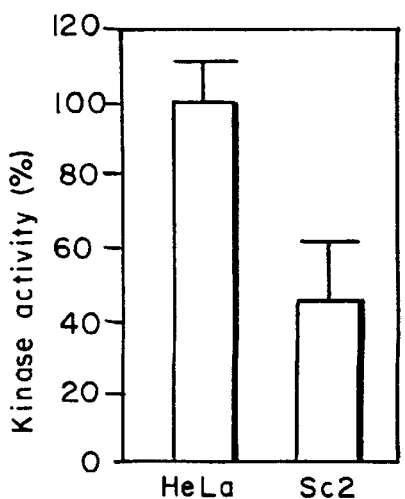
Figure 8D:
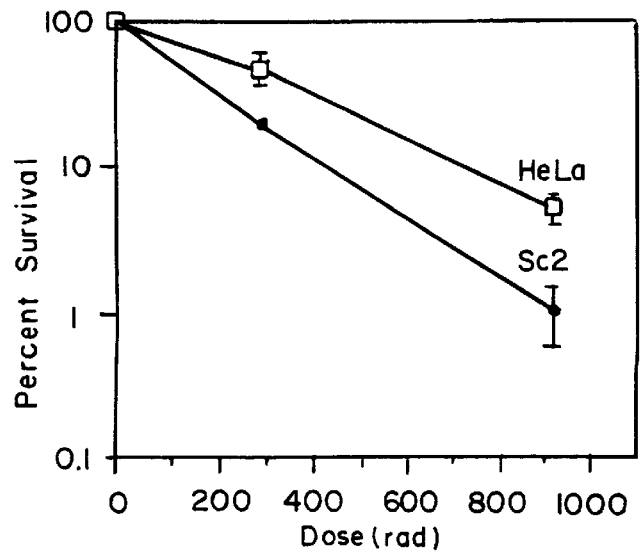

Two subclones, Sc5 and ScD2, were tested for DNA-PK activity. Whole-cell extracts prepared from Sc5 cells showed a 2-fold reduction in DNA-PK activity compared with extracts prepared from HCW2 cells transfected with just a drug-resistance marker (FIG. 8A). The results show the average of three independent experiments. As DNA-PK is known to be involved in the cellular response to X-irradiation (reviewed in Jeggo et al., 1995), we examined the responses of these cells to X-irradiation and observed that the Sc5 cell line was significantly more X-ray-hypersensitive than the parental HCW-2 cells (FIG. 8B). To investigate whether this effect was cell type-specific, we repeated this experiment with HeLa cells. Two HeLa subclones, Sc2 and Sc8, expressing the KARP-1-specific domain also had significantly reduced DNA-PK activity and were X-ray-sensitive (FIG. 8C and D), though the X-ray hypersensitivity was not as severe as observed with Sc5 cells. HCW-2 cells are relatively radioresistant (Han et al., 1995) and this may account for the X-ray hypersensitivity differences between these cell lines. Therefore, the enforced expression of the KARP-1-specific domain resulted in a significant reduction in DNA-PK activity which manifested itself as an X-ray hypersensitivity.

Example 7

α-KARP-1 antibody can neutralize DNA-PK activity in vitro

1. Methods

See examples 5 and 6 above.

2. Results

Figure 9:
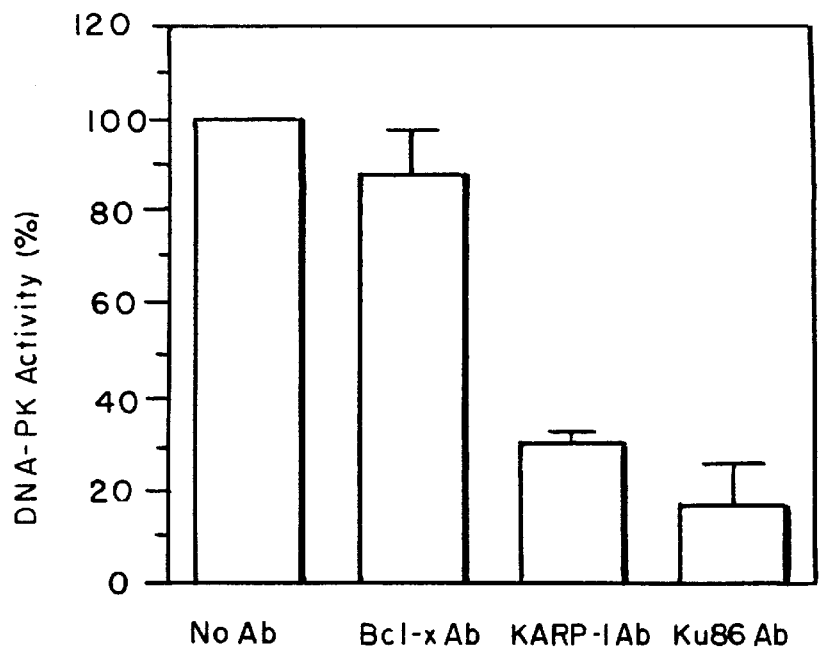
FIG. 9 depicts a DNA-PK assay using an α-KARP-1 antibody in whole-cell extracts prepared from HCW-2 cells, which demonstrates that the α-KARP-1 antibody neutralizes DNA-PK activity in vitro. An irrelevant commercial monoclonal antibody against bcl-x (Transduction Laboratories) and the 111 monoclonal Ku86 antibody were used as controls.

The results of Example 6 suggested that KARP-1 plays a role in DNA-PK activity in human cells. To confirm this, we investigated whether the α-KARP-1 antibody could neutralize DNA-PK activity in vitro. The results are shown in FIG. 9. Whole-cell extracts were prepared from HCW-2 cells and divided into four equivalent aliquots. Subsequently, the aliquots were incubated for 10 min at room temperature with either no antibody, an irrelevant commercial monoclonal antibody against bcl-x (Transduction Laboratories), the polyclonal α-KARP-1 antibody or the 111 monoclonal Ku86 antibody, respectively. DNA-PK assays were then carried out. The results show the average of two independent experiments. The addition of the irrelevant bcl-x antibody did not significantly affect DNA-PK activity in vitro. In contrast, both the α-KARP-1 and α-Ku86 antibodies significantly reduced DNA-PK activity in a dose-dependent fashion. Therefore, neutralization of KARP-1 deleteriously affected DNA-PK activity.

Example 8

Primate-specific conservation of KARP-1

1. Methods

Zoo blotting: A nitrocellulose filter for Zoo blot analysis was purchased from Clontech. Low-stringency hybridization was performed in 20% formamide, 5× Denhardt's solution, 5× SSPE, 0.1% SDS, and 100 μg/ml herring sperm DNA at 42° C. with a 230 bp SacI restriction fragment which encompasses the leucine repeat region of KARP-1. The blot was subsequently stripped by incubating in 0.1× SSC and 0.1 SDS at 94° C. for 30 min. The blot was subsequently reprobed with a 323 bp PsI-ClaI fragment derived from a human Ku86 cDNA.

2. Results

The conservation of KARP-1 was assessed by Zoo blot analysis using a commercially prepared (Clontech) nitrocellulose filter and low-stringency hybridization conditions (FIG. 10). A commercial zoo blot was probed under low-stringency conditions using first a probe specific for the leucine repeat of KARP-1 (A) and then Ku86 (C). The position of fragments which appear to represent specific hybridization to the probes are indicated by asterisks (*). In addition, an ethidium bromide (EtBr) staining profile provided by the manufacturer is shown (B). =Hybridization using a KARP-1 leucine repeat-specific probe (FIG. 10A) resulted in a single strong signal at ~3.5 kb in the lane containing human DNA, though a weaker signal at ~6 kb was also observed. Interestingly, in the lane containing simian DNA, two strong signals, at ~3 kb and 4 kb, were observed. This pattern, of a single hybridization signal with human DNA and two signals with simian DNA was observed in several different blots using different restriction enzymes, suggesting that the leucine repeat region has been duplicated in non-human primates. More interestingly, however, was the lack of any specific hybridization signal with any of the other genomic DNAs (the strong band observed with cow DNA corresponded to a repetitive DNA band observed using ethidium bromide staining (FIG. 10B). To confirm that the genomic DNA in the non-primate lanes was intact, the blot was stripped and rehybridized with a probe specific for Ku86, which is known to be conserved throughout evolution (Mimori et al., 1990; Porges et al., 1990; Paillard and Strauss, 1991; Feldmann and Winnacker, 1993; Jacoby and Wensink, 1994; Boulton and Jackson, 1996; Errami et al., 1996; He et al., 1996; Lee et al., 1996; Milne et al., 1996). As expected, a single strong band of hybridization was observed in all lanes (FIG. 10C), except with yeast DNA, where the level of homology is probably too low to be detected by hybridization (Boulton and Jackson, 1996; Milne et al., 1996). Therefore, the leucine repeat region of KARP-1 may be conserved only in primates.

Example 9

Sequence comparison of human and hamster Ku86 promoter regions

1. Methods

Isolation of hamster Ku86 genomic clones: To clone the promoter region of the hamster Ku86 gene, genomic DNA from the hamster lung V79-4 cell line (Lee et al., 1995) was digested with XbaI and ligated with pbluescript DNA which has been digested with XbaI and NhoI. This ligation mixture was then used for PCR. Primary PCR with carried out with SEL86-2 (5'-AGCTGCCTTATTAGCGGACCACGCCATGTT-3') (SBQ ID NO:27) and a commercially available T7 primer while secondary PCR was performed with SEL86-1 (5'-GCTGGTCCACGGGCGGTTTGGTTACTTTTT-3') (SEQ ID NO:28) and the same T7 primer. All PCR products were subdloned into a TA cloning vector (Invitrogen). DNA sequencing was carried out using an automated sequencer and data was obtained for both strands.

2. Results

To extend the above observation, the promoter region of hamster Ku86 was cloned by PCR and sequenced. The promoter region of hamster Ku86 was cloned and the hamster (Ha) sequence is shown in comparison with the human (Hu) sequence (FIGS. 11A and 11B). Horizontal lines indicate identities and the dots represent gaps introduced into the sequences to obtain an optimal alignment. The bold sequences indicate the initiator ATGs for Ku86 and KARP-1. The predicted amnino acid sequence is shown either above (human) or below (hamster) the DNA sequence and asterisks (*) indicate stop codons. A stop codon was found 27 base pairs upstream of the ATG in the hamster promoter (FIGS. 11A and 11B), suggesting that this region is not expressed in hamsters. Interestingly, the most proximal region of the hamster promoter, which represents the basic domain of KARP-1, was, with the exception of a 17 bp insertion in the corresponding human sequence, quite well conserved between hamsters and humans (FIGS. 11A and 11B). Most importantly, however, upstream of this region, no significant homology between the hamster and human sequences could be discerned. In particular, the leucine repeat region could not be found in the hamster sequence, confirming the Zoo blot analysis (FIG. 10A).Therefore, the KARP-1 expression is likely restricted to primates.

Example 10

Sequence analysis of KARP-1 reveals a p53 binding site

1. Methods

Electrophoretic mobility shift assays were performed as described (Hupp, T. R., D. W. Meek, C. A. Midgley, D. P. Lane, Cell 71, 875 (1992)) except that the gel was electrophoresed at 150 V, 4° C. for 3 hours and the Triton X-100 was omitted from the gel. No complex was observed without the addition of the p53-specific Pab421 (Calbiochem). The probe consisted of a 183 bp PCR fragment which had ben made radioactive using end-labeled primers.

2. Results

Sequence analysis of the KARP-1/Ku86 locus revealed a possible p53 binding site located within the second intron of the KARP-1 gene (FIG. 6B). p53 binding sites consist of multimers of a 10 nt consensus sequence 5'-PuPuPuC(A/T) (A/T)(GPyPyPy-3' (SEQ ID NO:29) with the multimers separated by 0–13 nt (W. S. Deiry, et al., 1992, Nat. Genet, 1:45; W. D. Funk, et al., 1992, Mol. Cell. BioL, 12:2866; Y. Wang, et al., 1995, ibid., 15:2157). The KARP-1 p53 binding site consisted of a perfect consensus 10-mer separated by 9 and 10 nt, respectively, from two imperfect (8 and 7 matches, respectively) sequences shown consecutively in FIG. 6B and the non-consensus nucleotides are shown in lower case. The location of the putative site, within the second intron of KARP-1, was similar to the location of known functional p53 binding sites for the cyclin G (A. Zauberman, et al., 1995, Oncogene, 10:2361), IGF-BP3 (L. Buckbinder, et al., 1995, Nature, 377:646) and MDM2 (A. Zauberman, 1995, Nucleic Acids Res., 23:2584) genes.

Figure 12:
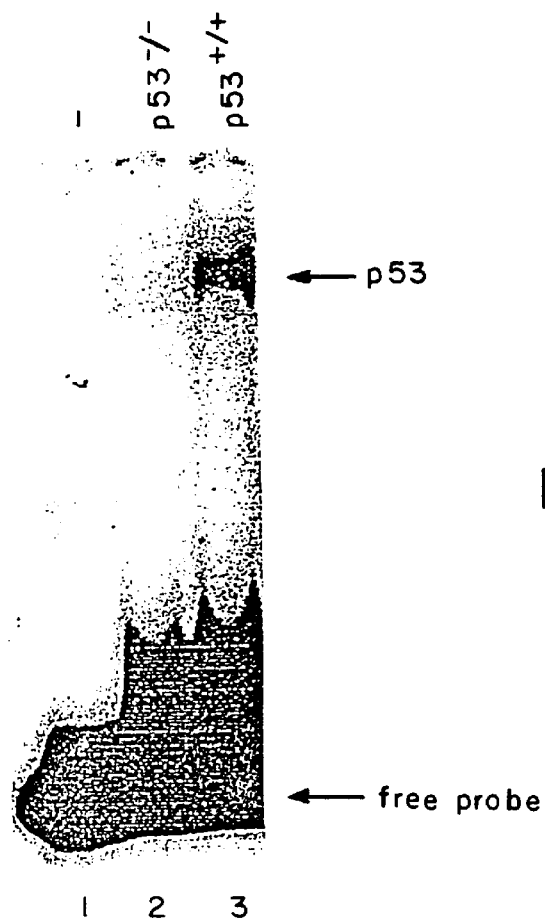
FIG. 12 shows a gel mobility assay demonstrating that p53 can bind to the putative KARP-1 p53-response element. Whole cell extracts were prepared from HCW-2 (lane 2, p53$^{-/-}$) and HCT116 (lane 3, p53$^{+/+}$), cells combined with a 183 bp probe containing the putative KARP-1 p53-response element in the presence of the p53-specific antibody, pAb421, and subjected to a gel mobility-shaft assay. Lane 1 shows the probe incubated without cellular extract.

A 183 base pair probe containing the p53 binding site was utilized in a gel mobility-shift assay to deterrnine if p53 can bind to the putative KARP-1 p53-response element. Whole cell extract prepared from HCT116 cells (p53$^{+/+}$) contained an activity that retarded the mobility of the fragment in a polyacrylamide gel (FIG. 12, lane 3). The presence of the complex was completely dependent upon the inclusion of the p53-specific Pab421. No complex was detected when nuclear extracts were prepared from HCW-2 cells (p53$^{-/-}$) (FIG. 12, lane 2). Lane 1 shows the probe incubated without cellular extract. Thus, a functional p53 binding site exists within the KARP-1 second intron.

Example 11

KARP-1 expression is DNA-damage inducible

1. Methods

Plates of cells were X-irradiated using a $^{137}$Cs source at a dose rate of 11.1 Gy/min. Total RNA was then isolated and 20 μg was used for first strand synthesis with MuLV reverse transcriptase (NEB) as described (A. Zauberman, et al., 1995, Oncogene, 10:2361). The synthesized first strand was then used as a template for the PCR reaction. The KARP-1 PCR primers were 5'-ACGGCGGAATGGAGAGAATGTGCGCATGC-3' (SEQ ID NO:17) and 5'-AACAGCTGCCTTATTCCCCGACCGCACCAT-3' (SEQ ID NO:9). The β-actin PCR primers were 5'-ATCTGGCACCAGACCTTCTACAATGAGCTGCG-3' (SEQ ID NO:31) and 5'-CGTCATACTCCTGCTTGCTGATCCACATCTGC-3' (SEQ ID NO:32). The Ku86 PCR primers were 5' CTGTTGTGCTGTGTATGGACGTGGG-3' (SEQ ID NO:33) and 5'-CCAGGAAGTCAGCCTGTTGAGAACC-3' (SEQ ID NO:34). KARP-1 RT-PCR products were hybridized with a 328 bp KARP-1 specific probe generated by PCR (K. Myung, et al., 1997, EMBO J., 16:3172). Ku86 RT-PCR products were hybridized with a 200 bp Ku86 specific probe generated by PCR with radiolabeled Ku86 PCR primers. β-actin RT-PCR products were either analyzed on EtBr-stained gels or were hybridized with a β-actin gene fragment (Clontech).

2. Results

Figure 13A:
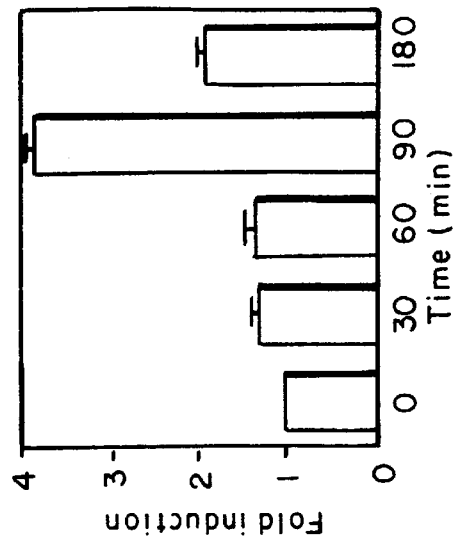
FIGS. 13A–13D demonstrate that KARP-1 gene expression is induced in a dose-dependent manner following X-irradiation.
Figure 13B:
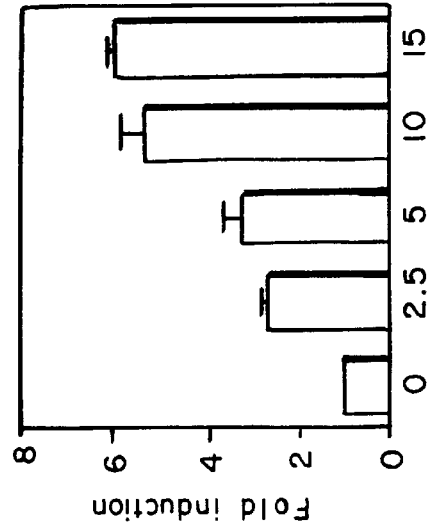
Figure 13C:
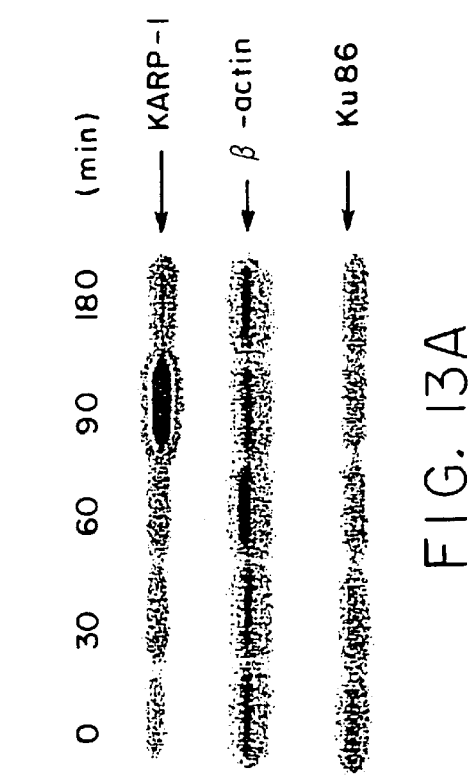
Figure 13D:
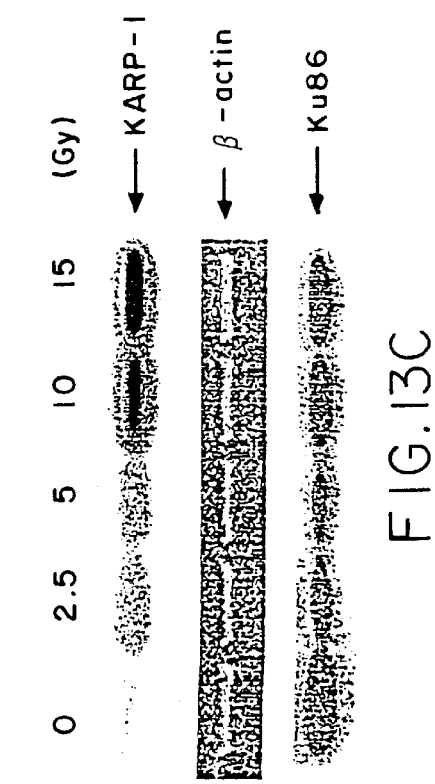

The immortalized human diploid fibroblast cell line, HCTl 16, was utilized to investigate whether KARP-1 gene expression could be stimulated by X-irradiation since these cells have been shown to be normal in their response to ionizing radiation (T. Waldman, et al., 1995, Cancer Res., 55:5187; T. Waldman, et al., 1996, Nature, 381:713; Z. Han, et al., 1996, Cancer Res. 1996, 56:1621). The immortalized human diploid fibroblast cell line, HCT116, was utilized since these cells have been extensively characterized and shown to be completely normal in their response to ionizing radiation. KARP-1 message level was quantitated by an RT-PCR/Southem blot analysis after exposure of the HCT116 cell line to 10 Gy of X-irradiation. As controls, β-actin and Ku86 RT-PCR/Southem reactions were also performed. The fold-induction of KARP-1 mRNA was quantitated using β-actin levels as a reference (shown in FIG. 13 B and D). The average of two independent experiments is shown and the error bars represent the standard deviation. Strong induction (4-fold) of KARP-1 mRNA was observed at 90 min after X-irradiation (FIG. 13A). HCT116 cells were subsequently X-irradiated using different doses and at 90 min post-irradiation the KARP-1 message level was determined (FIG. 13 C). KARP-1 MRNA induction was dose dependent with a 6-fold stimulation at the highest dose (15 Gy) tested and a reproducible 2-fold induction even at the lowest dose (2.5 Gy) tested. Ku86 message levels did not increase following X-irradiation at any dose or time tested (FIG. 13 A and C). For the β-actin sample only the EtBr-stained gel is shown. These results demonstrated that KARP-1 expression was DNA damage inducible, whereas Ku86 was not.

Example 12
Induction of KARP-1 mRNA requires a functional p53 gene product
1. Methods Methods for X-irradiation of cells and RT-PCR are described above.

2. Results

Figure 14A:
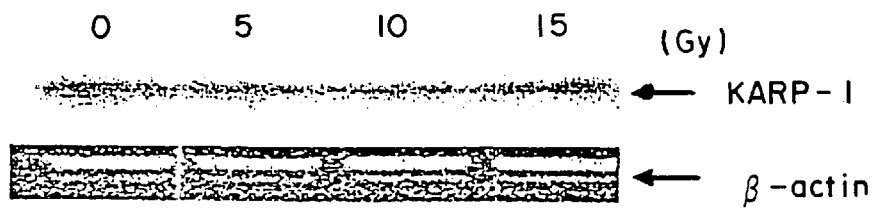
FIGS. 14A–14E demonstrate that KARP-1 induction is dependent upon functional p53 and ATM gene products.
Figure 14B:

The status of KARP-1 mRNA induction in human cell lines defective for p53 function was next examined. HCW2 cells are a HL-60 subclone which are known to be deficient in p53 due to a deletion of the gene (Z. Han, et al., 1996, Cancer Res., 56:1621). HeLa cells contain a wild-type p53 gene, but its function, inclusive of almost all DNA damage responses, is seriously impaired because they have been infected with a human type-18 papillomavirus (M. Scheffner, et al., 1990, Cell, 63:1129; B. Werness, et al., 1990, Science, 248:76). HCW-2 (p53$^{-/-}$)(FIG. 14A) and HeLa (p53-defective)(FIG. 14B) cell lines were X-irradiated at the indicated doses and at 90 min post-irradiation RT-PCR reactions (β-actin) followed by Southern hybridizations (KARP-1). HCW2 and HeLa cells showed no induction of KARP-1 message 90 min after exposure to various doses of X-irradiation. In addition, no induction was observed at earlier (30 and 60 min) or later (180 min) times post-irradiation. Therefore, the induction of KARP-1 message appeared to require a functional p53 gene product.

Example 13
Induction of KARP-1 mRNA requires a functional ATM gene product following DNA damage
1. Materials and Methods ATM$^{-/-}$ cell lines, GM08436A and GM01526E, and the ATM$^{+/+}$ cell line, GM00130C, were purchased from the NIGMS Human Genetic Mutant Cell Repository at the Coriell Intitute for Medical Research.

Methods for X-irradiation of cells and RT-PCR are described above.

2. Results

Figure 14C:
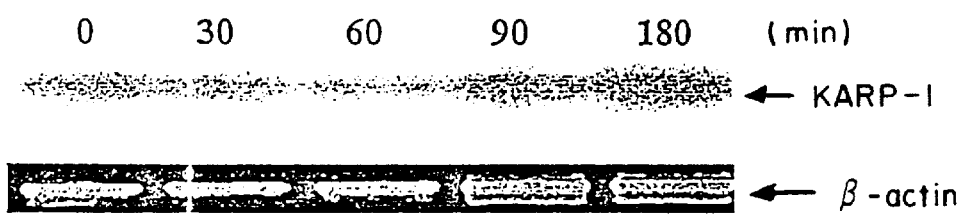
Figure 14D:
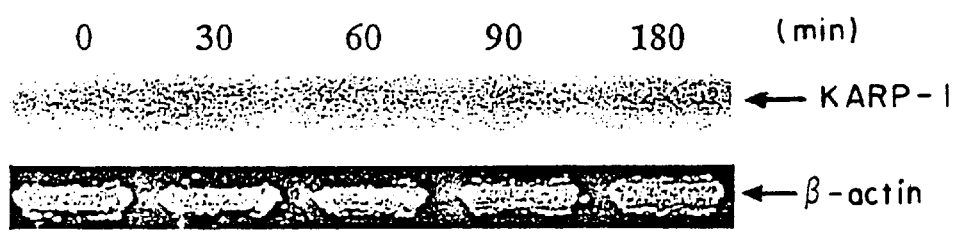
Figure 14E:
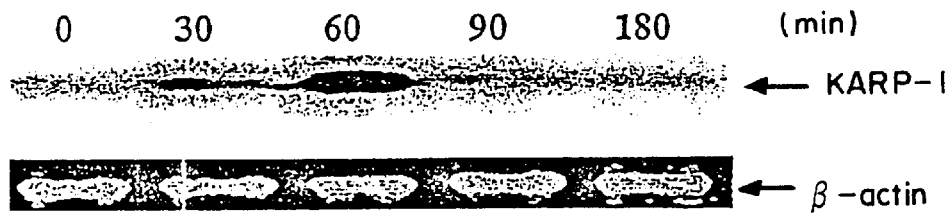

The requirement for the ATM gene product in KARP-1 induction was investigated since ATM is thought to lie upstream of p53 in the DNA damage signal transduction pathway (M. Lavin, et al., 1996, Curr. Opin. Immunol., 8:459; A. Levine, 1997, Cell, 88:323). GM08436A (ATM$^{-/-}$)(FIG. 14C), GM01526E (ATM$^{-/-}$)(FIG. 14D) and GM00130C (ATM$^{+/+}$ )(FIG. 14E) cells (23) were X-irradiated at 10 Gy and at the indicated times post-irradiation RT-PCR reactions (β-actin) followed by Southern hybridizations (KARP-1) were performed. GM08436A and GM01526E AT cells, which were derived from independent AT patients, exhibited no KARP-1 induction following X-irradiation with 10 Gy. Since these cell lines were of lymphoblastoid origin and the original demonstration of KARP-1 inducibility was carried out with HCT 16 fibroblastic cells (FIG. 13) a lymphoblastoid cell line (GM00130C) derived from a wild-type individual was also examined. KARP-1 was induced (6-fold) in GM00130C cells, though the time of induction was 30 min faster than in HCT116 cells. Thus, a wild-type ATM gene product was required for KARP-1 mRNA induction following DNA damage.

Example 14
Localization of KARP-1 shifts from cytoplasm to nucleus following X-irradiation
1. Methods HCT116 cells were X-irradiated with 10 Gy and at the indicated times post-irradiation nuclear and cytoplasmic extracts were prepared and then subjected to immunoblot analysis using a KARP-1 polyclonal antibody.

Cells were lysed with 0.05% NP-40 in 10 mM Tris-HCl, pH 7.4, 10 mM NaCl, 3 mM MgCl$_2$. After 10 min at 0° C., cytoplasmic extract was obtained by centrifugation at 14,000 rpm for 5 sec. The pellet (nuclei) was washed with 10 mN Tris-HCl, pH 7.4, 10 mM NaCl$_2$ once and lysed with 20 mM HEPES, pH 7.4, 0.42 M NaCl, 1.5 mM MgCl$_2$, 0.2 mM EDTA, and 25% glycerol using 8 strokes through a 21G needle. After 30 min nuclear extract was obtained by centrifugation at 14,000 rpm for 5 min. Protein was quantitated using the Bradford assay (Biorad) and 50 μg was used for each lane in a 7.5% SDS-PAGE gel. Immunoblotting was performed with the ECL system (Amersham) and the following antibodies: α-KARP-1 rabbit polyclonal antibody (13), α-Ich-1$_L$ mouse monoclonal antibody (Transduction Laboratories) and a α-USF rabbit polyclonal antibody (Santa Cruz Biotechnology Co.).

2. Results

Figure 15:
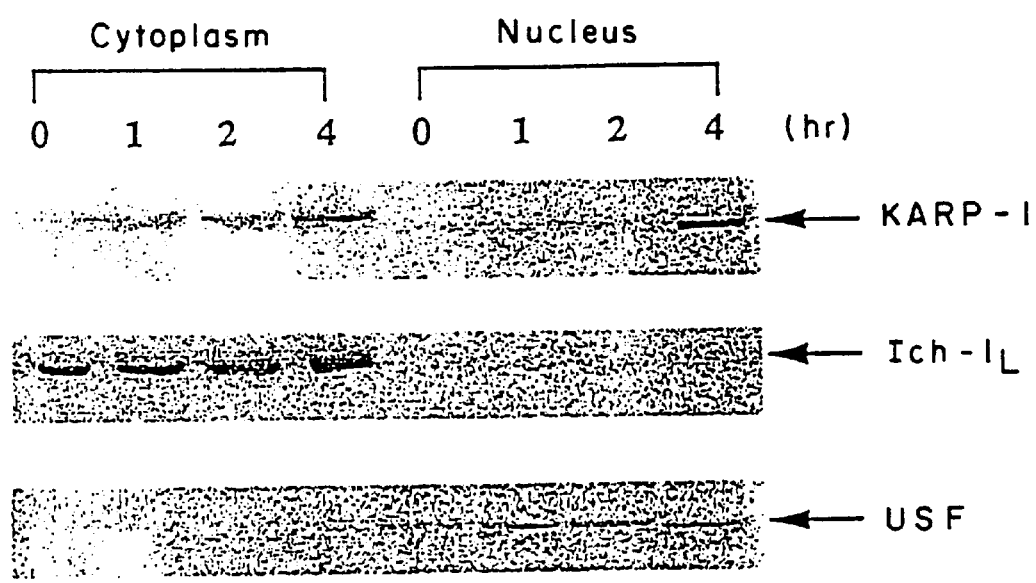
FIG. 15 demonstrates that KARP-1 protein is induced and undergoes nuclear translocation following X-irradiation. HCT116 cells were X-irradiated with 10 Gy and at the indicated times post-irradiation nuclear and cytoplasmic extracts were prepared and then subjected to immunoblot analysis using a KARP-1 polyclonal antibody. Subsequently, the blot was stripped and probed with an antibody for Ich-1$_L$ and then USF.
Figure 16A:
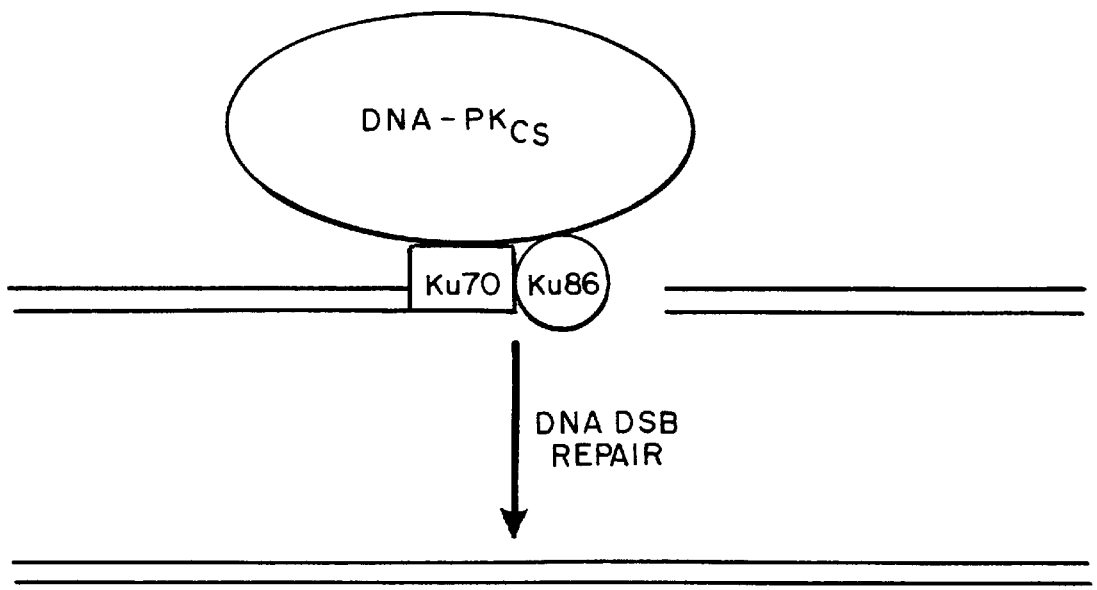
FIGS. 16A–16D depict several models for KARP-1 regulation of DNA-PK. FIG. (16A) is a cartoon showing the previously accepted model of DNA-PK. FIG. (16B) shows that KARP-1 may replace Ku86 in some of the DNA-PK complexes. FIG. (16C) KARP-1 may associate with the other three components of DNA-PK and alter or augment the activity of DNA-PK. FIG. (16D) KARP-1 may provide a new DNA binding subunit for DNA-PK$_{cs}$ which may result in novel activities such as transcription, DNA replication or chromatin reorganization.
Figure 16B:
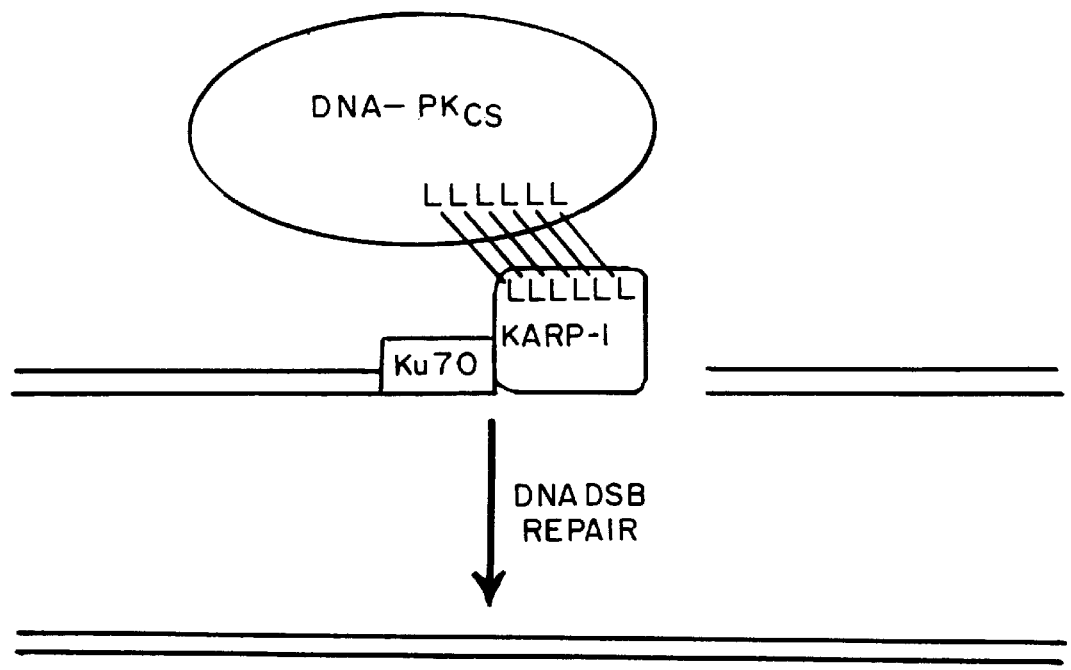
Figure 16C:
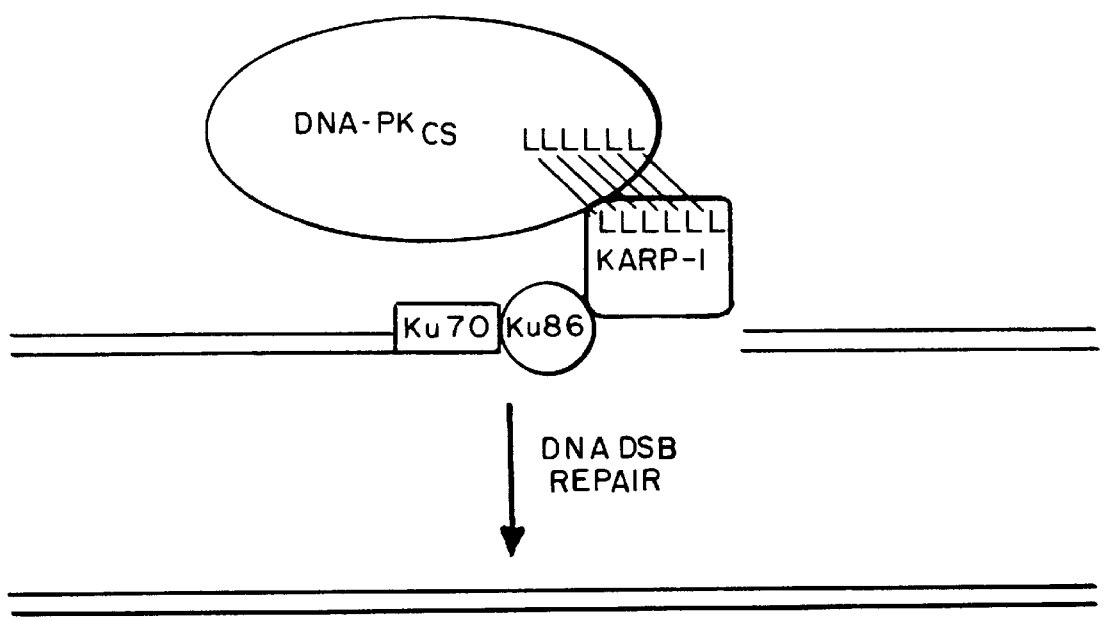
Figure 16D:
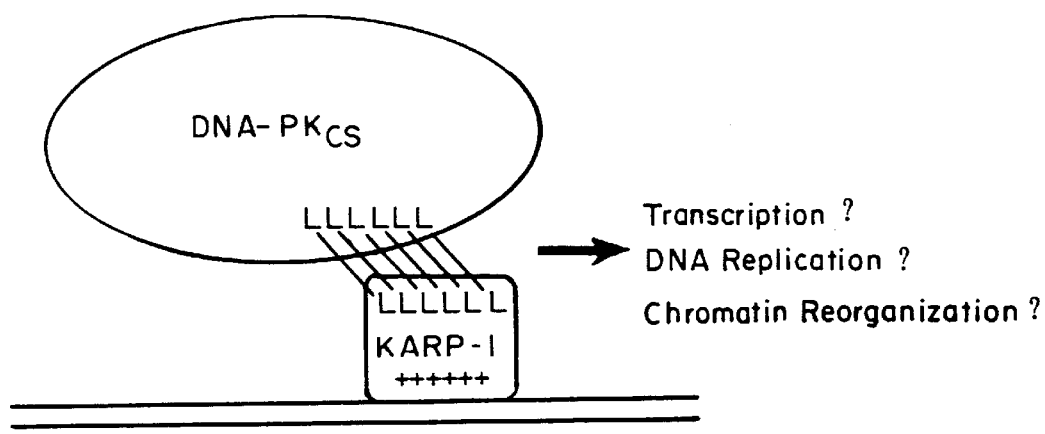

Next, cytoplasmic and nuclear extracts were prepared from HCT116 cells at various times after X-ray exposure and analyzed by Western hybridization. Before X-irradiation, KARP-1 protein was found predominantly in the cytoplasmic fraction (FIG. 15). Following X-irradiation, the amount of KARP-1 protein increased over time and by 4 hr post-irradiation the majority of KARP-1 was found in the nuclear fraction. This blot was stripped and then sequentially re-probed with antibodies for the cytoplasm protein, Ich-1$_L$ (caspase-2), and the nuclear protein, USF, to control for the cellular fractionation and to show that the induction was specific for KARP-1 protein (FIG. 15). Thus, KARP-1 is predominately a cytoplasmic protein whose expression levels increased, and whose cellular location was altered, following DNA damage.

Each of the foregoing patents, patent applications and references is hereby incorporated by reference. While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

I claim:

1. An isolated KARP-1 nucleic acid molecule which hybridizes under stringent conditions to a molecule consisting of the nucleic acid sequence selected from the group consisting of SEQ. ID. NO: 1 and SEQ. ID. NO: 35 and which codes for a polypeptide which has KARP-1 activity.

2. The isolated KARP-1 nucleic acid molecule of claim 1, wherein the KARP-1 nucleic acid molecule is selected from the group consisting of SEQ ID NO:1 and SEQ ID NO:35.

3. An isolated KARP-1 nucleic acid molecule which is a unique fragment of SEQ ID NO:1 or SEQ ID NO:35.

4. The isolated KARP-1 nucleic acid molecule of claim 3, wherein the unique fragment excludes sequences consisting of only SEQ ID NO:3.

5. The isolated KARP-1 nucleic acid molecule of claim 3, wherein the unique fragment includes at least one sequence encoding a leucine zipper domain of SEQ ID NO:4.

6. The isolated KARP-1 nucleic acid molecule of claim 3, wherein the unique fragment includes at least 10 contiguous nucleotides of the p53 binding site of SEQ ID NO:30.

7. The isolated KARP-1 nucleic acid molecule of claim 3, wherein the nucleic acid molecule consists of at least 14 contiguous nucleotides.

8. The isolated KARP-1 nucleic acid molecule of claim 3, wherein the nucleic acid molecule consists of at least 15 contiguous nucleotides.

9. The isolated KARP-1 nucleic acid molecule of claim 3, wherein the nucleic acid molecule consists of at least 16 contiguous nucleotides.

10. The isolated KARP-1 nucleic acid molecule of claim 3, wherein the nucleic acid molecule consists of at least 17 contiguous nucleotides.

11. The isolated KARP-1 nucleic acid molecule of claim 3, wherein the nucleic acid molecule consists of at least 18 contiguous nucleotides.

12. The isolated KARP-1 nucleic acid molecule of claim 3, wherein the nucleic acid molecule consists of at least 20 contiguous nucleotides.

13. The isolated KARP-1 nucleic acid molecule of claim 3, wherein the nucleic acid molecule consists of at least 22 contiguous nucleotides.

14. The isolated KARP-1 nucleic acid molecule of claim 3, wherein the nucleic acid molecule consists of between 12 and 32 contiguous nucleotides.

15. An expression vector comprising the isolated KARP-1 nucleic acid molecule of claims 1, 2, 3 ,4, 5, 6, 7, 8, 9, 10, 11, 12 or 13 operably linked to a promoter.

16. A host cell transformed or transfected with the expression vector of claim 15.

* * * * *

UNITED STATES PATENT AND TRADEMARK OFFICE
CERTIFICATE OF CORRECTION

PATENT NO. : 6,171,857 B1
DATED : January 9, 2001
INVENTOR(S) : Eric A. Hendrickson It is certified that error appears in the above-identified patent and that said Letters Patent is hereby corrected as shown below:

Column 88,
Line 63, delete "or 13" and insert therefor -- , 13 or 14 --.

Signed and Sealed this

Tenth Day of December, 2002

JAMES E. ROGAN
*Director of the United States Patent and Trademark Office*

SEQUENCE LISTING

<160> NUMBER OF SEQ ID NOS: 35

<210> SEQ ID NO 1
<211> LENGTH: 6078
<212> TYPE: DNA
<213> ORGANISM: Homo Sapiens

```
<220> FEATURE:
<221> NAME/KEY: unsure
<222> LOCATION: (178)...(178)
<221> NAME/KEY: unsure
<222> LOCATION: (230)...(230)
<221> NAME/KEY: unsure
<222> LOCATION: (232)...(232)
<221> NAME/KEY: unsure
<222> LOCATION: (234)...(234)
<221> NAME/KEY: unsure
<222> LOCATION: (453)...(453)
<221> NAME/KEY: unsure
<222> LOCATION: (473)...(473)
<221> NAME/KEY: unsure
<222> LOCATION: (610)...(610)
<221> NAME/KEY: unsure
<222> LOCATION: (612)...(612)
<221> NAME/KEY: unsure
<222> LOCATION: (2175)...(2175)
<221> NAME/KEY: unsure
<222> LOCATION: (1014)...(1014)

<400> SEQUENCE: 1
gaattcggct tactataggg cacgcgtggt cgacggcccg ggctggtctg aaatgcaaac      60
aagcacagct actaaaacct cttttatttc ttccaaaaaa cagacctgta ctgaagggtg     120
tatggaaaac agagagtggg gacagggaga aggaaaagaa gggggaggag gaggagcngg     180
aggaaaagga aggggaaaac caagagggag ggagggaagg aggaagggan ananagagag     240
aaaggaagag gaaaaatwga caccatatac aagataaaaa catggacata aagcatgcaa     300
atttccttca cagtactgas tctccagtaa ttctctttac cagtcttatt ggrraaatat     360
tttttaggct gagcgcggtg gatcacatct gttmtcccac cactttggga rgctgakgtg     420
ggcsgatcac ctgawgtcwg gagttcgaga ccngcctggc caacatggca aantcccstc     480
tctactaaaa atacaaaaat tasccsgcac agtggtgggt gcctatamtc ccasctactt     540
ggtaagctga cgcaggaaaa tcgcttgagc ctggtggcgg gtgggagcgg cggaagtttg     600
tattgagccn anatcttgcc actgcactcc asccngggcg casagtgaga ctgttctcaa     660
aaaaagagg gtatcagggt acattatctc cacatgctga taagttgtta cataagtcca     720
ccmattcaca atttaatatc atatactcta cccactcmaa ttttcastct ttcmmagcac     780
attaacmaag ttatcaggaa aatgggacta gcacaaccaa agatgttaca gactgcacac     840
aattttgaca cggatacaac gtgaccaagg agtggttttc ttcaggaaac aattctacta     900
aaaaaccca tgaaaataaa agtaatttaa aatttttcaag acacattaaa tgcatgactg     960
tggctctata ttgccatttg tatgcgctgt actgtaggaa ataaaatacc ctcncctag    1020
ggaatgttaa actgacttcg aagacagtga aagcctccca ttgttcacta tttcagtgtt    1080
tcctggttgt accaaacaac aaacaagtga attatttcac cttttaaaag ctacacttta    1140
aaatgggat aaagtgggat tccctccttc ctaaaaatgt ttcagccagg cacaggctca    1200
cgcctgtaag gccagtactt tgggaggtca aggtgggcgg attacctgag gtcgggagtt    1260
cgagaccagc ctgaccaaga tggagaaacc ccatctctac gaaaaataca aaattagctg    1320
ggtgtggtgg cacatgcctg taatcccagc tacttgggag gctgaagcag gagaatcgct    1380
tgaacccggc aggcggaggt tgccgtaagc agaattcgcg ccactacact ccagcctggg    1440
caacaagagg gaaactctgt ctcaaaaaaa aaaaaaaaaa gtttctacag ctactaaaaa    1500
acttgcattt aaaatagtt gataaaaata ttccttatca aaatagttga taaaatatt    1560
cctctgaggc caagtgcagt tgctcacacc tgtcatccca gcactttggg aggckkaagc    1620
gggaggatcg cttgatccca ggagttcaag accaggctgg gcaacatagg aagacccccg c  1680
```

```
ctccacacac acagaaaccc cacaaaaatt agctgggctt ggtggcacac actgtggtcc    1740
cagctacctg ggaggctgag gtaagtgaat gcttgagccc aggggttcca ccctgcagag    1800
agctatgatt gtgctactgg actccagcct cggccgagcg acaccctgtc tgtttctttc    1860
cttttctctc tctccctagc tctggatcgt acaagaaggg agacaaggac cactgacaag    1920
atatggtatg tgatactaat cagatttggc ttctttctgt cctgcttcac agaagctgg    1980 actctccttg tttcagtttc tccgcttttcc acagataaat cttttgtttc ccggatagcc    2040
acttggcctg tttgcccttt cgtcccattt ttccttgttt gcttctttgt ctgaaaattt    2100
atgctgtcct gctgcctccg ctgggcttcg tttccacctt tgctggagga gatttaactg    2160
acaacctcac agatnttccc cgccccttct gccgaactga tctttctctt gggaaatctt    2220
acccccacgg aaagggctag tgtccgtgcc tgcctgcctg cctgctgcag cccgcgcaaa    2280
gctgagcggc aagggcgct gctgttcctt taaagtatta ttaaaaataa tatttcagct    2340
tttaagtaac tccttgagtt tgaatcaaaa gctggaagaa cctcctgggc tctatgagca    2400
cctctgaata tgtctgactc tacattctag aggcttcaat atatttataa ttttggctca    2460
tagattctcc acatcttttc agcttcaatt cttgcttttc ccagaaacaa ttttcaagca    2520
ggagagaata ttgattggac ttgattttct cagtttgggc agaggtttgc agacactttg    2580
caggttgcca gacccttcgt ccagccaccc gtcagctggg ggtcatatgg tatagaaagc    2640
agtcatttct atgcaaggta ctgcttgggc ctgcctccct caaagggta ggggatgcgg    2700 gctggacaaa gggctcgtga tcaagtaaag cactgtgatg acagctgcta tttctatatc    2760
tccctagact tgtcttctaa attaaacctt gactcctccc ttccaagctg gagccactgc    2820
taactactgg gagagcctta gcagataaag tctcatgcct ccaggcgttt gtgcatccca    2880
ttttctctgc agagtagaat ctcccttcta cttttgtgct cctggggacg tcctactctt    2940
cttccccagt tggctctaag gttatcacat cggtgaagtg tttcattatc acttttttaga    3000 agaaactgag tcttttagag aagttaagtg actttctcga ttcatactca tactcaagaa    3060
aatctaactc cacaataacc aaaaataaaa agtagaaaaa aacccacaag tgatgagaaa    3120
aaaaaaaaaa tcaaaagtta taaaaataa atgaaaaaat gaaattaaag gaaaaaagat    3180
tttttaaaaa agtaaaaaaa agaaaagaaa tctaactcca gagctctgac acaaaatgcc    3240
ttaggtgtta ttctcaatga gagaaaaggg acgtgaatct ttaagtgatt aagtgaatct    3300
ttaagtaaat ctgtcgtact agcgtttcag gcggctcaaa caccacacgc ccccgactac    3360
ggcggaatgg agagaatgtg cgcatgctcg gcgggaatct gcgcatgctc ggagagaatc    3420
tgcgcatgct cggccggaat ctgcgcgagc tcggcgggaa tctgcgcaag ctcggcggga    3480
atctgcgcat gctcagagtt ccggggcacg gtttccccgc cctttcagg cctagcagga    3540 aacgaagcgg ctctttccgc tatctgccgc ttgtccaccg gaagcgagtt gcgacacggc    3600
aggttcccgc ccggaagaag cgaccaragc gcctgaggac cggcaacatg gtgcggtcgg    3660
ggaataaggc agctgttgtg ctgtgtatgg acgtgggctt taccatgagt aactccattc    3720
ctggtataga atccccattt gaacaagcaa agaaggtgat aaccatgttt gtacagcgac    3780
aggtgtttgc tgagaacaag gatgagattg ctttagtcct gtttggtaca gatggcactg    3840
acaatcccct ttctggtggg gatcagtatc agaacatcac agtgcacaga catctgatgc    3900
taccagattt tgatttgctg gaggacattg aaagcaaaat ccaaccaggt tctcaacagg    3960
ctgacttcct ggatgcacta atcgtgagca tggatgtgat tcaacatgaa acaataggaa    4020
```

```
agaagtttga gaagaggcat attgaaatat tcactgacct cagcagccga ttcagcaaaa    4080
gtcagctgga tattataatt catagcttga agaaatgtga catctccctg caattcttct    4140
tgcctttctc acttggcaag gaagatggaa gtggggacag aggagatggc ccctttcgct    4200
taggtggcca tgggccttcc tttccactaa aaggaattac cgaacagcaa aagaaggtc     4260
ttgagatagt gaaaatggtg atgatatctt tagaaggtga agatgggttg gatgaaattt    4320
attcattcag tgagagtctg agaaaactgt gcgtcttcaa gaaaattgag aggcattcca    4380
ttcactggcc ctgccgactg accattggct ccaatttgtc tataaggatt gcagcctata    4440
aatcgattct acaggagaga gttaaaaaga cttggacagt tgtggatgca aaaccctaa     4500
aaaaagaaga tatacaaaaa gaaacagttt attgcttaaa tgatgatgat gaaactgaag    4560
ttttaaaaga ggatattatt caagggttcc gctatggaag tgatatagtt cctttctcta    4620
aagtggatga ggaacaaatg aaatataaat cggaggggaa gtgcttctct gttttgggat    4680
tttgtaaatc ttctcaggtt cagagaagat tcttcatggg aaatcaagtt ctaaaggtct    4740
ttgcagcaag agatgatgag gcagctgcag ttgcactttc ctccctgatt catgctttgg    4800
atgacttaga catggtggcc atagttcgat atgcttatga caaaagagct aatcctcaag    4860
tcggcgtggc ttttcctcat atcaagcata actatgagtg tttagtgtat gtgcagctgc    4920
ctttcatgga agacttgcgg caatacatgt tttcatcctt gaaaaacagt aagaaatatg    4980
ctcccaccga ggcacagttg aatgctgttg atgctttgat tgactccatg agcttggcaa    5040
agaaagatga gaagacagac acccttgaag acttgtttcc aaccaccaaa atcccaaatc    5100
ctcgatttca gagattattt cagtgtctgc tgcacagagc tttacatccc cgggagcctc    5160
taccccaat tcagcagcat atttggaata tgctgaatcc tcccgctgag gtgacaacaa     5220
aaagtcagat tcctctctct aaaataaaga ccctttttcc tctgattgaa gccaagaaaa    5280
aggatcaagt gactgctcag gaaatttttcc aagacaacca tgaagatgga cctacagcta    5340
aaaaattaaa gactgagcaa ggggagccc acttcagcgt ctccagtctg gctgaaggca    5400
gtgtcacctc tgttggaagt gtgaatcctg ctgaaaactt ccgtgttcta gtgaaacaga    5460
agaaggccag ctttgaggaa gcgagtaacc agctcataaa tcacatcgaa cagttttgg     5520
atactaatga aacaccgtat tttatgaaga gcatagactg catccgagcc ttccgggaag    5580
aagccattaa gttttcagaa gagcagcgct ttaacaactt cctgaaagcc cttcaagaga    5640
aagtggaaat taacaatta atcattttct gggaaattgt tgtccaggat ggaattactc     5700
tgatcaccaa agaggaagcc tctggaagtt ctgtcacagc tgaggaagcc aaaaagtttc    5760
tggccccaa agacaaacca agtggagaca cagcagctgt atttgaagaa ggtggtgatg    5820
tggacgattt attggacatg atataggtcg tggatgtatg gggaatctaa gagagctgcc    5880
atcgctgtga tgctgggagt tctaacaaaa caagttggat gcggccattc aaggggagcc    5940
aaaatctcaa gaaattccca gcaggttacc tggaggcgga tcatctaatt ctctgtggaa    6000
tgaatacaca catatatatt acaagggata atttagaccc catacaagtt tataaagagt    6060
cattgttaaa aaaaaaaa                                                  6078
```

<210> SEQ ID NO 2
<211> LENGTH: 820
<212> TYPE: PRT
<213> ORGANISM: Homo Sapiens

<400> SEQUENCE: 2

Met Leu Gly Gly Asn Leu Arg Met Leu Gly Glu Asn Val Arg Met Leu

```
  1               5                 10                15
Gly Arg Asn Leu Arg Glu Leu Gly Gly Asn Leu Arg Lys Leu Gly Gly
                20                25                30

Asn Leu Arg Met Leu Arg Val Pro Gly His Gly Phe Pro Ala Pro Phe
                35                40                45

Arg Pro Ser Arg Lys Arg Ser Gly Ser Phe Arg Tyr Leu Pro Leu Val
 50              55                60

His Arg Lys Arg Val Ala Thr Arg Gln Val Pro Ala Arg Lys Lys Arg
 65              70                75                80

Pro Lys Arg Leu Arg Thr Gly Asn Met Val Arg Ser Gly Asn Lys Ala
                85                90                95

Ala Val Val Leu Cys Val Asp Val Gly Phe Thr Met Ser Asn Ser Ile
                100               105               110

Pro Gly Ile Glu Ser Pro Phe Glu Gln Ala Lys Lys Val Ile Thr Met
                115               120               125

Phe Val Gln Arg Gln Val Phe Ala Glu Asn Lys Asp Glu Ile Ala Leu
                130               135               140

Val Leu Phe Gly Thr Asp Gly Thr Asp Asn Pro Leu Ser Gly Gly Asp
145             150               155               160

Gln Tyr Gln Asn Ile Thr Val His Arg His Leu Met Leu Pro Asp Phe
                165               170               175

Asp Leu Leu Glu Asp Ile Glu Ser Lys Ile Gln Pro Gly Ser Gln Gln
                180               185               190

Ala Asp Phe Leu Asp Ala Leu Ile Val Ser Met Asp Val Ile Gln His
                195               200               205

Glu Thr Ile Gly Lys Lys Phe Glu Lys Arg His Ile Glu Ile Phe Thr
210             215               220

Asp Leu Ser Ser Arg Phe Ser Lys Ser Gln Leu Asp Ile Ile His
225             230               235               240

Ser Leu Glu Lys Cys Asp Ile Ser Leu Gln Phe Phe Leu Pro Phe Ser
                245               250               255

Leu Gly Lys Glu Asp Gly Ser Gly Asp Arg Gly Asp Gly Pro Phe Arg
                260               265               270

Leu Gly Gly His Gly Pro Ser Phe Pro Leu Lys Gly Ile Thr Glu Gln
                275               280               285

Gln Lys Glu Gly Leu Glu Ile Val Lys Met Val Met Ile Ser Leu Glu
290             295               300

Gly Glu Asp Gly Leu Asp Glu Ile Tyr Ser Phe Ser Glu Ser Leu Arg
305             310               315               320

Lys Leu Cys Val Phe Lys Lys Ile Glu Arg His Ser Ile His Trp Pro
                325               330               335

Cys Arg Leu Thr Ile Gly Ser Asn Leu Ser Ile Arg Ile Ala Ala Tyr
                340               345               350

Lys Ser Ile Leu Gln Glu Arg Val Lys Lys Thr Trp Thr Val Val Asp
                355               360               365

Ala Lys Thr Leu Lys Lys Glu Asp Ile Gln Lys Glu Thr Val Tyr Cys
                370               375               380

Leu Asn Asp Asp Asp Glu Thr Glu Val Leu Lys Glu Asp Ile Ile Gln
385             390               395               400

Gly Phe Arg Tyr Gly Ser Asp Ile Val Pro Phe Ser Lys Val Asp Glu
                405               410               415

Glu Gln Met Lys Tyr Lys Ser Glu Gly Lys Cys Phe Ser Val Leu Gly
                420               425               430
```

```
Phe Cys Lys Ser Ser Gln Val Gln Arg Arg Phe Phe Met Gly Asn Gln
            435                 440                 445

Val Leu Lys Val Phe Ala Ala Arg Asp Asp Glu Ala Ala Ala Val Ala
450                 455                 460

Leu Ser Ser Leu Ile His Ala Leu Asp Asp Leu Asp Met Val Ala Ile
465                 470                 475                 480

Val Arg Tyr Ala Tyr Asp Lys Arg Ala Asn Pro Gln Val Gly Val Ala
                485                 490                 495

Phe Pro His Ile Lys His Asn Tyr Glu Cys Leu Val Tyr Val Gln Leu
            500                 505                 510

Pro Phe Met Glu Asp Leu Arg Gln Tyr Met Phe Ser Ser Leu Lys Asn
            515                 520                 525

Ser Lys Lys Tyr Ala Pro Thr Glu Ala Gln Leu Asn Ala Val Asp Ala
530                 535                 540

Leu Ile Asp Ser Met Ser Leu Ala Lys Lys Asp Glu Lys Thr Asp Thr
545                 550                 555                 560

Leu Glu Asp Leu Phe Pro Thr Thr Lys Ile Pro Asn Pro Arg Phe Gln
                565                 570                 575

Arg Leu Phe Gln Cys Leu Leu His Arg Ala Leu His Pro Arg Glu Pro
            580                 585                 590

Leu Pro Pro Ile Gln Gln His Ile Trp Asn Met Leu Asn Pro Pro Ala
            595                 600                 605

Glu Val Thr Thr Lys Ser Gln Ile Pro Leu Ser Lys Ile Lys Thr Leu
            610                 615                 620

Phe Pro Leu Ile Glu Ala Lys Lys Asp Gln Val Thr Ala Gln Glu
625                 630                 635                 640

Ile Phe Gln Asp Asn His Glu Asp Gly Leu Thr Ala Lys Lys Leu Lys
                645                 650                 655

Thr Glu Gln Gly Gly Ala His Phe Ser Val Ser Leu Ala Glu Gly
            660                 665                 670

Ser Val Thr Ser Val Gly Ser Val Asn Pro Ala Glu Asn Phe Arg Val
            675                 680                 685

Leu Val Lys Gln Lys Lys Ala Ser Phe Glu Glu Ala Ser Asn Gln Leu
690                 695                 700

Ile Asn His Ile Glu Gln Phe Leu Asp Thr Asn Glu Thr Pro Tyr Phe
705                 710                 715                 720

Met Lys Ser Ile Gly Cys Ile Arg Ala Phe Arg Glu Glu Ala Ile Lys
                725                 730                 735

Phe Ser Glu Glu Gln Arg Phe Asn Asn Leu Leu Lys Ala Leu Gln Glu
            740                 745                 750

Lys Val Glu Ile Lys Gln Leu Asn His Phe Trp Glu Ile Val Val Gln
            755                 760                 765

Asp Gly Ile Thr Leu Ile Thr Lys Glu Glu Ala Ser Gly Ser Ser Val
            770                 775                 780

Thr Ala Glu Glu Ala Lys Lys Phe Leu Ala Pro Lys Asp Lys Pro Ser
785                 790                 795                 800

Gly Asp Thr Ala Ala Val Phe Glu Glu Gly Gly Asp Val Asp Asp Leu
                805                 810                 815

Leu Asp Met Ile
            820

<210> SEQ ID NO 3
<211> LENGTH: 2473
```

```
<212> TYPE: DNA
<213> ORGANISM: Mesocricetus Auratus

<400> SEQUENCE: 3
cgtccggaaa aagtaaccaa accgcccgtg gaccagcaac atggcgtggt ccgctaataa      60
ggcagctgtt gtgctatgta tggatgtggg cattgccatg ggtaactctt ttcctggcga     120
agaatccccg tttgaacaag cgaagaaagt gatgactatg tttgtccaac gacaggtgtt     180
ttctgagagc aaggatgaga ttgctttagt cctctttgga acagacagca ctgagaatgc     240
ccttgctagt gaggaccagt atcagaacat acagtgcgc agacacctga tgctaccaga     300
ttttgatttg ctggaagaca tcgaaagcaa aatccaacta ggctctcgac aagccgactt     360
cctggacgcc ctgatcgtgt gcatggattt gattcagcgt gaaactatag gaagaagtt      420 tgggaagaag catattgaag tgttcactga cctcagcagc ccattcagcc aagatcaact     480
ggatgttatc atttgtaact tgaagaagtc tggcatctcc ctgcagttct tcctgccttt     540
tccaatcagc aagaacaacg agactgggca gcggagat ggtgacttgg gcttggacca     600
ccgtggaccc tcctttcctc aaaaggagt tactgagcag caaaaggaag catccgcat     660 ggtggagagg gtgatggtgt ctttagaagg tgaagatggg ctggatgaga tctactcctt     720
cagtgagagt ctacggcagc tgtgtgtctt taagaagatt gagaggcgct ctatgccctg     780
gccctgccag ctgaccatcg gccccgatct gtctataaag attgtagcct ataaatcgat     840
cgtacaggag aagcttaaaa agacctgggt agttgtggat gcaagaaccc tgaagaagga     900
agatatacag aaagaaactg tctattgctt aaatgacgat gacgaaactg aagtttccaa     960
agaggacact attcaagggt tccgctacgg aagtgatata attccctttt ctaaagtgga    1020
tgaggaacaa atgaaatata atcggaggg gaagtgcttc tctgttttgg gattctgtag    1080
atcttctcag gtccacagga gattcttat gggatatcaa gttctaaagg tctttgcagc    1140
aaaagatgat gaggcggcgg ctgttgctct ttcttccctt attcatgctt tggatgaatt    1200
aaacatggtc gccattgttc gatacactta tgacaaaga gctaatcctc aagttggtgt    1260 agccttttcct tatattaagg attcctatga gtgtttagtt tatgtgcagc tgcctttcat    1320
ggaagacttg cggcaataca tgtttttcatc actgaaaaac aataagaaat gcactcccac    1380
agaggcacag ttgagtgcta ttgatgatct gattgagtct atgagcttgg taagaaaag    1440 cgaggaagaa gataccattg aagacttgtt tccaacctcc aaaattccaa atccccgaatt    1500 tcagagattt ttccagtgtc tgctgcacag agtcttacat ccccaggagc gtctaccccc    1560
aattcagcag cacattttga atatgctgga tcccccact gaggtgaaag ccaaatgtga    1620
gattcctctc tcgaaagtga ggacccttt ccctctgaca gaagccgtca agaaaaagga    1680
tcaagtgact gctcaggaca ttttccaaga caatgatgaa gaggggcctg ctgccaaaaa    1740
gtgtaagatg gagaaagaag agagtcacat cagtatctct agcctggctg aagggaatgt    1800
caccaaggtt ggaagtgtga atcctgttga aaacttccgt gttctagtga ggcagaagat    1860
tgccagcttt gaggaggcga gtctccagct aataagtcac attgagcagt ttttggatac    1920
caacgaaacg ctgtatttta tgaagagtat ggagtgcatc aaagcttccc gggaggaggc    1980
catccagttt tcagagagc agcgcttcaa cagcttcctg gaagccttcc gagagaaagt    2040
ggaaattaac gaattaaatc atttctggga aattgttgtt caggatggag ttactttgat    2100
caccaaggat gaaggccctg gaagctctgt cacaactgag gaagccacaa agtttctggc    2160
tcccaaagac aaagcaaag aagattcagc aggacttgaa gaaggtggcg atgtggatga    2220
```

-continued

```
tttactggac atgatataga ctgtggatgt gttgggaatc caagcatgcc atctcngttg    2280
ctgagagctc agaaagagca tcctggaagc cattcagggg gacctgaagc cctggtgatc    2340
attccagcag acagctcagg agcgaatcac tccaagtctc tacagaatga ccacatccac    2400
atatattaca agggtaact  tagaccctat ccaaatttat aaagactcac tattttttga    2460
ttgaaaaaaa aaa                                                       2473
```

<210> SEQ ID NO 4
<211> LENGTH: 7
<212> TYPE: PRT
<213> ORGANISM: Homo Sapiens
<220> FEATURE:
<221> NAME/KEY: VARIANT
<222> LOCATION: (3)...(3)
<223> OTHER INFORMATION: Gly
<220> FEATURE:
<221> NAME/KEY: VARIANT
<222> LOCATION: (3)...(3)
<223> OTHER INFORMATION: Arg
<220> FEATURE:
<221> NAME/KEY: VARIANT
<222> LOCATION: (3)...(3)
<223> OTHER INFORMATION: Glu
<220> FEATURE:
<221> NAME/KEY: VARIANT
<222> LOCATION: (7)...(7)
<223> OTHER INFORMATION: Met
<220> FEATURE:
<221> NAME/KEY: VARIANT
<222> LOCATION: (7)...(7)
<223> OTHER INFORMATION: Glu
<220> FEATURE:
<221> NAME/KEY: VARIANT
<222> LOCATION: (7)...(7)
<223> OTHER INFORMATION: Lys

<400> SEQUENCE: 4

Leu Gly Xaa Asn Leu Arg Xaa
 1               5

<210> SEQ ID NO 5
<211> LENGTH: 1094
<212> TYPE: DNA
<213> ORGANISM: Salmonella Typhimurium

<400> SEQUENCE: 5

```
cgatttattg gttcttgaaa accaaggttt ttgataaagc aatcctccat gagaaaagcg     60
actaaaattc ttccttatct gatgtaaagg agaaaatcat ggctactatt gggtatattc    120
gggtgtcaac aattgaccaa aatatcgatt tacagcgtaa tgcgcttact agtgcaaatt    180
gtgaccgcat ttttgaagac cgtatcagtg gcaagattgc aaaccgcccc ggcctgaaac    240
gggcgttaaa gtatgtaaat aaaggcgata ctcttgtcgt ctggaaatta gacagactgg    300 ccgtagcgt  gaaaatctg  gtggcgttaa tatcagaatt acatgaacgt ggagctcact    360
tccattcttt aaccgatagt attgatacca gtagcgcgat ggggcgattc ttttttcatg    420
taatgtcagc actggccgag atggagcgag aattaatcgt cgagcgaacc cttgccggac    480
tggctgccgc cagagcgcaa ggacgactgg gagggcgccc tcgggcgatc aacaaacatg    540
aacaggaaca gattagtcgg ctattagaga aaggccatcc tcggcagcaa ttagctatta    600 ttttggtat  tggcgtatcc accttataca gatactttcc ggcaagcagt ataaaaaaac    660
gaatgaatta aaataaaaat cacaacagga tggatataac attttttgtaa tacaggcgta    720 tggcataaat aaaccgaaag ggtatacaaa aagacagca  tctaattaaa aagagaaaaa    780
```

```
attcaacgta ttaacatata tagtgtaacg cgctcacgat aaggcctatg ttacatccag    840
ctatagacga catcgctcaa aacactacca gacacagtat tcacctggaa aggctttta     900 atcaaaatgt tagatgtaag caattacgga cagaaaaaat agtaaagttt atgcctcaag    960
tgtcgataac ctggatgaca caggtaagcc tggcataaca ttggttatca aaaccttcc   1020 aaaaggaaaa ttttatggca caagtaatca acactaacag tctgtcgctg ctgacccaga  1080
ataacctgaa caaa                                                    1094
```

<210> SEQ ID NO 6
<211> LENGTH: 14636
<212> TYPE: DNA
<213> ORGANISM: Homo Sapiens

<400> SEQUENCE: 6

```
gagctccaac attcaagttt gggaagaact gaacaatttc atactgctgg gccatggtac     60
tcagttaaaa aggtggcaga taaagcaggg atataccccca cagtctcaaa gacaagcagt   120
gacaactgga ggtagaactg gacctgtgac caagtccaat gactcactaa agcacagcat   180
tgaaagcaag ccagacatgc tcaagtgctg gtgcaaacct acactcttac ctgtaacatt   240
cactctgtcc ccaggctgga ccttgtcaac gagatcattg tgagcaaaca ggataactgt   300
gtgtggtgtc tgccctgcag gcatgtcttc cggagactcc tgaagcttga tctgaaggtc   360
agcaaacaga gaacatgtgg gccacaaaga gagggcaggg ggacaaaatc tgcatgtctt   420
tgtactgctt ttgccatata aggctgcagt gcatatcccc acataaatga ttgtccatgt   480
ttctcattat ttccttagaa attacttctt ctaaagaagt tgctgcaaca gacagcaaca   540
aaacagggga aggaatgtag ggagctgcgg tgggggaagc tgagatgctt ttcataaagc   600
agggtcgagg aaggccttc caaaccaggt accctctgag aggcctaagg atgctgggct    660
tttctctaag ccactttggg ggcctgcatg attctgagaa taggaggcca tgtgctcctg   720
cggagcaggt gcctgccttt ctgtctccag ctctccatcc catgcaacat taaagaaacc   780
atgcacacgc agtcacagaa aaactcaaat cctgtcctcc cacatcttta cagtcacaat   840
cacggtaaat aagcaatttt ctaccttccc ctcacttttt tctgtcattt taataacttc   900
atcttaaaat ttcatgaata tagagaaaaa agaccaaact tcttagacag taaaatttgt   960 gaaaaattt cagaaaaatt cctcaatcct ttaccaatgg aaaaagcaga atgacattta  1020
accaagtatt ctcatctcaa acgtttgaag cattttaggc catgaaaata cagtgtctct  1080
aacaacagac agtgccactg caacagcac agggacagtg ccctgaagca ggggcttttgc  1140 gtgctctgca tatttagccc ataggccact aacgaaaccc acaagaccag agagggatgg  1200
atgccattcg ggaagtgagg ctcagggtcc gagggacaag ttatagttgg cctttgagg   1260 atacagacag gcaaagcata gcctgggggg ccagggtggc tgcgcaccat ctgcttgtca   1320
gagaagaggg agcggttgtg gatgagtgcc atgctgtggg tggtgtggca gcgcccgcac   1380
acactgggct ctgcaatgcg gccgcggtcc atctccaccc gggtcgtgtg ggcacacact   1440
tggcactgga agaaggcctc ctgcatctcg ggaatcagct gggatgtcct gatcaccatg   1500
ccgctgatgt tgatgagctg gtcaatgtct gtgaggggag aagagaggtc agcacacctg   1560
acctgaggtg tggaggtcca ggaatagctg ggatcacaga caggagctag gtgcccaaga   1620
ctctgcctag ggcgaccttt ctgtgtccag tcatctgcag gctatgtctt caggagactc   1680
tcaagcccag cgaacctctg gcccttcttc ctcagggccc ctgtccagca ggcatccctc   1740
```

```
gttcccttct tgtctgccta ccctgctccc tgcctcctgc ctcactcacc tggcctcctg    1800
tatgacaccc tgctgtgtca ggaaaaaagc cagacagcct ggactgagtc ctgaccctag    1860
cctttctgtg tacattttgt gtcccctata gaatggggtg gtatcagcac ctatcccaga    1920
gccaaggact gaacgtgcca atgtacttca agcctagtaa gagcacctgg tagagaaaaa    1980
gtcctctata ctttaaagtc attattatcc acacaggaga accccttaga tgctctgatc    2040
tttcactctt gctcgtttcc tctattattt gaacctttcc tgacagacaa cttttTccct    2100
ttgaaggtcc cactgcccgc aactaatttc ccctgctggt tcagacaag ctaccctgtt     2160 ctggcctgta tttagccact gctagccgtg aagatcaccc tatcctgcca ctgattcatg    2220
agacctctac aattttgttg ttgttgagat ggggtcttaa cctgttgccc agactggagt    2280
acagtggtgc aatcactgct cactgaagcc tcaacctgcc aggctcaagt aagcccgtca    2340
cctcagcctc ccagagtgct aggattacat gtgtgagcca ctgtgccttg ctaatttctt    2400
cttaaaaaga gatggagtct cttatgtcac tcaagctggt ctcaaactcc tggcctcaag    2460
tgatcctcaa atctttaaaa tctaattttt tttttttttt gagacagggt ctcattctgt    2520
cacccaggct ggagtgcaat ggcacagcct ctgctcagtg caacctccgc ctcccgggtt    2580
caagcgtttc tcctgcctca gcctcccgag agtagccggg actacaggcg tgtgccacca    2640
tgccctggta atttttctat ttttagtaaa ggagttttgc catgttggcc aggctggtct    2700
caaactcctg acctcaggtg atccgcctgc ctcggcctcc tgaagtgctg ggattatagg    2760
cgtgagccac tgtgcccggc caatagtcac atctcttata tcagaaactt caattaaatt    2820
taaaaagtat aggggttca taagtatata ggataactga atctatatta ttgtcaattt     2880
ataatccgtc accttgacta ccaccgccaa ttacttcttt cataatttct caatgaaaac    2940
aaggctattt tcatgtaagg cattttcctt caacaaaagt aatcctatga aaatacatt     3000 accttctgga ttcaggtttc tcatattctt agtcttcaat gcgttgaatg gtcttacttg    3060
aatctgatgt tctaagattg agtcagggta acggtcaaag aagattctca t gacagccat   3120 gtcaaaagtt ggaataactt cctgtaaaaa caaatatgaa gatgtatttg tattcatatc    3180
tcagtgttaa atataataaa ggcatgtcag attagcaaag tataaaaaga caacatgtca    3240
tgtccccaaa gtattaccct acagaatcat gcacgtgctg ttttcaaatt taggtatgct    3300
gaactatcta tttctgcata ttttcaattg ggttaaattt cataatttat acgaaagtgc    3360
cttcttgatg tatactggca tattctttgc tttctattag aagggaaaaa gattttgacc    3420 tcacactta ttttccttct ataatgaagt gataccaaag taagtttttt atttatttat     3480
ttttaatttt tgaggcagag tttcactctt gttgcccagg ctggagtgca acagcatgat    3540
cttggctcac tgcaacctct gcctctggga ttcaagtaat tctcctgcct cagcctcccg    3600
agtagctggg attacaggca tttgccacca cgcctgacta tttttgtatt tttaatagag    3660
acggggtttc tccacgttgg tcaggctggt cttgaactcc caacctcagg tgatctgcct    3720
gcctcggcct cccaaagtgc tgggatcaca ggcatgagcc accgtgcctg gcgataccaa    3780
agtaagttaa atcatattta ttcaaatttc ttaacatatg gttcccattt tacagatgag    3840
gaaacagctt ttggttggct aaggaacttg accaaggtta tgcagccagt aatcagcaaa    3900
accaagattc aaaaaccaag tctgcttgcc tccaaagact acacccagag tcaacagagc    3960
tgatacttca ttaatagaaa ctgacctgag gcttagaagt aaaagtctac agtacaatat    4020
attctttcaa agcagcagga agtatgtaat tcatttaaag tatttccatt taagataact    4080
tacttcatga aacccaagaa gctatcagtt ttaagattca tcattttttct acatgaaaaa    4140
```

-continued

```
cactgccaag taaaccataa cctgtcattg atagtaatac aagtcccact ttcaggaaca      4200
ttaaaatgtg aaaaaaaaat gttcatctta aaggagatga tacatagttt tttttttgttt    4260 gtttgagatg gaatctcact gttgcccagg ctggagagca gtggtgccat ctcggctcac    4320
tgcacctctg cctccggggt tcaagtgatt ctatcgcttc agactcccga gtagctggga    4380
ctacaggcat gcaccaccat gtctggctaa ttttttgtatt ttttagtaca gatgggtttt    4440
cactttgttg cccaggctgg tctcaaactt ccgacctcaa gtgatccatt tgcctcggcg    4500
tcctaaagtg ctgggattat aggtgtgagc caccacaccg ggccaaagga gatgatactc    4560
agtttcttaa agtgtttgcg catactatct tcattactga agaatttctg ttatctggaa    4620
acattctttc tagactgtta ctaaaattca tcaaggtcaa agctaaattc ttacctgtgg    4680
gtaagagatg agttgtctgt acaaattttt gtcaaatgat ttgatgtgtt cacagttcac    4740
atttaaaaat ggctcaccaa taacattaat ctagaaaata aaaatgaaca agttatattt    4800
tgctaattta actattttaa aacacgtaac ttgaatttaa agagtatttg attacctccc    4860
caagtcgttg catgtataga ggttcagtaa tatctatgcc aacatttttct tcttctttag    4920 ccagagggtc aataaaacgc tgaagaaatc tctttaagtg gagagaaaac tgtattaggc    4980
atatagcatt tgggaacagg caactactaa aaacacacaa agttatgagt atgtcactat    5040
caggagacag aaataaataa tattttttctt cctttttcttt ttctaaaatt taatttggag    5100
atggagtctc actatattgg tcaggctgct atcaaactcc tggcctcaag tgatcctccc    5160
accttggcct cccaaagtac tgggattata ggtgtgagcc accacaggtg gcccttctag    5220
tcattatggc tacttagata tagattataa acacggtctc ccaacatttt cagagcccaa    5280
agtaagaatt ttaatacatg tagctcacct gaaagttttc tttgcatgct gccacattta    5340
catctgttcc ccagatcaca agtttttggc ctagagactg ctcacttgcc actatatctt    5400
ctgctgctgc ctacacagaa aaacatgaca gaatcatgaa aacagagtta cccacatgat    5460
acccgccata agatggtttc aggagactgc atactcaccc cgtcagactg cagatccact    5520
tgcaggccct tctgtgcaga gcccaggtca ggcctctgtc tcacaggtgt gcccctaaca    5580
ccacttcttg gggttccctc tacccgagag ctgggagtgc cgtatgtcag tggtgaacta    5640
acatcaaagt caagagggat agctataaaa acaaaattag gaaattctgg tggcatatca    5700
aacctgaaat tacagcatgt tgtctgttga tctataccat ctaatcgcaa cagcaaactg    5760
aatatttatt gcaacctgcg gtggctgaga ttctgagcac tcttaaatgt tctattaaaa    5820
aaaagcacca gagaagctgc ttcctctgct cactaagccc taaaactact attttctgca    5880
ctccgttcag ctcctctggt taagaacatg ctcagtcacg tgcagagggg atgctttagg    5940
cgttatgcca actgttataa agccagtaaa cctgagcaga taaagcatca gctgtgtatc    6000
aagcacagca aaaccaagat cttcagacac gcacctgaag aatgcatttg gggagggctg    6060 gaaacagca cgtcctgcgc agcagggctc tgcaggtcca ctccaggcga ggttggcatc    6120
ggctgcaact ccccgtgga ggtggaatcc tcgcctctac gtctctgaga gggagatgac    6180
ctggcatcct cactccgagc ttgtgtcaca caaaacagaa aagacagcca ttaactttca    6240
gggccggcct tctggatttt gtcttttcct tggggcatta tgactcacca ctgaaccaaa    6300
ccaaacagag gcaaatggca atcgaattaa gcagcaccca ggccacagcc tgctgtgggt    6360
gtctgtgcgc accaagcggc agcgcccagc ccgaggctga gcgccgggt cccgcgcacc    6420 cacccagcgc tgccagctgc ggcgagaggg cagacggggc ggcgccgggg gctgtagtgg    6480
```

-continued

```
gcccggctcg ggggactcac gcgtctgggc gggggtggcc cttccacgcc ggctgccgcg    6540
gcggctcggg gtcgacgccg gggacgacat agtgctcgga gtacctgcgc gacaaggaca    6600
agctcgggcc gggcccgcct cccggcttcc ctgccctgct ccgcagcgcg gacgttcccg    6660
tcggctccgc gccacgccct ccccgccggc gcgcggttac cgtggaaagg cggccgcttg    6720
ccgacgacgc tcgcggactc cgagtccacc tgcgagtag cgctcccaaa ccgcgagacc    6780
cagagttccc gccggcggca aggtcgtctc cgcccctggc ggggcctcac caatcacagc    6840
ggcgctcgta cgtggctccg cctccgggag gcgccactgc gcatcggcag gggggggacag   6900 tgccgcttct ttcagcgccc gtgcgtaaac cagaagtagg cctcgctcgg cccccttgg    6960 tccagatggt ctgaccccct gcgcggcagc gttttcgcgg gaaaactggg tcctacagca    7020
ccagctctcg gggtgtgttc ctctagcgtt ggctaggag cgtgtgcttc tttatccctt    7080
aggcgttttt ggttaataag gacattacag atgcatttct cacttaaaga ttttttttat    7140 taaaaaaat taaggacggg aagtggtggg gatggtctca ttatgttgcc cagactggtc    7200
tcgaactcct gcgatccccc cgcctcagct cctaaagtg ttgggactgc aggcgggcat    7260
caccgccccc gaccgcgttt gtcgtttttt atcgaggaac aaacttggaa ctcttgacct    7320
aggcccctcg cttgttttat ctgcctctgg tatttattta gccaagtcca acaccaagta    7380
gccacccaaa ctacctccgc aggtcagacg ttttccctta ggtttccatg ttgattcggg    7440
ccaaagaggc gcgcttactg gccaggcctt cccgcagggg tccccgggaa agttcctgcc    7500
gccgcgcccc gcagccccgc ctccgcgcgt agggggcattt ccggtccggg ccgagcggg    7560 cgcacgcgcg ggagcgggac tcggcggcat ggcgggctcc ggagccggtg tgcgttgctc    7620
cctgctgcgg ctgcaggaga ccttgtccgc tgcgaccgc tgcggtgctg ccctggccgg    7680
tcatcaactg atccgcggcc tggggcagga atgcgtcctg agcagcagcc ccgcggtgct    7740
gggtgggtac cggcccgagc tgggccgcgg gtgggtcctg gcttcccgag tcgttctgga    7800
gccgggcagc ccggcgcttc tctgtgttta gatgacggta ttttgaagta cagcaattag    7860
attcttgggg gaatttctgt gtatgtgtat aaagggattt gtcatactgc ttttaccccc    7920
ctagtattag aggaaagata ttttaaagcc aaagttggtg aaaacgaccc ctaatatggc    7980
aatcattgct atgcagagtg gggggcaggg caagagaaat aatttttttt tttttttgaga   8040 cggagtctcg ctctgtcgcc caggctggag tgaagtggcg cgatctcggc tcactgcaac    8100
ctccgcctcc cgggttcaag ctattctcct gcctcagccc cccgagtagc tgggattaca    8160
ggcgcgcgcc accacgcccg gctaattttt ttgtattttt agtagagatg gggtttcacc    8220
atgttggtca ggctggtctc gaactcctga cctcgtgatc cccccgcctc ggcctcccaa    8280
agtgctggga ttacagacgt gagccaccgg gcccggccaa gagaaagtat tttctttcac    8340
ctgaatctcg cctaatccca ccagtacctt tccaaaccc ctctatttgc cgttcctact    8400
ttgagaaaaa ttgaagaaat gtaattgaag tcatgttctt ttaactcttt agcaatgcct    8460
gggtgggaac ttttttcccct ttgtagtaaa agtgcctctt tttagcattt taaatattca    8520
aatacttaat tatgtggatc tcctgtattc cttctttaaa acacgagtat gcagaccttg    8580
atgttgtgcc ctattaaaag gtgagatttt cttccggagg gtctagtagt gaatatggtg    8640
taggaataac ttaaacagtt taaactagat gctatatgtg gcacggtgcg gtggctcatg    8700
cctgtaatcc cagcactttg ggaggctgtg gcagctggat cacctgaggt caggagatgg    8760
agaccaacct gaccagtatg gtgaaaccctt gtctctacta aaaatacaaa aattaactgg    8820
gcatggtggc gagcgcctgt agtcccagct attcgggagg ctgagacagg agaatgtctt    8880
```

```
gaacccagga gaaggagatt gcagtgagcc gagattgtgc cactgcactc cagcctgggc   8940
aacagagcac gactccgtcc caaaaaaaaa aaaaaaagat gctatataca tgtatcctat   9000
atgtactcta tctgttgtca agaatatatt aacaatgggg aaatatcaaa caaaaaacta   9060
acattgcgtg attactttct cttctcaggg tttcaaattt agaattcatt tttgttcgtt   9120
tagtaacttg tttctaaagc acttccaagt ttaccttcca tttatgccat atctcctttc   9180
acttgagaga ttccaggga agtgtattag ttccttattg ctgctgtaac aattaccaca   9240
agcttagtgg tttaaaacag cacaggtctg ttactcttac agttcccact gtaaggggga   9300
ttctgtgagt cagaatccca cacaggtctc accaagctag aaccaaagta ccagacaggg   9360
ctgctttctt tctgaaggct cttggggagg atccattgcc ttattcattc aggttatata   9420
ggattgaggt ccctgacatt ccatacttct tgaagctgtc cccttccctt ggatcacagc   9480
tcccttccct tggtcttcaa ggccagcaac agcatgtcaa gtcccctaa ctagaggttt    9540 ggaatctccc gctttcccaa cttcctgtct ctctgaccca ctcttcttca tctccttact   9600
ttaagggcct gtgtgattac attgggctct ctggataatc cagtatgatc ttcccatttt   9660
aaggtcagct gattagctac cttaattcca tctgcaagct caatttcctt tgctatata    9720 catttaacat attcacaaga tgtgaccca gggattggga tgcaggcatc tttggggcca    9780
ttattttgcg tactgcatcc ctgtggaaca ttgtctagaa ttttctgctt tgttttaata   9840
cagcaacctt gggttagtgt tttatattta taaggctgcc ttgaaaaccg ttgcaacctt   9900
ggccaggcgc ggtggctcac gcctgtaatc ccagcacttt gggaggccga ggcgggctga   9960
tcgtgaggtc aggagatcga gaccatcctg gctaacacgg tgaaaccccg tctctactaa  10020
aaatacaaaa aaaaaattag ccgggcatgg tggtgggcac ctttagtccc agctacttgg  10080
gaggctgaga taggagaatg gcgtgaaccc gggaggcgga ggttgcagtg agccgagatc  10140
gcgccgctgc actccagcct gggcgacaga gcgagactcc atctcaaaaa aataataag   10200 aaaatcattg caacccctt aggagtggtt tacatgatgc tcttggcact ctcttaactt    10260
gtttacttat tttttttgaac agcattacag acatctttag ttttttccag agatttcggt  10320
ttgcttgtat ttgtccggaa gtcactcaac agtattgaag taagttgaca attttggttt   10380
tgcttttctt gtatattcct ggagtgactc ctcttaccca tatttacaat atgtatctct   10440
ttcattacag tttcgtgaat gtagagaaga aatcctaaag ttttttatgta ttttcttaga  10500 aaaaatgggc cagaagatcg caccttactc tgttgaaatt aaggtaagaa ttaaaaaaca  10560
taccttatta cattatatat caacatctgt tttaacttat ggtgtgagga acttggattt   10620
ttattttaaa gataaaacat tttcctttct cattgggaa tttgcttatt tctgcttcat    10680
tgtgttacaa atgaagtggg ctcttcatta ggtttttttt tttttttttt tttttgaga   10740 tggagttttg ctcttgttgc ccattagtta tttagattta gtaagctaag gcctttgtga  10800
gagaaactac tttgataatt ttttttaata actatcttaa tacttttttt tcctgaggag   10860
gtggcagtgg caccctgggc tccctggggc cctgatggcc tcttgataac ttcactgcag   10920
cctgggcgac aagagcaaaa ctccatctca aaaaataata atttttattt tgtatttttt   10980 tattttatt gtttatttgt tttattttg tgagacaggt ttttgctctg tcatccaggc     11040
tggagtgcag tggtgcaatc atggctcact gcagcctcca tctcgtgggc tcaggtgatt  11100
ctcacacctc agcctcccaa gttgctggga ccacaggatg tgccactatg tccagctaat  11160
ttttgtattt ttttttttttt ttgtagagac agggtttcgc cttgttgcct aggctggtct  11220
```

-continued

```
tgaactcctg ggcttaagtg atcttcccgt ctccgcctcc caaattgctt acaggcacga    11280
accacactgt aatcctcaaa gggattacag gcatgaacca cactgtaatc ctcaaaggga    11340
ttataggcgt gaaccacaga gtcccgtgaa tactttcagg ctggagtgca gtggcacagt    11400
cttggctcac tgcaacctcc gtctcccggg ttcaagcgat tctcctccct cagcctcctg    11460
agtagctggg attacaggcg tgcaccaccg tacctggcta attttttatat ttttagtaga    11520 gatagggttt caccatgctg gccaggctgg tctcgaactc ctgacctcag gtgatcgcct    11580
acctccgcct cccaaagtgt tgggattata ggcatgagcc actatgcccg gcctaatgtt    11640
atattttcca cagctaaata ctgaattttg gtattgctcc tcttggagaa gtagtttcag    11700
gtattgctga gtcttagttt ttatatctta ttgatgattt tggttatttt ttttttaaaa    11760
cctagaacac ttgtaccagt gtttatacaa agatagagc tgctaaatgt aaaattccag    11820
ccctggacct tcttattaag gtaattatgt ttctaagtac acgtatttta cattaaacat    11880 gtaacttta aaagaaaatc agagttttga gttgtgtttt gggtgatgtg tttggggaag    11940
gataggatct aatcacattg atgtgtgggt aagatgcaca ttctccaacc atcacctgac    12000
aataccctgg ctttttgttt tcagactctt ctgggtagta aaagaagaat tctgagttgt    12060
gaggagaatg aaggaggaaa atgactaagg aatttattgc tctttcattt atcaccctta    12120
ctggctttgg caaaacctaa tgctattagg aattgctgaa agatcacctt atatctctga    12180 ggttttcct aaaaccttag caatgggaaa gagttcatat gttttctttt ttttttttt    12240 ttttttttt ttgagacgga gtctcgctct gtcgcccagg ctggagtgca gtggcgggat    12300
ctcggctcac tgcaagctcc gcctcccggg ttcacgccat tctcctgcct cagcctccca    12360
agtagctggg actacaggcg cccgccacta cgcccggcta attttttgta tttttagtag    12420
agacgaggtt tcaccgtttt agccgggatg gtctcgatct cctgacctcg tgatccgccc    12480
gcctcggcct cccaaagtgc tgggattaca ggtgtgagcc accgcgcccg gcccatatgt    12540
tttcttttct ttctttttttt gagacagagt cttgttctgt cattcaggct ggagtgcagt    12600
ggcgcaatct cggctcactg caacttctgt ctcccaggtt caagcgattc tcctgcctca    12660
gcctcctgag tagctgggat tacaggcatg tgccaccatg cctggctaat ttttgtattt    12720
ttagtagaga cggggttta ctgtgttggt cacactggtc tcgaactcct gacctcgtaa    12780
tccgcctgct tgggcctccc aaagtgctat gattacaggc gtgagccact gtctggcggg    12840
aatcagttga tacgttgcag ttaagtggtt gttggggtca ctgtgacctg tttctgtttt    12900
ttttgtattt gtattttaga attccttttgt ttctggttgc tccttggttt tgtaggcttc    12960
tgggagaaag gttctagtca tgttgttggt ttcttgggaa ggtaacacac ctagagcatt    13020
cttcccctga tgttcttcca ccatacccat ctcaacctct aattcccaga taagctgggt    13080
ggatgtgaat cctgtgagac caagtgtaaa tccttgagac acacctaatt ctgaaccttt    13140
gctgtggaca gatgcactga gatagaggaa tcccgttatt tccctcttta gagagaatgc    13200
taatttgtat tgtgtttttt ttcttgattc ccgcactaca ttgatgtact aatttgtatt    13260
cttttagtta cttcagactt ttagaagttc tagactcatg gatgaattta aaattggaga    13320
attatttagt aaattctatg gagaacttgc attgaaaaaa aaaataccag atacaggtga    13380
gatgcattta catgttattt tcaaatagtt tagcaaatta atattaacaa attattagca    13440
taagacttag gttttctcta ccaaggtctt attttacagt cgaatccttt ttgctgaaaa    13500
taaaccaaaa tggaaccaaa caaaaacaac atgtgaagac ttcccttcac aaaaatgtta    13560 attttacaa aattattcct gtaaatagaa aactcacaag atatgacaaa tatgattaat    13620
```

-continued

```
acatttgcat aaaacttagg aaagaatgca gtcctaaaag ctttatattt tatatctctt    13680
actgtaaaat caattttgaa ctttatttta ttttattttc ttcatacatt ttggttagtt    13740
taacttattt aaatgtagtt tgaggccttc acttgtctaa aatttctttt tcagttttag    13800
aaaaagtata tgagctccta ggattattgg gtgaagttca tcctagtgag atgataaata    13860
atgcagaaaa cctgttccgc gcttttctgg gtgaacttaa gacccaggta tgatgaactt    13920
tatgacattc tgcttccata gatgtggttg tgttttctc ttgtaatgac atcttcttaa    13980 atctttctt ttagatgaca tcagcagtaa gagagcccaa actacctgtt ctggcaggat    14040
gtctgaaggg gttgtcctca cttctgtgca acttcactaa gtccatggaa gaaggtattg    14100
cttggcttca cttgattttc tttattcaaa aactgtaagt ctaaccagca atgcctgatt    14160
atttctttga actcttaacc aatcctgaat ttacatacag tagtgagaaa taatctagag    14220
ggacctgtgg gccctcccga gttcccctga tgatgacatc tttcccaact acagcacaac    14280
agcaaggtgg gcattaacat tgatgttgtc cactgagctt tgtcagatct caccagttta    14340
acgtgcacac atttgtgtat gtgtatttag ttctgtgcag ttgtttaaaa ttttattat    14400 ttttttgag acagaatctt gctctgtcgc tcaggctgga gtgcagtggt actttcttgg    14460
ctcactgcaa cctctgcttc ccaggttcaa gcagttcttc acttcagcct cctgaatagc    14520
tgggactata ggcacgcacc accacacctg gcaaattact ttcttttttt ttttaaacag    14580
agtctcgctc cgtagcccag ggtggagtgc agtggctcga tctcaggtca ctgcag        14636
```

<210> SEQ ID NO 7
<211> LENGTH: 30
<212> TYPE: DNA
<213> ORGANISM: Homo Sapiens

<400> SEQUENCE: 7
ctcatggtaa agcccacgtc catacacagc                                    30

<210> SEQ ID NO 8
<211> LENGTH: 22
<212> TYPE: DNA
<213> ORGANISM: Homo Sapiens

<400> SEQUENCE: 8
gtaatacgac tcactatagg gc                                            22

<210> SEQ ID NO 9
<211> LENGTH: 30
<212> TYPE: DNA
<213> ORGANISM: Homo Sapiens

<400> SEQUENCE: 9
aacagctgcc ttattccccg accgcaccat                                    30

<210> SEQ ID NO 10
<211> LENGTH: 19
<212> TYPE: DNA
<213> ORGANISM: Homo Sapiens

<400> SEQUENCE: 10
actatagggc acgcgtggt                                                19

<210> SEQ ID NO 11
<211> LENGTH: 30
<212> TYPE: DNA

<213> ORGANISM: Homo Sapiens

<400> SEQUENCE: 11
tcttgtcagt ggtccttgtc tcccttcttg                30

<210> SEQ ID NO 12
<211> LENGTH: 30
<212> TYPE: DNA
<213> ORGANISM: Homo Sapiens

<400> SEQUENCE: 12
tacgatccag agctagggag agagagaaaa                30

<210> SEQ ID NO 13
<211> LENGTH: 20
<212> TYPE: DNA
<213> ORGANISM: Homo Sapiens

<400> SEQUENCE: 13
gctcaaacac cacacgcccc                20

<210> SEQ ID NO 14
<211> LENGTH: 20
<212> TYPE: DNA
<213> ORGANISM: Homo Sapiens

<400> SEQUENCE: 14
ttattccccg accgcaccat                20

<210> SEQ ID NO 15
<211> LENGTH: 27
<212> TYPE: DNA
<213> ORGANISM: Homo Sapiens

<400> SEQUENCE: 15
ccatcctaat acgactcact atagggc                27

<210> SEQ ID NO 16
<211> LENGTH: 23
<212> TYPE: DNA
<213> ORGANISM: Homo Sapiens

<400> SEQUENCE: 16
actcactata gggctcgagc ggc                23

<210> SEQ ID NO 17
<211> LENGTH: 29
<212> TYPE: DNA
<213> ORGANISM: Homo Sapiens

<400> SEQUENCE: 17
acggcggaat ggagagaatg tgcgcatgc                29

<210> SEQ ID NO 18
<211> LENGTH: 30
<212> TYPE: DNA
<213> ORGANISM: Homo Sapiens

<400> SEQUENCE: 18
cctttcaggc ctagcaggaa acgaagcggc                30

<210> SEQ ID NO 19
<211> LENGTH: 26

-continued

```
<212> TYPE: DNA
<213> ORGANISM: Homo Sapiens

<400> SEQUENCE: 19
cgtttcctgc taggcctgaa agggc                                        26

<210> SEQ ID NO 20
<211> LENGTH: 26
<212> TYPE: DNA
<213> ORGANISM: Homo Sapiens

<400> SEQUENCE: 20
gcccgagcat gcgcacattc tctcca                                       26

<210> SEQ ID NO 21
<211> LENGTH: 30
<212> TYPE: DNA
<213> ORGANISM: Homo Sapiens

<400> SEQUENCE: 21
gctggacctg gtggcacaca cctgtggtcc                                   30

<210> SEQ ID NO 22
<211> LENGTH: 31
<212> TYPE: DNA
<213> ORGANISM: Homo Sapiens

<400> SEQUENCE: 22
gaactcccag catcacagcc gatggcagct c                                 31

<210> SEQ ID NO 23
<211> LENGTH: 26
<212> TYPE: DNA
<213> ORGANISM: Homo Sapiens

<400> SEQUENCE: 23
gggagacaag gaccactgac aagata                                       26

<210> SEQ ID NO 24
<211> LENGTH: 25
<212> TYPE: DNA
<213> ORGANISM: Homo Sapiens

<400> SEQUENCE: 24
atacagctgc tgtgtctcca cttgg                                        25

<210> SEQ ID NO 25
<211> LENGTH: 16
<212> TYPE: PRT
<213> ORGANISM: Homo Sapiens

<400> SEQUENCE: 25

Gly Arg Asn Leu Arg Glu Leu Gly Gly Asn Leu Arg Lys Leu Gly Gly
 1               5                  10                  15

<210> SEQ ID NO 26
<211> LENGTH: 23
<212> TYPE: DNA
<213> ORGANISM: Homo Sapiens

<400> SEQUENCE: 26
agatctagag aatgtgcgca tgc                                          23
```

```
<210> SEQ ID NO 27
<211> LENGTH: 30
<212> TYPE: DNA
<213> ORGANISM: Homo Sapiens

<400> SEQUENCE: 27
agctgcctta ttagcggacc acgccatgtt                              30

<210> SEQ ID NO 28
<211> LENGTH: 30
<212> TYPE: DNA
<213> ORGANISM: Homo Sapiens

<400> SEQUENCE: 28
gctggtccac gggcggtttg gttactttt                               30

<210> SEQ ID NO 29
<211> LENGTH: 10
<212> TYPE: DNA
<213> ORGANISM: Homo Sapiens

<400> SEQUENCE: 29 rrrcwwgyyy                                                    10

<210> SEQ ID NO 30
<211> LENGTH: 60
<212> TYPE: DNA
<213> ORGANISM: Homo Sapiens

<400> SEQUENCE: 30
ctccctagac ttgtcttcta aattaaacct tgactcctcc cttccaagct ggagccactg    60

<210> SEQ ID NO 31
<211> LENGTH: 32
<212> TYPE: DNA
<213> ORGANISM: Homo Sapiens

<400> SEQUENCE: 31
atctggcacc agaccttcta caatgagctg cg                           32

<210> SEQ ID NO 32
<211> LENGTH: 32
<212> TYPE: DNA
<213> ORGANISM: Homo Sapiens

<400> SEQUENCE: 32
cgtcatactc ctgcttgctg atccacatct gc                           32

<210> SEQ ID NO 33
<211> LENGTH: 25
<212> TYPE: DNA
<213> ORGANISM: Homo Sapiens

<400> SEQUENCE: 33
ctgttgtgct gtgtatggac gtggg                                   25

<210> SEQ ID NO 34
<211> LENGTH: 25
<212> TYPE: DNA
<213> ORGANISM: Homo Sapiens

<400> SEQUENCE: 34
ccaggaagtc agcctgttga gaacc                                   25
```

```
<210> SEQ ID NO 35
<211> LENGTH: 2793
<212> TYPE: DNA
<213> ORGANISM: Homo Sapiens
<220> FEATURE:
<221> NAME/KEY: unsure
<222> LOCATION: (2711)...(2711)
<221> NAME/KEY: unsure
<222> LOCATION: (2733)...(2733)
<221> NAME/KEY: unsure
<222> LOCATION: (2735)...(2735)
<221> NAME/KEY: unsure
<222> LOCATION: (2743)...(2744)
<221> NAME/KEY: unsure
<222> LOCATION: (2749)...(2749)
<221> NAME/KEY: unsure
<222> LOCATION: (2769)...(2769)
<221> NAME/KEY: unsure
<222> LOCATION: (2771)...(2771)
<221> NAME/KEY: unsure
<222> LOCATION: (2773)...(2773)
<221> NAME/KEY: unsure
<222> LOCATION: (2775)...(2775)
<221> NAME/KEY: unsure
<222> LOCATION: (2781)...(2783)
<221> NAME/KEY: unsure
<222> LOCATION: (2787)...(2787)

<400> SEQUENCE: 35 aaacccaca aaaattagct ggacttggtg gcacacacct gtggtccag ctacctggga      60 ggctgagctc tggatcgtac aagaagggag acaaggacca ctgacaagat atgcgtttca    120
agcggctcaa acaccacacg ctcccgacta cggcggaatg gagagaatgt gcgcatgctc    180
ggcgggaatc tgcgcatgct cggagagaat gtgcgcatgc tcggccggaa tctgcgcgag    240
ctcggcggga atctgcgcaa gctcggcggg aatctgcgca tgctcagagt tccggggcac    300
ggtttccccg ccccttttcag gcctagcagg aaacgaagcg gctctttccg ctatctgccg    360
cttgtccacc ggaagcgagt tgcgacacgg caggttcccg cccggaagaa gcgaccaaag    420
cgcctgagga ccggcaacat ggtgcggtcg gggaataaag cagctgttgt gctgtgtgtg    480
gacgtgggct ttaccatgag taactccatt cctggtatag aatccccatt tgaacaagca    540
aagaaggtga taaccatgtt tgttcagcga caggtgtttg ctgagaacaa ggatgagatt    600
gctttagtcc tgtttggtac agatggcact gacaatcccc tttctggtgg ggatcagtat    660
cagaacatca cagtgcacag acatctgatg ctaccagatt ttgatttgct ggaggacatt    720
gaaagcaaaa tccaaccagg ttctcaacag gctgacttcc tggatgcact aatcgtgagc    780
atggatgtga ttcaacatga acaatagga aagaagtttg agaagaggca tattgaaata    840
ttcactgacc tcagcagccg attcagcaaa agtcagctgg atattataat tcatagcttg    900
gagaaatgtg acatctccct gcaattcttc ttgcctttct cacttggcaa ggaagatgga    960
agtggggaca gaggagatgg cccctttcgc ttaggtggcc atgggccttc ctttccacta   1020
aaaggaatta ccgaacagca aaagaaggt cttgagatag tgaaatggt gatgatatct     1080 ttagaaggtg aagatgggtt ggatgaaatt tattcattca gtgagagtct gagaaaactg   1140
tgcgtcttca agaaaattga gaggcattcc attcactggc cctgccgact gaccattggc   1200
tccaatttgt ctataaggat tgcagccatat aaatcgattc tacaggagag agttaaaaag    1260
acttggacag ttgtggatgc aaaaccccta aaaaagaag atatacaaaa agaaacagtt   1320
tattgcttaa atgatgatga tgaaactgaa gttttaaaag aggatattat tcaagggttc   1380
cgctatggaa gtgatatagt tccttctctc aaagtggatg aggaacaaat gaaatataaa   1440
```

-continued

| | | | | | |
|---|---|---|---|---|---|
| tcggagggga | agtgcttctc | tgttttggga | ttttgtaaat | cttctcaggt | tcagagaaga | 1500 |
| ttcttcatgg | gaaatcaagt | tctaaaggtc | tttgcagcaa | gagatgatga | ggcagctgca | 1560 |
| gttgcacttt | cctccctgat | tcatgctttg | gatgacttag | acatggtggc | catagttcga | 1620 |
| tatgcttatg | acaaaagagc | taatcctcaa | gtcggcgtgg | cttttcctca | tatcaagcat | 1680 |
| aactatgagt | gcttagtgta | tgtgcagctg | cctttcatgg | aagacttgcg | gcaatacatg | 1740 |
| ttttcatcct | tgaaaaacag | taagaaatat | gctcccaccg | aggcacagtt | gaatgctgtt | 1800 |
| gatgctttga | tagactccat | gagcttggca | aagaaagatg | agaagacaga | cacccttgaa | 1860 |
| gacttgtttc | caaccaccaa | aatcccaaat | cctcgatttc | agagattatt | tcagtgtctg | 1920 |
| ctgcacagag | ctttacatcc | ccgggagcct | ctacccccaa | ttcagcagca | tatttggaat | 1980 |
| atgctgaatc | ctcccgctga | ggtgacaacg | aaaagtcaga | ttcctctctc | taaaataaag | 2040 |
| acccttttc | ctctgattga | agccaagaaa | aaggatcaag | tgactgctca | ggaaattttc | 2100 |
| caagacaacc | atgaagatgg | acttacagct | aaaaaattaa | agactgagca | aggggagcc | 2160 |
| cacttcagcg | tctccagtct | ggctgaaggc | agtgtcacct | ctgttggaag | tgtgaatcct | 2220 |
| gctgaaaact | tccgtgttct | agtgaaacag | aagaaggcca | gctttgagga | agcgagtaac | 2280 |
| cagctcataa | atcacatcga | acagttcttg | gatactaatg | aaacaccgta | ttttatgaag | 2340 |
| agcataggct | gcatccgagc | cttccgggaa | gaagccatta | agttttcaga | agagcagcgc | 2400 |
| tttaacaacc | tcctgaaagc | ccttcaagag | aaagtggaaa | ttaaacaatt | aaatcatttc | 2460 |
| tgggaaattg | ttgtccagga | tggaattact | ctgatcacca | aagaggaagc | ctctggaagt | 2520 |
| tctgtcacag | ctgaggaagc | caaaaagttt | ctggccccca | aagacaaacc | aagtggagac | 2580 |
| acagcagctg | tatttgaaga | aggtggtgat | gtggacgatt | tattggacat | gatataggtc | 2640 |
| gtggatgtat | ggggaatcta | agagagctgc | catcgctgtg | atgctgggag | ttctaacaaa | 2700 |
| acaagttgga | ngcggccatt | caaggggagc | cangntctca | agnntttcnt | tgagagggag | 2760 |
| ccgaggcana | nangnaaatt | nnncccnccc | ccc | | | 2793 |